US008396802B2

(12) United States Patent
Dala et al.

(10) Patent No.: US 8,396,802 B2
(45) Date of Patent: Mar. 12, 2013

(54) SYSTEM FOR REMOTE REVIEW OF CLINICAL DATA OVER A VULNERABLE SYSTEM

(75) Inventors: Seema Dala, Camden, NJ (US); Praveen Dala, Camden, NJ (US)

(73) Assignee: MVISUM, Inc., Camden, NJ (US)

(*) Notice: Subject to any disclaimer, the term of this patent is extended or adjusted under 35 U.S.C. 154(b) by 0 days.

(21) Appl. No.: 13/564,114

(22) Filed: Aug. 1, 2012

(65) Prior Publication Data

US 2013/0024381 A1   Jan. 24, 2013

Related U.S. Application Data

(63) Continuation of application No. 13/162,298, filed on Jun. 16, 2011, now Pat. No. 8,260,709, which is a continuation of application No. 11/778,751, filed on Jul. 17, 2007, now Pat. No. 7,974,924.

(60) Provisional application No. 60/831,820, filed on Jul. 19, 2006.

(51) Int. Cl.
*G06F 21/00* (2006.01)

(52) U.S. Cl. .................. 705/52; 705/50; 705/51; 705/2; 705/3; 705/901; 705/904; 705/909; 380/231

(58) Field of Classification Search ...................... 705/52
See application file for complete search history.

(56) References Cited

U.S. PATENT DOCUMENTS

| | | |
|---|---|---|
| 5,845,255 A | 12/1998 | Mayaud |
| 5,954,663 A | 9/1999 | Gat |
| 6,093,146 A | 7/2000 | Filangeri |
| 6,168,562 B1 | 1/2001 | Miller et al. |
| 6,302,844 B1 | 10/2001 | Walker et al. |
| 6,336,900 B1 | 1/2002 | Alleckson et al. |
| 6,360,324 B2 | 3/2002 | Van Blarkom |
| 6,383,137 B1 | 5/2002 | Berry |
| 6,416,471 B1 | 7/2002 | Kumar |
| 6,475,146 B1 | 11/2002 | Frelburger et al. |
| 6,520,910 B1 | 2/2003 | Kohls |
| 6,589,170 B1 | 7/2003 | Flach et al. |
| 6,616,613 B1 | 9/2003 | Goodman |
| 6,641,533 B2 | 11/2003 | Causery et al. |
| 6,661,842 B1 | 12/2003 | Abousleman |
| 6,823,203 B2 | 11/2004 | Jordan |
| 6,874,085 B1 | 3/2005 | Koo et al. |
| 7,165,175 B1 | 1/2007 | Kollmyer et al. |
| 7,171,625 B1 | 1/2007 | Sacchi |
| 7,310,651 B2 | 12/2007 | Dave et al. |
| 7,386,717 B2 | 6/2008 | Adusumilli |
| 7,433,853 B2 | 10/2008 | Brockway et al. |
| 7,467,399 B2 | 12/2008 | Nadalin et al. |
| 7,519,591 B2 | 4/2009 | Landi et al. |
| 7,520,611 B2 | 4/2009 | Franz et al. |
| 7,668,835 B2 | 2/2010 | Judd et al. |
| 7,805,377 B2 | 9/2010 | Felsher |

(Continued)

FOREIGN PATENT DOCUMENTS

WO   WO2008011063   11/2008

*Primary Examiner* — Jacob C. Coppola

(74) *Attorney, Agent, or Firm* — The Marbury Law Group, PLLC

(57) ABSTRACT

A system for remotely reviewing medical data allows medical data to be transmitted over a vulnerable network to a physician's mobile device. The system includes a console, a data server and mobile devices. The system may include medical imaging equipment, medical records databases, and other sensors. Medical data is routed through the console to the data server to reach the mobile device via a wireless network. Patient's medical file may be separated into a demographics layer and a data layer, and separately encrypted using different encryption keys for the demographic layer and the data layer. Servers in the communication and processing system are provided with a decryption key for the layer processed by such server. Physicians may transmit comments to the requestor through the same system. A resident messaging system may notify users of messages or data awaiting review along with the urgency of the required review are also described.

22 Claims, 22 Drawing Sheets

U.S. PATENT DOCUMENTS

| | | |
|---|---|---|
| 2002/0010679 A1 | 1/2002 | Felsher |
| 2002/0077985 A1 | 6/2002 | Kobata et al. |
| 2002/0188709 A1 | 12/2002 | McGraw et al. |
| 2003/0037054 A1 | 2/2003 | Dutta et al. |
| 2003/0182443 A1 | 9/2003 | Wang et al. |
| 2003/0231190 A1 | 12/2003 | Jawerth et al. |
| 2004/0030893 A1 | 2/2004 | Karamchedu et al. |
| 2004/0121757 A1 | 6/2004 | Laumen et al. |
| 2004/0153712 A1 | 8/2004 | Owhadi et al. |
| 2004/0260666 A1 | 12/2004 | Pestotnik et al. |
| 2005/0091338 A1 | 4/2005 | De la Huerga |
| 2005/0223412 A1 | 10/2005 | Nadalin et al. |
| 2005/0283620 A1 | 12/2005 | Khulusi et al. |
| 2006/0059185 A1 | 3/2006 | Bocking et al. |
| 2006/0085347 A1 | 4/2006 | Yiachos |
| 2006/0095022 A1 | 5/2006 | Moll et al. |
| 2006/0143051 A1 | 6/2006 | Eggers et al. |
| 2006/0149597 A1 | 7/2006 | Powell et al. |
| 2006/0184455 A1 | 8/2006 | Meyer et al. |
| 2006/0195341 A1 | 8/2006 | Haaksma et al. |
| 2007/0050212 A1 | 3/2007 | Kearby et al. |
| 2007/0225574 A1 | 9/2007 | Ueda |
| 2008/0097912 A1 | 4/2008 | Dicks et al. |
| 2008/0097917 A1 | 4/2008 | Dicks et al. |
| 2008/0222040 A1 | 9/2008 | Halsted et al. |

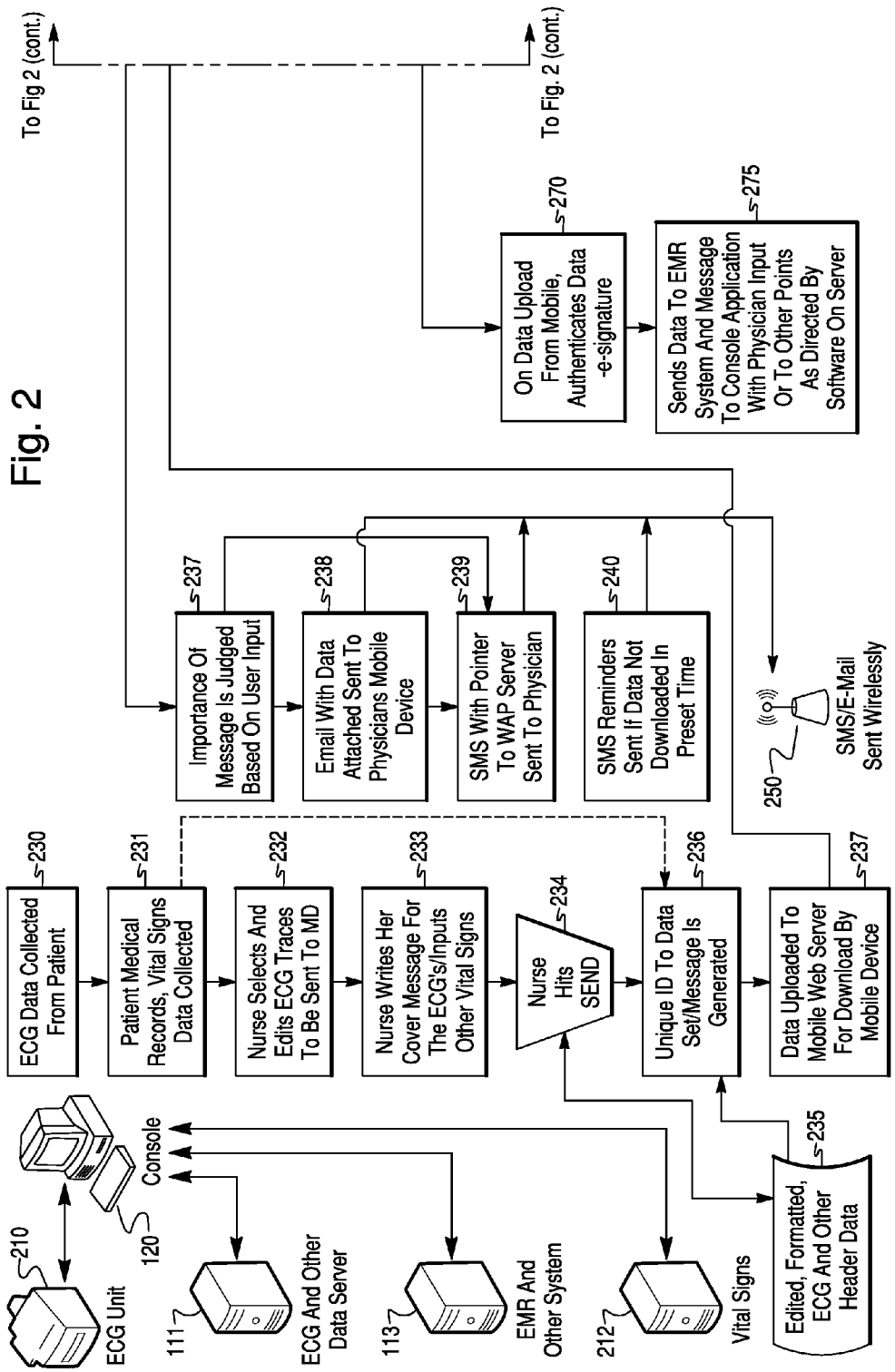

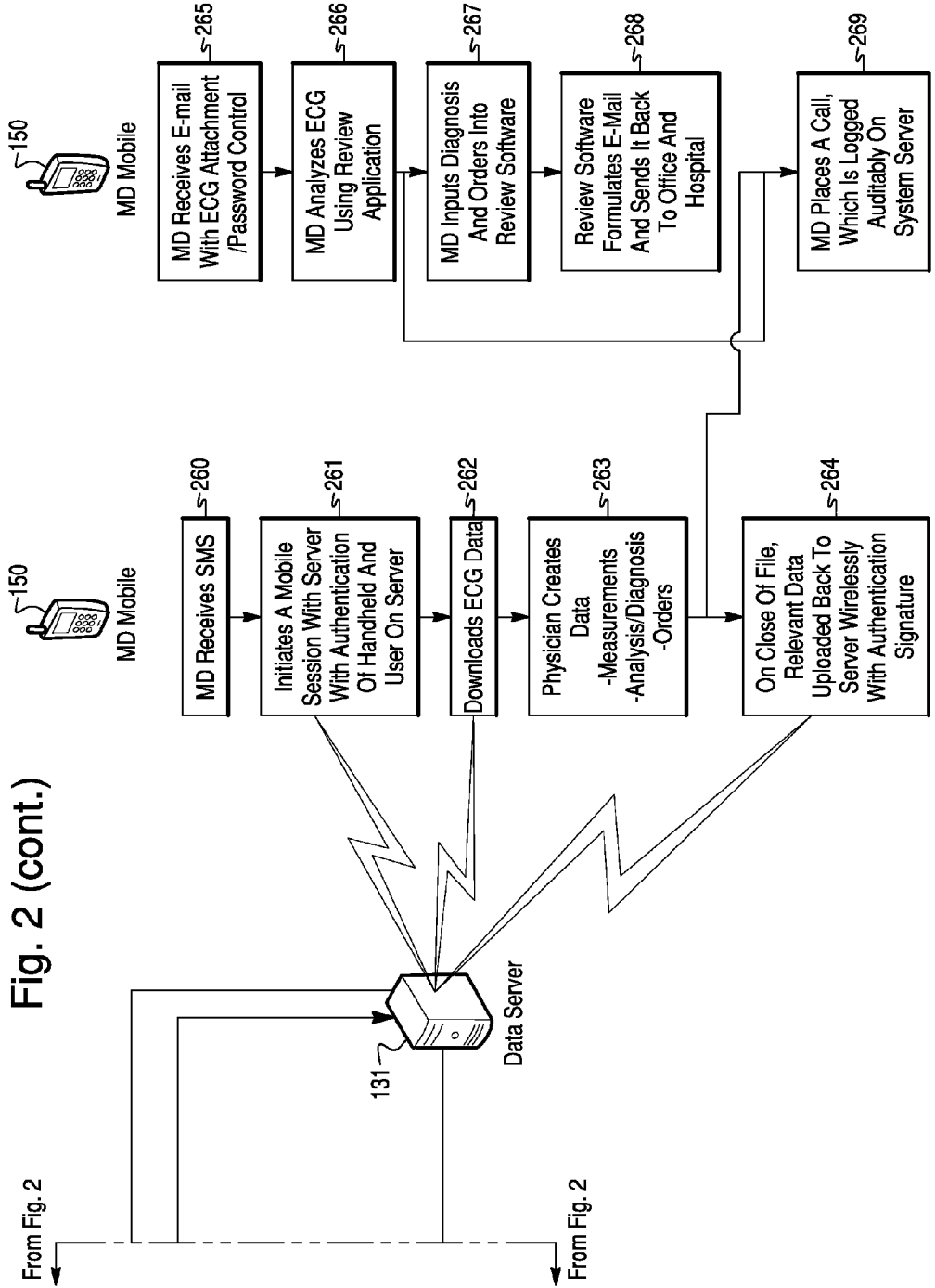

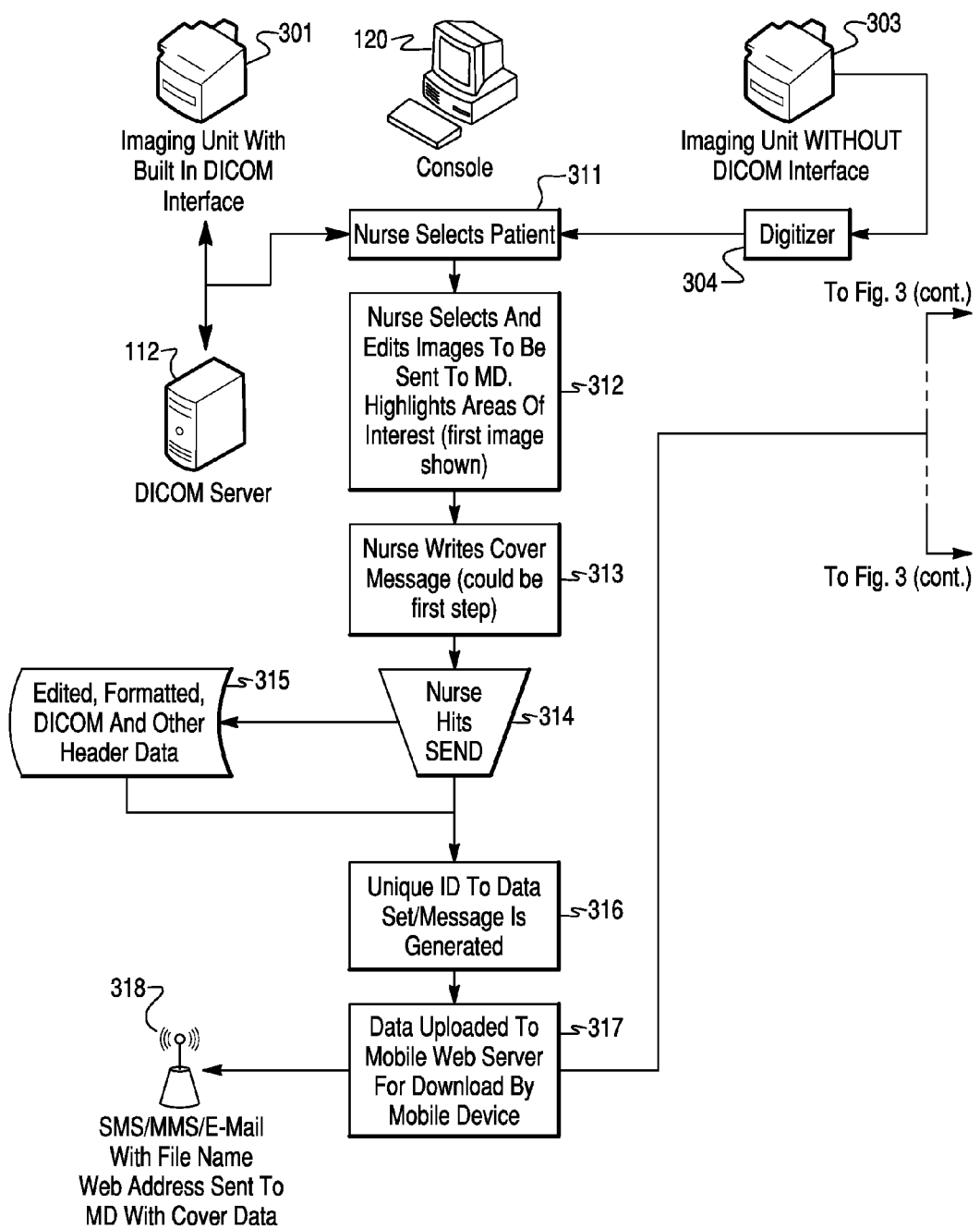

SYSTEM FOR REMOTE REVIEW OF CLINICAL DATA OVER A VULNERABLE SYSTEM

RELATED APPLICATIONS

The present application is a continuation of U.S. patent application Ser. No. 13/162,298, titled "Medical Data Encryption for Communication Over a Vulnerable System," filed Jun. 16, 2011, which is a continuation of U.S. patent application Ser. No. 11/778,751, filed Jul. 17, 2007, that issued as U.S. Pat. No. 7,974,924, which claims the benefit of priority to U.S. Provisional Application No. 60/831,820, filed Jul. 19, 2006, the entire contents of both of which are hereby incorporated by reference.

The present application is also related to U.S. patent application Ser. No. 11/778,744, entitled "System For Remote Review Of Clinical Data," now abandoned, and to U.S. patent application Ser. No. 11/778,731, entitled "Method For Remote Review Of Clinical Data," now abandoned, both of which were filed contemporaneous with U.S. patent application Ser. No. 11/778,751, and the entire contents of both of which are hereby incorporated by reference.

FIELD OF THE INVENTION

The present invention relates generally to medical information systems, and more particularly to a system, method and apparatus for accessing patient data remotely on a handheld device and reviewing critical patient data to reach informed clinical decisions.

BACKGROUND

With the deployment of medical communication systems which transfer data from within the hospital to physician-carried mobile communication devices via public cell phone and other networks, the need for encrypting such sensitive data will become significant. In applications where patient medical data has to be further stored or processed outside the hospital, such as on a public or shared server or a cell phone system file server, there will be a need for file handling methods which preclude accessing or reassembling the patient's data other than by a password protected physician handheld.

While encryption and authentication technologies are currently available, such technologies only allow transmission of data from the encryption point to the decryption point, with no further protection offered post decryption. In instances, where data needs to be decrypted at an intermediate point for further processing (such as for message delivery or routing purposes), standard encryption techniques are not sufficient.

Current laws applicable to medical data in the USA, such as HIPAA, require that any server storing patient medical data be secure with access limitations and written agreements to control access to the data. However, in wide implementations, such controls, although systematically possible, are not foolproof. A fool-proof system for managing such scenarios is required where, even if the security of a server is breached, data located within the server cannot be reassembled into meaningful parts.

SUMMARY

The various embodiments provide systems for processing sensitive patient medical information in an open environment, such as a shared server, without compromising critical information, such as patient demographics. Medical data files are separated into separate parts, files or layers, with one part, file or layer encrypted such that it can only be decoded by the intended recipient, while the second part, file or layer is encrypted such that it can be decoded at an intermediary processor, such as a server, to perform any processing required without compromising or reducing the security of the overall data. In an embodiment, a first layer of medical data includes the patient's identity and demographic information while a second includes medical information, such as medical images, laboratory reports or diagnostic data.

BRIEF DESCRIPTION OF DRAWINGS

The accompanying drawings, which are incorporated herein and constitute part of this specification, illustrate exemplary embodiments of the invention, and, together with the summary description given above and the detailed description given below, serve to explain various features of the invention.

FIG. 2 is a system illustration and flow diagram of a method for communication medical information according to an embodiment.

DETAILED DESCRIPTION

Figure 1:
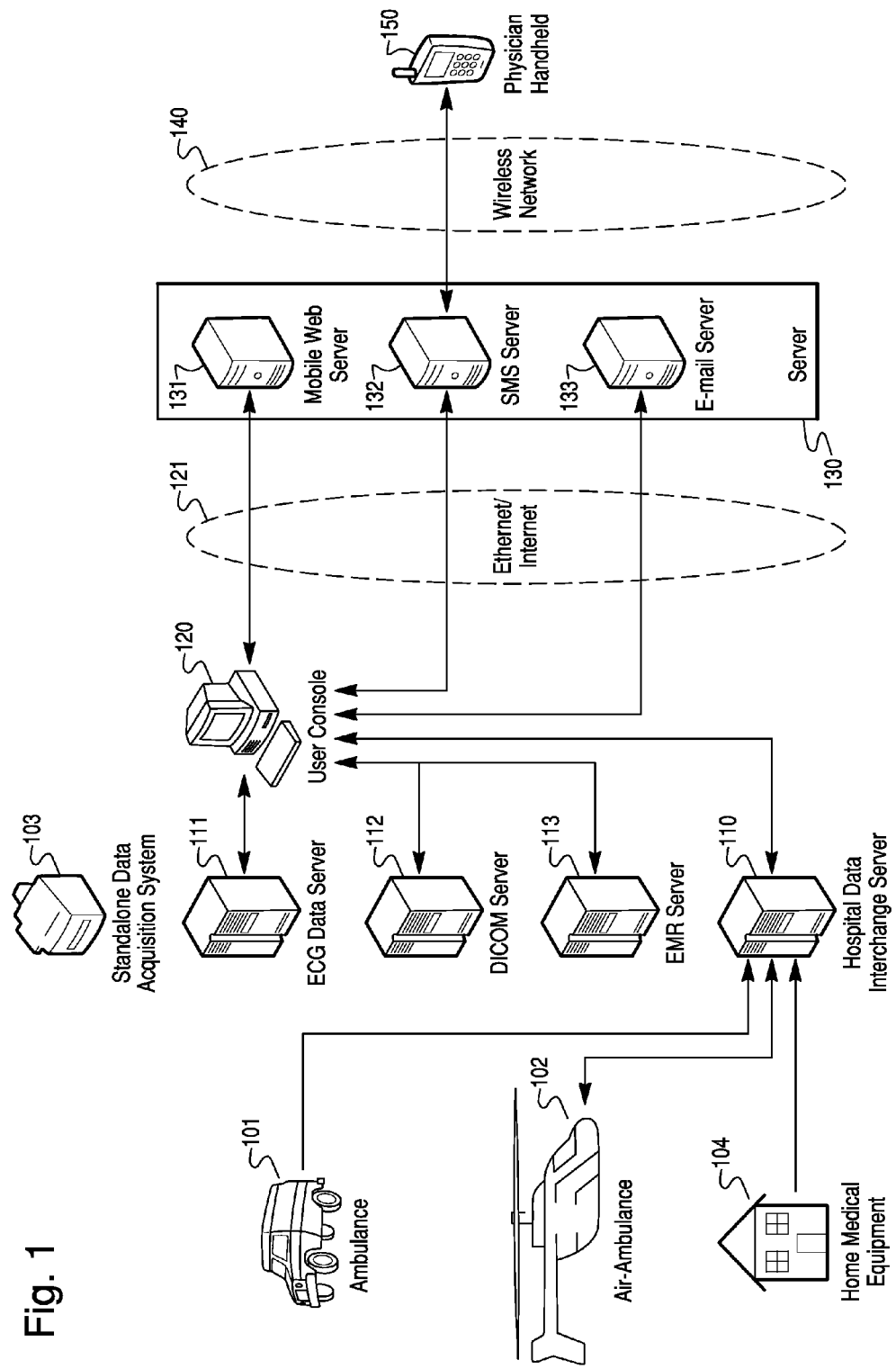
FIG. 1 is an illustration of a system for communicating medical information to a physician's handheld device according to an embodiment.

The various embodiments will be described in detail with reference to the accompanying drawings. Wherever possible, the same reference numbers will be used throughout the drawings to refer to the same or like parts.

The term "hospital" is used herein to mean "any healthcare delivery location". Any embodiment described herein as in a "hospital" or relating to a "hospital" includes physician offices, emergency and urgent care centers, rehabilitation centers, ambulances, and such other patient care points where patient data can either be acquired, handled, stored, and/or interpreted. It has also to be noted that this structure could be used in other data processing scenarios, such as in remote review of medical images (telemedicine), clinical study protocols, etc.

The various embodiments address the needs described above. The various embodiments may also be relevant to other secure communication systems where part of the data needs to be readable at an intermediate way-point, or in situations such as in blinded clinical studies where patient data or other elements of a data file are to be hidden while relevant data needs to be selectively accessible to different parts of the client base.

Systems and techniques for enabling communication of medical information between the source of clinical data, such as ECG machines, imaging equipment, or databases of such information such as hospital electronic medical record systems or subsystems thereof, and a physician's mobile device are disclosed in U.S. patent application Ser. Nos. 11/778,744, entitled "System For Remote Review Of Clinical Data" and 11/778,731, entitled "Method For Remote Review Of Clinical Data", the entire contents of both of which are previously incorporated by reference. The various embodiments of the present invention provide methods for securing medical information sent over communication systems with public components, such that security can be assured even in instances where security of a data server may be breached.

For diagnosing and treating patients, physicians rely on patients' personal and medical information. This sensitive information is collected and stored as patients' medical records and may include information such as patients' personal identity (e.g., name, address, date of birth, social security number, etc.), present and past medical history, physical examinations, vital signs, laboratory data, imaging data and any other measurements taken or treatments planned by healthcare providers. Because physicians rely on this data to manage patients, ready access to such records is important to reducing the time and cost of patient care and medical services.

Accessibility to medical records is particularly important when effective diagnosis and treatment depends on timely assessment of medical data. In many instances, quick diagnosis and proper treatment of an illness, injury or condition can mean the difference between life and death. For example, a patient with chest pain may be suffering a heart attack, in which case timely diagnosis and treatment may prevent death or long term disability of the patient.

Ready access to medical records is also important for reducing the costs of healthcare. For instance, when a medical consult is requested from a third party physician, the ability to remotely access medical information may reduce the cost and improve the effectiveness of the consult by allowing physicians to evaluate patients from a location other than the bedside, reducing the time and cost of travel to the patient location unless it is necessary.

To render an opinion, make an order and/or prescribe a treatment plan a physician must be able to readily access and evaluate a patient's medical records. However, there are many situations in which today's healthcare systems fail to provide physicians with ready access to medical records. For instance, a physician's expert opinion may be required to manage a hospital patient after normal business hours. However, physicians are currently unable to receive comprehensive medical records from any location other than at a patient's bed-side or from the hospital record center. To obtain medical records and to compensate for the insufficiencies in current medical information systems, physicians may exercise several methods. First, a physician may travel to the medical facility to physically review the patient's medical records. This can be time consuming and expensive, potentially delaying patient care and impacting the physicians' quality of life. Second, to procure a medical opinion, medical records may be read to physicians over the telephone. This method is inefficient and may lead to misdiagnosis and mistreatment since such verbal communication may be misunderstood and the import of medical information may not be fully appreciated by the physician. In addition, some types of medical information, such as Electrocardiograms (ECG, a.k.a. EKG) and medical images, cannot be readily described over a telephone and so may need to be faxed to a physician. Facsimile transmissions run the risk of compromising patient confidentiality, and the quality of records received by facsimile may not be optimal. Finally, a hospital may post patient medical records on a website portal which may be accessed by registered physicians. Once a physician is paged or called for consultation, the physician may access the medical records over the World Wide Web (WWW) using a computer. However, a physician's access to virtual medical information is tied to access to the Internet and a computer which not only hinder his mobility but also may reduce his availability.

The above-mentioned methods for accessing medical records are also ineffective during medical emergencies or when medical data must be reviewed immediately. For example, an obstetrician consulting a neonatologist must physically be present on location to review time-critical data in order to render an opinion. Similarly, a cardiology consult must be physically present during the performance of an echocardiogram (Echo) to rule out or diagnose heart disease in a patient with acute chest pain.

The currently available methods for accessing patient medical records also fail to deliver time-critical medical data from ambulances or field medical devices to treating the physicians before the field emergency crew arrives to the medical facility. Field emergency personnel face difficult situations when, for example, their time of arrival to a medical facility is delayed due to traffic and critical medical decisions are pending. In many instances, correct and timely medical diagnosis and guidance by physicians located remotely at a medical facility could reduce the morbidity and mortality rate of patients being transported. Such timely medical diagnosis and guidance can only be achieved when the physician located at the medical facility can access medical data collected by the field medical personnel.

Medical record accessibility is complicated by the strict requirements and guidelines set by the Federal and State Governments in regulations such as the Health Insurance Portability and Accountability Act (HIPAA). HIPAA requires that healthcare facilities implement restrictive security systems to protect patients' medical information. Thus, while there is a need for mobile access to medical records, such access must also prevent medical records from being compromised, either by accident or by malicious efforts.

The cost of caring for patients at a medical facility and billing for such costs generally must be tied to physicians' actions, diagnoses and treatment recommendations. A complete patient care record, including a physician's treatment plan, also may be important in legal proceedings resulting from patients suing physicians. Therefore, it is important that medical facilities collect and maintain accurate records of physician actions, diagnoses and treatment plans for every patient. Currently, remote diagnosis and treatment of patients do not allow physicians to personally and directly enter their findings and treatment plans into patient charts.

There is, therefore, a need for systems which can make medical data accessible to physicians at any location, at any time, and without significant delay while complying with all the privacy laws and regulations. Such systems must be capable of reviewing these multiple types of medical data, and also allow physicians to communicate their findings, orders and treatment plans to the appropriate persons. Furthermore, such systems must be able to maintain an accurate record of physician's attendance to patients. The various embodiments of the present invention provide systems, methods and apparatus to meet these needs.

The various embodiments provide systems, methods and apparatus for managing and transmitting various types of patient information to a physician's mobile device, such as a cellular telephone, and for transmitting the physician's orders back to an attending facility. The various embodiments allow patient data from a collection device (e.g., medical diagnostic equipment) or a database containing patient data to communicate with a physician's mobile device thorough a server. Such servers can be configured so that the importance of a medical emergency or situation may be accurately transmitted to the physicians. The servers may also have a graded response capability wherein the server may contact the physicians in one or more different ways to ensure delivery of the data.

Examples of the types of data managed and communicated to a physician's mobile device include: patient demographic data, such as name, age, sex, current medications, prior diagnosis, etc.; time-variant one-dimensional data, such as electrocardiograms and electroencephalograms; still or moving images, such as ultrasound, X-ray, and catheterization lab images; laboratory results, such as cholesterol levels, urine test results, blood dissolved oxygen levels, etc.; and/or measurements of critical patient parameters, such as blood pressure, pulse rate, and body temperature. The data may be processed prior to transmission in order to minimize file sizes to allow it to travel over various networks such as wireless networks. The format of the data may also be optimized for viewing on the display of the physician's handheld device using processing software operating on a hospital console, network server or the handheld device itself. Such image optimization may enable a physician to view an accurate account of the transmitted images and perform measurements on any mobile device, even on mobile devices with suboptimal display resolution.

After reviewing the transmitted data on the handheld device, physicians may communicate their findings and prescriptions to the treating facility. All communications may be automatically recorded in patients' files for billing and record keeping. The transmitted physician orders may travel from the handheld device through a server to reach a console in the treating facility. The receiving console may then appropriately display or route all or portions of the physician's orders, either with some manual intervention or automatically, to sub-systems connected to the console or on the facility's network.

The various embodiments allow medical data to be accessed directly by a physician using a mobile device. This access may include data interactions, such as on-demand data transfers between electronic medical record databases and the physician's mobile device. The performance of such interactions may be optimized using multi-format networking, such as switching between wireless Ethernet and cell phone networks.

Further embodiments provide workflow enhancements such as automatic or semi-automatic integration with billing system and patient discharge where multiple messages must be sent to multiple personnel in multiple locations.

An exemplary embodiment of a general system for communicating patients' medical data to a physician's handheld device is illustrated in FIG. 1. As shown in FIG. 1, medical data may be collected in the field, such as an ambulance 101 or air-ambulance 102, or from diagnostic equipment, such as an ECG 103, within a medical facility. The collected medical data can be sent directly from a measuring device to a network, such as an Ethernet/Internet 121. Alternatively, medical data may be sent from a data collection device 101, 102, 103 to a user console 120 which is connected to the Ethernet/Internet 121. Medical data can be sent from the console 120 via the Ethernet/Internet 121 to a server 130 which is configured with software to transmit the data (either with our without processing) to a physician's mobile handheld device 150 using a wireless network 140. As illustrated in FIG. 1, physician's diagnosis and orders may be transmitted back to the user console 120 at a medical facility using wireless and wired data communication networks 121, 140. Once the physician's orders are received at the user console 120 in the medical facility, medical staff may treat the patient accordingly. It will be appreciated that the various functions implemented in this system may be accomplished in software and/or hardware implemented on the console 120, the server 130 and/or within the medical device or database server connected to the network.

Patient medical data may be collected in any number of conventional ways. For example, patient data may be collected in the field by a mobile medical facility such as a road ambulance 101 or an air-ambulance 102. Alternatively, a patient may be admitted to a non-mobile medical facility such as a hospital or an emergency clinic and medical data may be collected by, for example, a standalone ECG system 103 at that facility. Medical data may be collected by other medical devices, such as, patient monitors including various subsystems for each vital sign such as SpO2, temperature, Blood Pressure, heart rate, etc., various imaging equipment, pacemaker monitors and interrogation devices, laboratory equipment, and other medical data collection systems. Data may also be collected by a patient's home monitoring systems 104, which may report physical, chemical, electrical or other patient's medical parameters, as well as medical device status information necessary to determine the proper operation of a medical device.

Medical data from these various sources may be received and collected within a data interchange server 110. When the medical data is collected, it may be transmitted immediately to a physician's mobile device 150 or it may be stored for later use. If it is to be used at a later time, the collected patient data may be stored on hospital databases and/or servers. These databases or servers may include general hospital data interchange servers 110, department specific data servers such as an ECG server 111 or DICOM server 112, or a data consolidation server such as an electronic medical record (EMR) server 113.

Operation of the various embodiments may be best understood by considering an example of the system in action. In this example, a user, such as an emergency room (ER) nurse, on a hospital console 120 requests a physician's consultation on an urgent patient situation while the physician is not in the hospital. To make the consultation request, the user uses tools (e.g., a graphical user interface) on a user console 120 to select medical data that is to be transmitted to the physician. The user console 120 may be coupled to the data sources, such as an EMR server storing patient medical records, a DICOM image server or a medical device, such as an ECG server 111 by the hospital's network. The console may also be coupled to wireless and external networks so that it can receive medical data directly from remote sources, such as an ambulance 101, air-ambulance 102 or the patient's home systems 104. The user console 120 is also connected to an external network, such as an Ethernet/Internet 130 for communication with external data communication networks. The user may enter contextual information into the user console 120 to inform the physician of the nature of the request or emergency, the location of the patient, and the desired consultation or required action. In other instances, the identification of the console or data source, might itself automatically provide location information. If required, the user may use tools on the console 120 to retrieve stored medical records from historical and patient record databases from one or more of the available sources. Finally, the user may format or assemble the consultation request and associated medical data and transmit the assemblage as a message to be delivered to physician's handheld device 150. By way of the Ethernet/Internet 130 connection the message and data are sent to a message delivery server 130 where it is prepared for transmission to the physician's handheld device 150 via an available wireless network 140 linked to the mobile device. In a particular embodiment, the server 130 first sends an SMS message, via a cellular network SMS server 132, to the physician's handheld device 150 notifying the device that a data package is available for downloading. In response to the SMS message the handheld device 150 can send a download request back to the server 130 which then transmits the data via a server 131 (which may be optimized for communication to mobile devices, and hence sometimes referred to herein as a mobile web server), an e-mail server 133 or other wireless transmission facility. The physician then reviews the data presented on the handheld device, enters an order, observation, request or treatment plan, and transmits such information back to the user console 120 via the wireless network 140 and server 130.

It will be appreciated that the user console 120 may be a standalone computer or work station, or the processor within any of the example data source servers 110, 111, 112, 113, or a medical device 103, with the console functionality provided by an additional software program loaded on the processor. Also, in an embodiment, the console 120 may be located within the ambulance or air-ambulance to enable EMT personnel to transmit patient data directly to a physician without the need to involve an intermediary operator on a hospital console.

For example, the console 120 may be used as a separate system to retrieve data from the databases or data collecting devices to which it is connected, with such retrieval operations initiated automatically, semi-automatically or manually by operator commands. Various data collecting devices and databases may be connected to the console 120 either by wire or wireless networks. When the system is configured to automatically transmit data to the physician, data from medical devices may be transmitted to the console 120 and then automatically channeled to the communication server 130 where it is sent on to the physician's mobile device 150. This configuration may not require a console operator or a separate console processor as the console functionality may be incorporated into the medical device 103 processor or the server 130.

Manual entry of information onto a console 120 may include inputting information from the operators' own findings, retrieving information collected by medical devices, and/or retrieving patient medical records. It may also include entering data from multiple sources acquired either electronically by means of a communication link, or manually by means of a removable storage media such as floppy disks, or USB drives. In other instances, the console 120 operator may enter data manually by means of a keyboard and by copying and pasting from different applications resident on the same computer as the console 120 software program.

An example of data that may need to be entered manually into the console 120 is the patient's vital signs. In applications where only vital signs are of relevance, the data may be imported by electronic means, be copied and pasted from another connected resident software program on the same computer system, or manually entered into a tabulated form on the screen of the console 120 along with any comments. An example of such a situation is a console located within an emergency room into which an ER nurse may enter patient identity information and vital signs statistics, and/or connect patient monitoring equipment, such as an ECG machine, to receive and record medical data.

Once the medical information is collected and communicated with or entered into the console 120, the data may be encrypted or scrambled and transmitted through an Ethernet/Internet network 121 to a server 130. Such a network 121 may include the hospital's internal communication network, which may be wired, wireless or a combination of wired and wireless networks. The network 121 may include various firewalls and other security and network integrity features known in the art.

The server 130 may be located anywhere within a medical facility or be remotely located outside of such facility. Also, the server 103 may be located internal to the console 120, physically integrated into the console 120 or exist as a software program that resides within the console software. Alternatively, the server 130 or a portion of the functionality described herein as occurring on the server 130 may be integrated into or exist as a software program that resides within a processor coupled or integral to a medical imaging system, such as a CT scanner, X-ray system, ultrasound imaging system, EKG system, etc. The server 130 may be a single device dedicated to facilitating communication with physician handheld devices, or it may be a multipurpose network server that is additionally configured with software to perform the functions associated with physician handheld devices, or a collection of various servers/computers that offer different aspects of functionality needed to perform the necessary operations expected of such a server.

In general, the server 130 is configured to enable one or more medical facilities or their departments to upload data onto a common server 130 for transmission to physician handheld devices. The server 130 may include multiple functional units, with one or more of these units being part of a single computing system (i.e., as software function units) or located separately on separate processors. Examples of separate processors or functionality units include a mobile web server 131, an SMS message server 132, and an e-mail server 133. For example, a data server 131 is a functional unit which stores and distributes medical data in a secure fashion to systems with protected user access and may contain logic for distributing received data and messages. Such logic and authentication technologies may also be located in the console 120, with the server acting as a pure data source through which encrypted data is passed.

Another example of a functional unit is an SMS server or other messaging management server capable of sending messages to a device through a telephone network for mobile phones and devices. The SMS server 132 may be located within or separate from the server 130 and is capable of sending messages to mobile devices through a public cellular telephone network or a combination of different public telephone networks. The SMS server 132 may also be enabled to accept and recognize the urgency and criticality of correspondence messages which were communicated by the console 120 or receive from a handheld device 150. The SMS server 132, or the server 130 directing the SMS server 132, may include software to send timed and/or multiple messages to a physician's mobile device 150 until the relevant message data is successfully downloaded by the physician's device, or a response from the physician is logged by the data server 131 or the console 120. Alternatively, such functionality may reside in the console 120.

When messages are received by physicians, they are able to declare whether they are available to review the patient's data. This declaration may be entered into the handheld device as a message or as a response to a menu option. If the response is in the negative, the server 130 may be configured to inform the user at the console 120 as to the physicians' lack of availability. The consult request can then be re-routed to other available physicians by the user via the console 120.

Alternatively, a software application may be made available on the handheld device through which a physician may indicate his/her availability, which may then be communicated to the server 130. This information that the physician is not actively receiving messages may further be communicated to the console which may then indicate to the console user either while or before formulating a message to said physician, This information may further be used on the server to re-route messages to a different physician, if so set up, such that the console user is able to automatically get in touch with an expert physician in cases where the originally intended physician is not available.

In yet another embodiment, the primary functioning of which is detailed later with reference to FIG. 7, the server and the handheld may have communication methodologies included by which the server is updated from time-to-time regarding the availability of each physician's handheld device. Such availability information may be a combination of the handheld device storing and reporting each physician's personal options, such as a "do not disturb" option, and the handheld device's availability on the cellular network. Such physician availability self-reported information provided by this embodiment may also be used to support the functionality described in the previous paragraph.

Yet another unit of the server 130 may be an e-mail server 133. An e-mail server 133 may be configured send e-mail messages to the physician's mobile device 150, directly or indirectly, as well as receive messages in e-mail format sent by the console 120, the SMS server 132 other locations, such as a referring physician's office. The physician's mobile device 150 may download the e-mail message with the medical data attached using convention wireless e-mail message communication protocols. Such e-mail messages may be downloaded either automatically, in predefined time intervals (e.g., every 10 minutes), or manually when the physician is notified of the availability of an e-mail message by an asynchronous mode of messaging, such as an SMS message sent via the SMS server 132. Other modes of e-mail delivery currently known in the art may also be used.

Because the information communicated through this system may include critical patient medical information, it is important that the server 130, especially those servers that are remotely located, perform with high reliability and without delay. For example, the server 130 may be configured to detect problems with the delivery of a message to a physician's handheld device 150. This may be achieved, for example, by configuring one or more different or integrated pieces of software operating on the server 130 to periodically transmit test messages. Such test messages may mimic one or more aspects of the real messages routed through the server 130 or functional units of the server. Alternatively, the server 130 may simply send a periodic message requesting an acknowledgement response. The server 130 may further be configured with software to recognize when a message sent to a physician has not been received or when connectivity to the physician's handheld device is no longer available, and to notify the appropriate persons, such as an operator on the console 120, by one or more means of communication including e-mail, SMS messaging, paging etc. Such functionality helps assure speedy detection of communication flaws within the messaging server and thereby allow steps to be taken to increase reliability.

In addition to testing the communication links between the server 130 and the physician's handheld device, the server software may also initiate test or simulated message transmissions from different points within the server's 130 main software to check for proper reception at some other points downstream to the point of injection in the data flow path. Such testing can verify the integrity and reliability of the entire communication system, including network connections within the hospital infrastructure.

The foregoing description of communication link testing may also be performed over all types of communication links available to the system. For example, wireless communication links used to transmit data to and from physician handheld devices may also include 3G and satellite telephone data links. Thus, in addition to testing the conventional cellular telephone data network, the server 130 may periodically test backup communication links in a similar manner. If a backup link is determined to be unavailable or unreliable, that information may be communicated to the operator on the console 120, such as in the form of an informational message, a warning symbol or icon, or other display feature.

Because patient medical information is confidential whose protections and disclosure are governed by Federal and State laws and regulations, such as HIPAA, it is important that the communicated medical data is protected during its transmission. An embodiment of the present invention provides systems and methods for ensuring that all medical data is protected while they are transmitted and that only authorized persons have access to such data. The transmitted data may be encrypted or scrambled, and various user access validation steps may be incorporated to protect the integrity of the data and the privacy of the patient. For example, encrypted medical data may be transmitted from the server 130 to a physician's mobile device 150 only when the identities of the physician and the physician's mobile device are authenticated. The identity of a physician may be authenticated by requiring a time-sensitive log-in process with a strong password known only to the physician. Authentication of a mobile device may be achieved by identifying unique identifiers on the cell phone, such as the telephone number, the serial number of the device, the transponder ID number, or any such identification data, all of which can be loaded on the server 130 during the mobile device registration process.

Also, data may be encrypted before it is transmitted from the console 120 to server 130. Once at the server 130, part or all of the data can be decrypted. The data may again be encrypted before transmission to the mobile device 150 and only decrypted after the device and the person accessing the data have been authenticated. To prevent unauthorized persons from accessing sensitive patient data, the server 130 may also need to be protected with strong temporary passwords. Other methods for protecting data that are well known in the art, such as the use of digital certificates, may be used in addition to or in place of the above described methods.

In some installations, the server 130 may be a storage facility for storing electronic medical data from one or more data sources. In such installations, stored data may be accessed by using any secure public-domain network application, such as the Internet, provided that the software resident on the reviewing computer is capable of being authenticated and have software capabilities to decrypt or unscramble the stored data files.

In various embodiments, medical data stored in electronic format may be analyzed by the console 120 or server 130 in order to recognize diagnostically significant patterns that may be identified to a physician. For example, ECG data may be analyzed using pattern recognition software to identify abnormal patterns, such as arrhythmia, tachycardia, or fibrillation. When recognized, the console 120 or server 130 may be configured with software to automatically or semi-automatically transmit the conclusions, perhaps in combination with a selection of the ECG data, to the physician's handheld device. As another example, the console 120 or server 130 may be configured with software to evaluate several types of diagnostic data simultaneously in order to recognize potential diagnosis or identify potential risks. For example, the console 120 or server 130 may be programmed with knowledge-based diagnostic decision aid algorithms, such as those disclosed in U.S. Pat. No. 6,804,656, the entire contents of which are hereby incorporated by reference.

By performing data recognition and decision assistance algorithms in the console 120 or server 130, sophisticated diagnostic tools can be provided to the physician outside the hospital without overburdening the processor within the physician's handheld device. Typical cell phones have limited available memory and processing power, and therefore would be unable to provide timely analysis of complex diagnostic data. By placing the auto-recognition and expert system software on the console 120 or server 130 and promptly delivering the results to the handheld device, the physician receives the benefit of such analysis tools as if the analyses were being done on his handheld device.

The server 130 may also include other artificial intelligence-based functions, such as pro-actively locating and obtaining relevant patient information from the hospital's electronic medical record system and either having it ready for dissemination into the physician's handheld device, or delivering such data in the background to the handheld device for quick review. Examples of such artificial intelligence-based functions include preselecting or preloading previous or baseline EKG's, blood cholesterol measurements, last known weight, etc. for a patient whose EKG is being sent to the physician for a complaint of Chest Pain.

In an embodiment, an audit function may be provided by including software on the server 130 or console 120 to monitor and record all accesses to patient medical records and to create and maintain a record of all such accesses. In this capability, every time patient records are transmitted and/or reviewed via the system, that transaction may be recorded and maintained in a database for future reference. For example, when medical data is transmitted to a physician's handheld device, that transmission of data will be recorded and maintained in an audit file, in the patient's medial files, in a communications log file, or some other suitable database. Similarly, when a physician receives medical data or requests access to such data by authenticating his password with the system, his access may also be recorded and maintained in an audit file, in the patient's medical records, in a communications log file, or some other suitable database. This record may include the date and time of access, the type of records accessed, the identity of the person accessing the files and other parameters that may aid a security audit.

The auditing system may also include hierarchical access controls whereby accessibility to medical data is directly related to the level of clearance of the viewer. For example, while a physician may have the ability to view all the medical records of a patient, including labs, images and patient medical history, he/she may not have access to non-medical patient information, such as billing information or personal identifiers such as the social security number. On the other hand, a billing specialist may have access to patient billing information but not to any of the patient's medical records.

In an embodiment, user authentication capabilities may be included on the physician's handheld device. More than one person may have access to a mobile device and handheld devices are subject to being misplaced or stolen. To accommodate this, the system may be configured to identify and authenticate the person requesting access to medical records from a handheld device before the records are transmitted. Following authentication, the system may then transmit only those portions of the patient's medical records and other personal information that the authenticated user is authorized to view. For example, if a physician's nurse also has access to the system through the physician's mobile device, the nurse with be authenticated by his/her personal authentication information (e.g., user name and password, finger print scan, etc.) and will be allowed to receive and view only the specific portions of medical records for which the nurse is cleared.

FIG. 2 illustrates an exemplary embodiment of a portion of the system illustrated in FIG. 1 in which results of electrocardiograms (ECG) are transmitted to a physician's mobile device 150 to enable the physician to evaluate a chest pain patient without having to be in the hospital. This capability enables the physician to review the patient's relevant medical information, including viewing some or all of the ECG trace, on the mobile device 150 wherever the physician happens to be at the time. This allows the physician to make a quick evaluation and issue appropriate orders without the delay of traveling to the hospital and without completely interrupting the physician's activities. The physician can enter orders into the mobile device 150 which can then transmit those orders back to the server 130, which sends them on to the console 120, thereby providing the attending nurse or physician with a diagnosis and treatment plan. When evaluation of a chest pain patient is requested by the operator on the console 120 (e.g., ER nurse or physician), the relevant medical records transmitted to the physician's mobile device 120 may include the patient's illness history, past medical history, results of physical exam, vital signs, Echo results, ECG results, and/or any past ECG results for comparison.

Referring to FIG. 2, a chest pain patient's medical evaluation may include conducting an electrocardiogram using an ECG unit 210 and storing the ECG recordings within the patient's electronic medical records and/or in an ECG data server 111. When an evaluating physician, such as a cardiologist, is not physically present at the patient's bedside, ECG information collected from the patient may be communicated to the physician's mobile device 120. To communicate this information to the physician, the ECG information may first be transmitted to a user console 120. Additionally, medical records may be downloaded from an EMR database server 113 to the console. If vital signs are stored or recorded on another system, such as vital signs server 212, that information may also be downloaded to the console 212. From the console 120 the ECG recordings and other relevant patient medical records/information may be transmitted to the data server 131 which will in turn communicate that data to the physician's mobile device 150. Once the physician reviews the data, he may input his diagnosis and treatment plan into his mobile device 150 which will transmit this data back to those who requested the consultation via the data server 131 and the console 120.

The process for effecting this communication begins with the collection of new data from the patient or by using previously collected data, step 230. New ECG recordings may be obtained by attaching leads of an ECG machine 210 to the patient's body. The recoded ECG may be transmitted automatically to the console 120 as the ECG machine 210 records the activity of the patient's heart. The ECG recording may also be archived in an ECG database 111 and then transmitted to the console 120 from that data server 111. Other previously recorded ECG for the same patient may also be available in the data server 111. When, for instance, a comparison of a patient's current ECG with old ECG results is required, both ECG records may be obtained and transmitted to console 120.

Similarly, vital signs which are a collection of a patient's biological measurements such as, SpO2, temperature, heart rate and blood pressure, may be retrieved for transmission, step 231. Vital signs measurements may be obtained from separate units, from a central database, such as a vital signs server 212, a patient monitor, or a central monitoring station. Vital signs may also be continuous recordings of breathing, or continuous time-variations of SpO2 or such other parameters. Other data, such as patient's demographics, or patient's present illness history or past medical history and results of physical exams may also be obtained from an electronic medical records system 113. Once this various medical data is obtained, it may be transmitted to console 120 for further processing. All transmissions of data between the data collection devices, medical databases, the console 120, the data server 131 and the mobile device 150 are encrypted and secured.

In an exemplary embodiment, instead of being a separate unit, the console 120 may be a software program embedded within a device which collects or stores medical data, such as the ECG machine 210, ECG data base server 111, vital sign server 212, or the electronic medical records system server 113. Medical data, such as ECG records may be communicated to the console 120 by a custom interface developed with one or more ECG units through wired or wireless networks. Additionally, medical data, such as ECG recordings, may exist in any number of known formats, including DICOM, OpenECG, Philips XML, or FDA XML formats. The software operating in the console 120 or the server 131 may be configured to interpret received medical data in different formats and convert them to a common format before communicating such data to the rest of the system.

Once the ECG recordings and other relevant medical information has been downloaded to the console 120, it may be communicated with the data server 131 for transmission on to the consulting physician's mobile device 150. The process of transmitting medical data from the console 120 to the data server 131 may be either automatic or manual. In an automatic process, for example, the ECG unit 210 may be configured to transmit the collected ECG recordings to the console 120 which may be configured to transmit the data to the data server 131 automatically. The data server 131 then can transmit the data the mobile device 150 with a review request, with or without any auto-interpretation from the software resident on any one or more of the ECG unit, the console, and/or the server.

In a manual process, an operator may orchestrate the transmittal of data from the console 120 to the data server 131. To manually create and transmit a message to the data server 131, the console user, such as a nurse, may first need to log into the console 120 and authenticate his/her identity. Such authentication may be compliant with current Federal and State laws and regulations governing patient privacy protection, such as HIPAA regulations. Once the user is authenticated, the console 120 may guide the user to select a patient name, step 231, to establish access to those records. The selected patient's medical data is then sent to console 120 for the user's review, step 231. Once the medical data is available to the console 120, the user may select to add data such as, ECG records, step 230, of a patient to the message destined for the consulting physician. It will be appreciated that downloading ECG data, patient medical records and vital sign data may be performed in any order or sequence.

The user may edit the length of the ECG records or highlight portions of particular significance, step 232. Editing an ECG record allows the user to select relevant portions to be transmitted to the physician. This may be important because, for example, Holter monitor signals from the ECG database 111 could be several hours long. Therefore, editing out the irrelevant portions of an ECG medical record to allow transmittal of a short section of the record may be beneficial.

The user may also include and edit other relevant data, step 233. Such other data may include, for example, notes, new or old vital sign measurements, other medical data, such as ultrasound and/or X-ray images, and specific consultation requests. Adding additional material may be achieved through a direct interface between the console 120 and other medical records databases such as the vital signs measuring systems or databases 212. Additional data may also be added to any outgoing messages by manual entry of data via a keyboard into a free-text entering field, or through a structured data entry method, such as a form or spreadsheet presented on the console display. Such data may also be entered by copying and pasting from other databases, such as EMR systems.

Once a message is constructed, the user may classify the message as being, for example, urgent or non-urgent, or specify a required response time for obtaining a response from the consulting physician. Such functionalities may be important in cases where timely response is critical, such as when a patient's life may depend on an immediate consultation. The physician's availability and his/her field of specialty may be available through the databases which are accessible by the console 120 or reside on the remote server 131. Once all message contents are selected and the message has been assembled, the user may select to send the message, step 234. The message may then be given a unique ID by the console 120, step 236, encrypted using, for example, 128 bit encryption, and transmitted to the data server 131, step 237. The ID generation for the message may also be a function of the data server 131.

Once the data is transmitted from console 120 and uploaded by the data server 131, the data server 131 may authenticate the data and run error checks to confirm the data was successfully received. The server may first determine the importance of the message by reading the importance or time limit information entered by the user, step 237. Depending on the classification of the message received from the console 120, the data server 131 may do one of several things. The data server 131 may directly or through a different server send an SMS message or an e-mail message or both to the physician's mobile device 150 using a cellular phone network 250, step 239. If the data server 131 determines that the message is classified as important or urgent, step 237, it may automatically generate an SMS message including a pointer to a wireless access protocol (WAP) server (also referred to herein as a mobile web server), step 239, to also be sent to the physician's mobile device. Alternatively, if the data server 131 determines that the message is not classified as urgent, step 237, it may send an e-mail to the physician's mobile device 150, step 238. E-mail addresses of physicians may be available on the data server 131 or in the console 120, or may be manually included in the message by the user via data entry into the console 120. The data server 131 may be configured so that the e-mail transmitted to a mobile device 150 may carry the attached medical data or transmit the e-mail text without an attachment but with a hyperlink to a website from which the attachments may be retrieved.

The data server 131 may also be configured by software, on a case-by-case basis using known programming techniques, to allow selected sections of a transmitted message to reach the mobile device 150 within an SMS message. Such an SMS message may identify the sending console 120 and/or the requesting institution, the patient identifier, the type of data to be downloaded, and the urgency of the message. Other information, including the message composed by the sender, may also form parts of the transmitted SMS message. SMS messages may be a summarized version of the original message or may share unique identifiers with the complete uploaded data. Hyperlinks or data pointers in the SMS message can be included to allow the physician's handheld device 150 to access the complete uploaded data from the data server 131 by parsing the SMS message.

SMS messaging may also be used for background notifications to the physician or to the handheld device 150. Such SMS messaging may be a modification of currently known forms of SMS messages. SMS background messaging services can be modified to encompass more data (e.g., by using MMS formats). Alternatively, similar to current SMS systems, only the SMS message, explicitly or implicitly including the appropriate data links, may be displayed on a commercial cell phone. Use of conventional SMS messaging may require a sign-in and user authentication requirement encompassing all SMS functions on the handheld device in order to comply with HIPAA requirements.

All advantages of sub-functionalities of SMS and MMS messaging systems may also be included as system features. These may include confirmation of SMS/MMS delivery to the handheld device 150. Using the message acknowledgment feature of SMS/MMS messaging may allow the console 120 or data server 131 to calculate the physician's response time, or to send a reminder, step 240, if no response has been received from the physician within a set time period following delivery of the message. Alternatively, if a SMS is not confirmed as delivered within a certain period of time, another physician may be selected, either manually or automatically, for consultation, or another mode of communication, such as e-mail or telephone may be used to inform the physician.

In instances where the data server 131 receives data from a data transmittal means, the data server 131 may be configured to authenticate each point of data transmittal. Data transmittal means may include a console 120 or a mobile device 150. For example, the data server 131 may use a unique serial number assigned to each data transmittal means in order to authenticate it. Additionally, the data server 131 may be configured to authenticate any person using the transmittal means to provide sufficient data security and ensure patient privacy. This may be achieved by use of unique passwords or identifiers assigned to authorized users.

A mobile device 150 which receives an SMS message, step 260, will typically be configured with software applications capable of receiving and identifying SMS messages from data servers 131. Upon receipt of an SMS from a data server 131, the background application may launch a main data review application on the mobile device 150. To view any messages sent from data server 131, the reviewing party may first need to authenticate his/her identity, step 261. Once the user has been authenticated, the data review application may, automatically or manually, download the data files, step 262, such as the ECG records, from the data server 131 through a wireless cellular network. In an embodiment, the handheld device 150 initiates downloading of data files by activating a hyperlink or data file pointer included within the SMS (or e-mail) message that has been received, or simply by replying to the SMS (or e-mail) message and requesting data transmission.

The data review application may include features to facilitate the physician's review of sent medical data on the handheld device 150. For example, if the data review application is configured such that the physician has to permit the download of the data, then a reminding mechanism may be configured to alert the physician of pending messages that should be accessed or downloaded. The interval and frequency of such alerts may depend on the classification of the transmitted messages. Thus, if a message is marked urgent, then the intervals between reminder alerts may be short.

Once the physician accesses the transmitted medical data, he may review them and enter his comments or opinions, perform measurements, enter annotations at various sections of the data sent, devise a treatment plan, enter prescriptions or perform any task necessary to his consultation, step 263. Appropriate data entry modules, such as forms, text boxes, measurement tools, and annotation tools will be available as features of the data review application to enable the physician to carry out such essential activities.

In the course of his review, the physician may have clarifying or follow up questions regarding the transmitted data or the case. In such instances, the data review application may be configured to allow the physician to send a message through the data server 131 to the console 120. The console 120 or the data server 131 may also be configured with software to respond to such messages automatically or to present an alert or otherwise notify a user that a physician question has been received.

Upon completion of his/her review and entry of the relevant orders, notes, requests and data into the handheld device 150, the physician's response with all the relevant data may be uploaded to the data server 131 using wireless data links, step 264. The SMS transmission may include security and authentication information, such as a digital certificate to validate and authenticate the message to the data server 131. When the message is received, the data server 131 uploads the data from the mobile device, and performs authentication and message verification, step 270, and then transmits the physician's response back to the console 120, step 275, where it can be retrieved by the operator in treating a patient. Copies or portions of such data may also be converted to one or more other formats, such as HL-7 or XML, and sent to various hospital databases, such as the electronic medical record systems 113 or billing systems.

A mobile device 150 may also be configured to receive e-mails with electrocardiograms as attachments, step 265. In such an instance, the data review application may be launched to facilitate the physician's review of the message and attached data, step 266. As with SMS messages, the physician may input his/her diagnosis, orders, prescriptions etc. into the handheld device 150, step 267. The data review application may then formulate an e-mail and send it back to the data server 131, the referring physician, the physician's office and/or the hospital, step 268. This email sends relevant data back to the requesting facility or staff. At the hospital this transmitted data may be received by the console 120 via the hospital's electronic mail system. The data within such e-mail message may be compressed to allow minimum data density while also allowing sufficient encryption and authentication.

Since the physician's handheld device will typically be a cell phone, the physician also has the option to place a call to the hospital, such as to the user on the console who originated the message, step 269. The fact that the physician placed such a call, and in some cases the content of the conversation, may be important for billing, patient record keeping, hospital administration, malpractice liability, or other reasons. Accordingly, an embodiment provides capability to log when such a call is placed, data concerning the initiation/duration of the call and, in some cases, a recording of the conversation. This call-related data may be stored in various databases within the system, such as in the console 120, in the patient's medical records (e.g., by transmission of the recorded data from the console 120 to the EMR server 113), in a billing server, and/or in some other database for storing telephone consultation records.

In order to diagnose and treat certain illnesses or injuries, physicians may need to review medical images, such as X-ray, fluoroscopy, ultrasound, Computed Tomography (CT scan or CAT scan), Magnetic Resonance Imaging (MRI), Positron Emission Tomography (PET scan), etc. Medical images may be simple two-dimensional still images, such as an X-ray or a slice image from a CAT scan. Medical images may also be movies (or loops of movies) of two-dimensional scans, such as ultrasound scans (with or without color information) and cath lab cine loops. It is noted that some types of time-based (i.e., including moving images) medical images are created, stored and maintained as a series of still images even though they may normally be viewed by physicians as movie sequences. For example, cath lab films and cine loops are technically not movie files, but a series of still images that are maintained as separate JPEG files within a single DICOM folder. For simplicity of description and reference, medical image files maintained as a series of still images that may be viewed as a movie sequence are referred to herein and in the claims as a "movie" file. Thus, the term "movie" is intended to embrace any sequence of images that when viewed sequentially at an intended frame rate appear as a movie sequence.

Medical image may also be a collection of three-dimensional (3D) data sets, such as a 3D CAT scan, or time-dependent 3D data sets (sometimes referred to herein as four-dimensional medical images), such as a cardiac 3D scan using a CAT scanner or an echocardiogram. In order to display 3D images on two-dimensional display screens, such as a physician's handheld device, the images may be displayed in isometric form as isometric images. Similarly, time-dependent 3D data sets may be displayed as rotating isometric movies. Additionally, in some circumstances the physician may need to view photographs or video of the patient, the patient's injury, or a site of an operation (e.g., an image from an arthroscopic probe).

Figure 3:
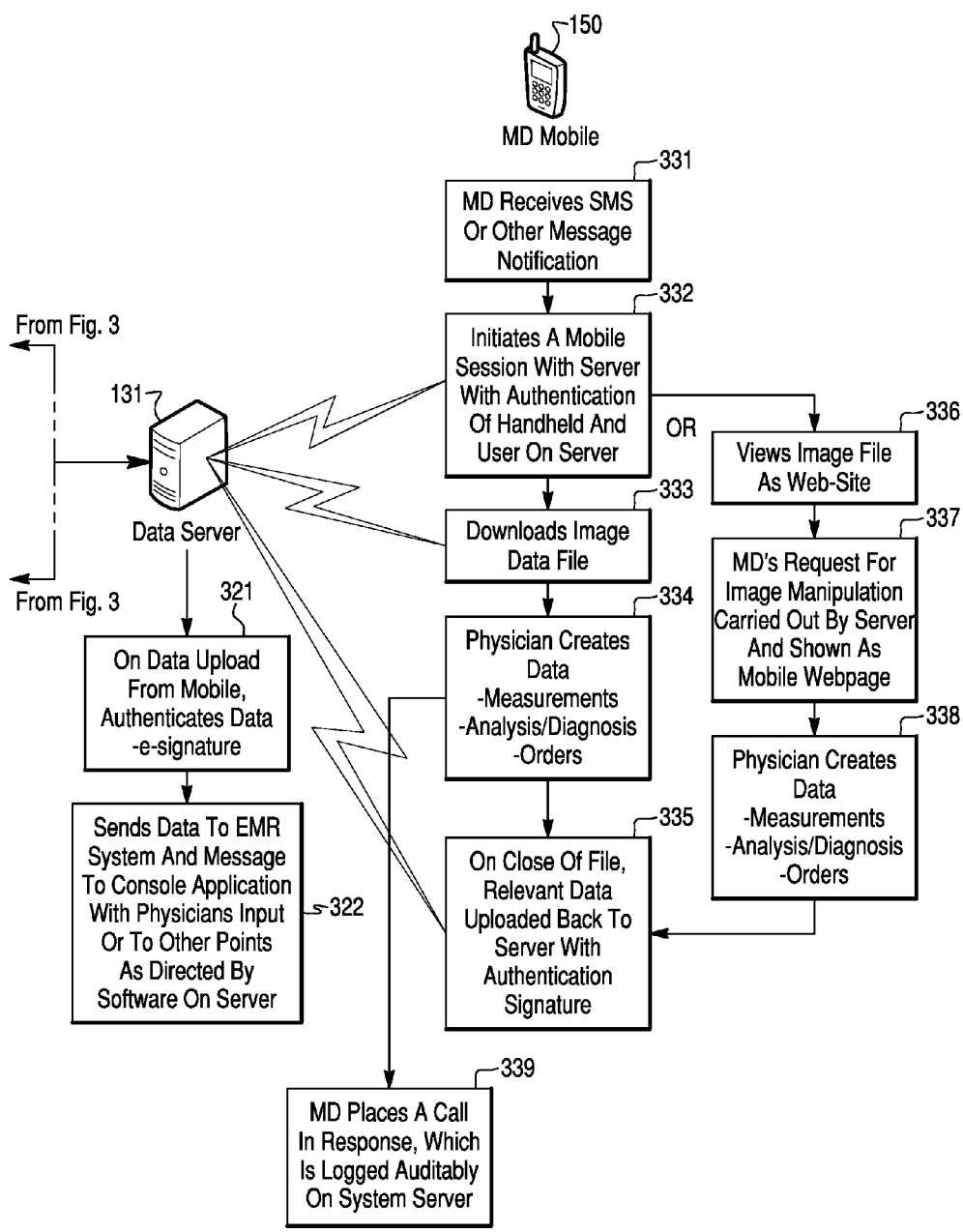
FIG. 3 is a system illustration and flow diagram of a method for communication medical information according to an embodiment.

FIG. 3 illustrates an exemplary embodiment of a system and method that enable communicating medical images to a physician's handheld device and providing tools to enable the physician to remotely review such images. Medical images may be collected by an image server with known format 112, such as DICOM, or an imaging device 301 also with known imaging formats. Alternatively, images generated by an imaging unit without known formats 303 may be digitized from an analog image output 304 using a frame grabber. Once the images are collected they can be transmitted or accessed by a console 120. These images may be stored in a database located either inside the console 120 or outside of the console such as in a DICOM server 112. Additionally, these outside database locations may include servers on the hospital information system.

An operator or user, such as nurse, may use the console 120 to access imaging data in order to create and transmit such data to a physician's mobile device 150 for consultation. To create such a message on the console 120, the nurse may select to access a patient's medical records, step 311. The nurse may then select one or more relevant medical images, or any sub area on an image (region of interest (ROI)) or sub-loop of selected images, step 312. To complete the consultation request message, the operator may then include any other necessary medical data or comments, including, for example, the patient's vital signs, medical history, ECG, etc., and write a cover message to the physician, step 313. The cover message may explain the patient's situation and the context of the attached medical files and images, as well as request a specific consultation or evaluation. When the data are assembled and cover message completed, the entire message may be sent, step 314, to the physician's mobile device 150.

From the console 120, the selected data with the selected attributes may be uploaded to the data server 131 in a known format, which could be DICOM format. The data transmission may be encrypted and error checked using methods like those described previously regarding ECG communications. Additionally, the console 120 may edit or format the information, and attach header data as necessary to facilitate its transmission to the physician's handheld device, 315. The console 120 may also perform one or more compression or optimization steps, or use selected data directly or indirectly to access other data that might be useful to have available on the server in case the physician requests this additional data implicitly or explicitly. Also, the console 120 may assign a unique ID to the message and data set to enable tracking and recording of the message and corresponding responses, 316.

The data server 131 receives the transmission from the console 120, 317. The data received at the data server 131 may include complete or partial image files in a known format along with the spatial and temporal description of the regions of interest identified, as applicable. At the data server 131, the image and message data are either transmitted to the mobile device 150 or are stored to be accessed by the mobile device 150. The data server 131 then prepares to transmit the message and image data to the physician's handheld device.

In a typical implementation, the data server 131 first sends an SMS message to the physician's handheld device, which is received and displayed, notifying the physician that a message is available for download, 331. The physician may initiate download of the message, such as by pressing a key or selecting a menu option, or the handheld device may automatically initiate download, 332. To download an image file, a mobile data exchange session is initiated with the data server 131 via cellular telephone data networks. As part of this step, the mobile device may also transmit to the server authentication information concerning the mobile device and the user to enable the data server 131 to confirm the identity of the user and the user's clearance to review the medical information in the message. The mobile device will also indicate the data to be downloaded, such as by initiating the communication via a hyperlink or attaching a point value included within the received SMS notification message.

Alternatively, the data server 131 may transmit the message and image data directly to the physician's handheld device without sending an SMS notification message or waiting for the request an authentication message.

Before sending image data, the data processor 131 may perform image processing in order to present the image in a format suitable for viewing on the physician's handheld device 150. The ability of a physician to view and analyze medical images will depend on the device's display characteristics (e.g., size, shape, resolution, refresh rate and range of colors displayed). Therefore, depending on the mobile device 150, the data server 130 may format the images before transmission to make them more easily accessed and displayed. To prepare the images for each mobile device, either the console 120 or the data server 131 may first detect the display and the specification of the targeted mobile device 150. This may be achieved in a number of ways. First, the console 120 or data server 131 may be configured to dynamically query the mobile device 150 to request it to transmit its display characteristic parameters before transmitting the images. Second, the console 120 or data server 131 may be configured (e.g., during system installation or upon registration of a physician with the system) with a database of mobile devices 150 correlated to each physician, with the database including the display characteristics of each device. By accessing this database, the console 120 or the data server 131 may determine the display parameters for the destination mobile device and prepare the image data accordingly. Third, the physician's mobile device may include its display characteristic data in the download request message (step 332). Other parameters that may be obtained in this step include the processor speed, the display processor speed (if separate such as in a dual-processor device), the display quality on the mobile handheld device (color depth etc.), the memory availability, the cellular network being used to access the data, the quality of the cellular connection in the general area where data is being accessed, etc.

Once the display characteristics of the destination mobile device 150 are known to the data server 131, image processing software operating on the server may format the images for that device. While an embodiment features the image processing software running on the processor within the mobile device 150, the preferred embodiment performs the image processing on an external processor, such as the console 120 or data server 131. Running the image processor software on an external processor shifts the processing load from the mobile device 150, which necessarily has limited processing and memory capability, to a processor which can be provided with sufficient processor and memory capabilities to complete image processing tasks very rapidly. Performing image processing on an external processor, such as the console 310 or the data server 320, can enable speedy transmission of data to the mobile device 150 by reducing the size of the file that must be transmitted. Performing image processing on an external processor enables more complicated image processing operations to be performed, such as image smoothing, edge detection and enhancement, and noise reduction, which would not be possible using the limited processing capabilities resident on the handheld device 150. This embodiment also allows use of conventional mobile devices 150, which may have slower processors, or inferior display driver capabilities, without having to upgrade or convert their image processors to provide sufficient processing speed and memory to receive, process and display large or complex medical images. Using a high speed external processor to quickly perform image processing and reduce the size of transmitted image files (thereby shortening the image transmission time) can make the display of images appear to the physician as if the images are being locally processed. Further, the responsiveness of the system from the physician's perspective can be improved by upgrading the external processor and its software without the need to replace all physician handheld devices with more expensive equipment.

To format an image, the image processing software may use the display parameters of a mobile device 150 to optimize the resolution and aspect ratio of transmitted images to match the display on the mobile device. Display parameters that may be considered in optimizing the transmitted image include, the screen resolution in terms of pixels and colors available (such as defined by the number of bits used in the color scale), or the number of pixels available for displaying the image (such as defined by the current screen resolution and the portion of screen made available for image display). For optimization purposes, the processing software may also calculate aspect ratio of the screen, such as calculating one or more frames of an image that corresponds to either a positive or negative zoom step (if discrete on the handheld) or determining the next possible resolution in the positive as well as negative directions wherein the region of interest of the image fits the screen aspect ratio. In the case of movie loops, the region of interest and the zoom and pixel sub sampling can be applied to each frame of the movie loop such that one or more loops with the appropriate zoom level are created at the server. More detailed descriptions of these image processing and transmission operations are provided below with reference to FIGS. 10-13.

The image processing software may be configured to assign priority to certain optimization steps. Such prioritizing of image optimization steps may allow the system to reduce the processing time. For example, the image processing software may be configured to optimize the resolution of an image and then optimize the aspect ratio. Since displays on handheld devices have relatively low resolutions, optimizing the resolution involves reducing the number of pixels in the image to be displayed, and thus the number of bytes in the image file. Optimizing the aspect ratio step may then involve processing far fewer bytes of information. As further example, if the image processing involves selecting a portion of the image to be presented as well as resolution and aspect ratio adjustments, the step of selecting a portion of the image may be performed first since this will leave a smaller image comprising far fewer bytes of information that needs to be processed during resolution optimization.

In an embodiment, the entire image, optimized only to suit the physician's handheld device display resolution limit, may be first downloaded to the physician's handheld device before processed and zoomed images are transmitted. This embodiment may be useful since in many cases the physician will want to see the entire image first to understand the nature and content of the image, even though details of interest may be too small to be seen clearly. Typically, physicians will then indicated portions of the image that they would like to view in detail (i.e., zoom images). The handheld device can then transmit requests for zoom images to the data server. Then, instead of sending processed images, the data server 131 can send a series of image formatting commands to the handheld device enabling the device's processor to display the portion of the image stored in memory that corresponds to the zoom request. Thus, the external processor performs the image processing steps of determining the portion of the image to display, including setting the aspect ratio, but instead of sending another image, it sends parameters (e.g., memory locations or image coordinates) that the processor can use to quickly generate the desired display from the image data stored in the handheld device's memory.

In an embodiment, predictive algorithms may also be used in the external processor software to anticipate likely requests by the physician so that preprocessing of image data can be accomplish, further shortening the time to respond to image requests, like zoom step requests. For example, in the situation where the physician requests a positive or negative zoom step, the processor may perform part or all of a second (or more) positive or negative zoom processing step, anticipating that the physician may want to continue zooming in or out. Similarly, in response to a pan request, such as a request to show the next increment of the image left, right, up or down, the processor may perform some or all of the next one or more pan image processing steps, anticipating that the physician may want to continue panning in the same direction. By anticipating the next image processing request, the external processor can have some or all of the image processing accomplished when the next image request arrives, enabling it to immediately transmit the requested image.

While performing image processing in an external server is presently the preferred embodiment, the invention should not be limited to the foregoing embodiments. It is well known that data transmission network speeds and processor speeds used in mobile devices are constantly improving. Therefore, with the advances in technology, the above embodiments may be applied to more complicated image processing and rendering techniques, such as including 3D renderings, 3D movie creation, and multi-scale image optimization for example. It is expected that the processors used in mobile devices will eventually have sufficient speed and memory to be capable of quickly performing the image processing steps discussed above. Therefore, embodiment encompassed within the scope of the claims includes conducting all image processing on the handheld device itself. This is because when the mobile device has sufficient processor capability it will be advantageous to perform most or all of the image processing within the device to reduce the amount of data that must be transmitted back and forth between the mobile device and the external server. Moving the image processing back into the mobile device may also result in faster image display and better utilization of the handheld device capabilities.

On the other hand, if data connectivity speeds improve to become faster than the processor speeds and capabilities of handheld devices, as is currently the trend with the introduction of 3rd generation (3G) networks, complete image frames optimized for the handheld device could be collated on the server or other remote processor and made available for download via the faster data communication network.

Image processing algorithms may include defining one or more custom transform functions for each modality that defines various aspects of the original data file. Such a format interchange driver located in an external processor, such as the console 120, the data server, or in the medical device acquiring the data 150, may use data files or convert the data into one or more other formats to allow easier transformation. Similar techniques may be used to transform data received from the handheld device 150 back into the original image format for populating medical records or reconciling data received from the mobile device 150 with data in the medical records.

Multiple variants of data format may be expected from multiple vendors of medical devices, including medical imaging equipment, even though efforts to harmonize medical data formats are ongoing. To address this challenge, the system may be customized upon installation to use the communication links that work with the particular devices installed in the hospital network. The various embodiments are not tied to a particular data format or communication protocol, enabling the system to be customized to the data formats and network protocols of each installation. Alternatively, a data format and communication protocol translator module or server may be included within the system to convert data files and communications protocols to a common format and protocol.

Figure 4:
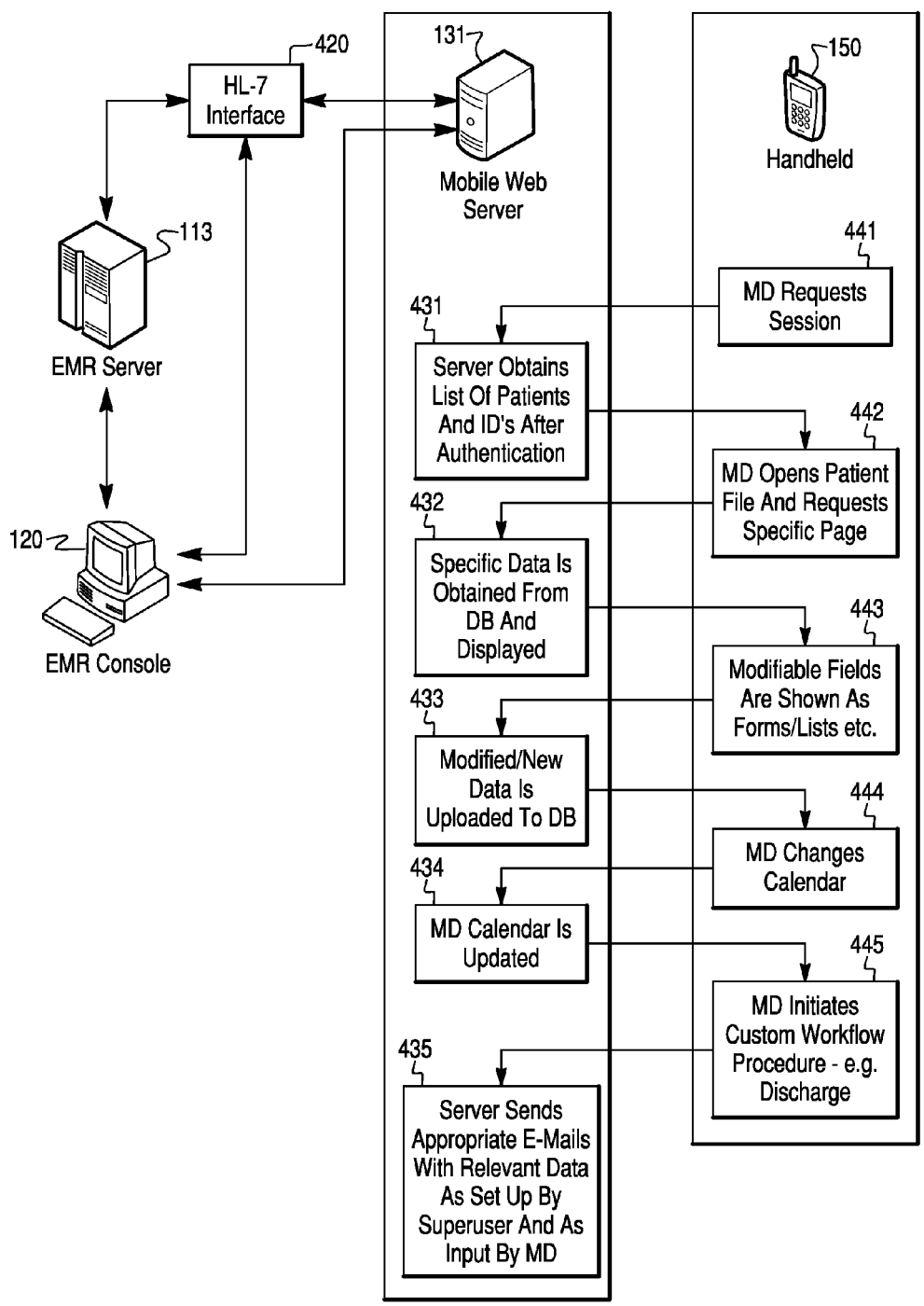
FIG. 4 is a system illustration and flow diagram of a method for communication medical information according to an embodiment.

In an exemplary embodiment illustrated in FIG. 4, Electronic Medical Records (EMR) system can be accessed in order to deliver patient medical records to a physician's handheld device. An EMR system primarily comprises text data that includes various standard data fields which record the details of the patient's identity, basic demographic information (age, sex, height, weight, ethnicity, etc.,), patient-physician interactions, diagnoses, prescriptions, treatment plans, etc. Thus, when a physician is reviewing a patient's current data, such as an ECG or diagnostic image, the physician may also need to access the patient's medical records, including information beyond what the console operator may have included in a consultation request message. In other instances, the physician may need to review background data stored in an EMR system while, for example, performing rounds at one or more hospitals which he visits.

In the embodiment illustrated in FIG. 4, a data server 131 is configured, such as by connection to a hospital's wired and/or wireless network, so that it can communicate with an EMR server 113 or an EMR console 120. The EMR server 113 and console 120 may be physically or functionally integrated into the same equipment, such as a workstation with a large memory that is configured as a server and coupled to the hospital's network. An EMR database typically will contain medical data pertaining to multiple specialties and sub-specialties. The data server 131 may be configured to interface with EMR databases employing different data formats by including the necessary translation capabilities to receive data from the EMR database and translate the data into a format that can be transmitted to and displayed by a mobile device 150.

Referring to FIG. 4, the data server 131 also may be configured to allow mobile devices 150 to access, such as upon a physician's request via the mobile device 150, step 441, summaries of medical data, such as patient lists, step 431. When a list of patients is accessed, the physician may select a particular patient and a particular page or section of the medical records, step 442. Medical data of a patient may then be accessed. This medical data may be further sortable by, for example, a list of specialties involved, chronological list of patient visits, or even by major findings. The physician may then select an event or a file to view, step 442. The data server 131 may then search through the patient file and generate a summary of the patient's records pertaining to a particular visit, complaint, or specialty, and format this data for transmission to the mobile device, step 432. The data to be sent to the mobile device 150 may be customized and formatted on the data server 131 to match the display characteristics of the mobile device 150. The mobile device 150 receives and displays the transmitted data, such as single or multiple pages of summarized data, step 443. In an embodiment, the data may be displayed in a keyword format so that the physician may quickly grasp the data of most interest, or click on specific key words to view a detailed listing of the related underlying patient-physician interaction record. The physician may then update the current data record or create a new one, perhaps with new observations or a new treatment plan, step 443, which may then be uploaded back to the EMR server, step 433.

EMR systems often include or are integrated with physicians' electronic calendars and appointment schedulers. Oftentimes, physicians must add appointments or change their schedules. The data server 131 can be coupled to the physician's calendar in the EMR system so that the calendar can be viewed and modified on the physician's mobile device 150. In this embodiment, physicians may access their calendar or make a change to their calendar using their mobile device 150, step 444. The physician may also be able to make changes to the calendar. As with other communications, data summarizing the calendar change is transmitted the data server 131 by the mobile device using a cellular telephone network. Depending upon the implementation and the sensitivity of the calendar change, such data may be encrypted or unencrypted during the transmission. The data server 131 receives and recognizes the calendar changes and sends information to the EMR server 113 to update the calendar, step 434. The calendar update may then be reflected on the EMR system or the related physician or general office calendar based upon the type of entry in the calendar and depending upon the EMR and calendar systems implemented at the hospital.

This embodiment may also be useful when physicians need to review patient medical charts prior to rendering an opinion or issuing an order from a remote location. For example, if the physician is being consulted concerning a patient discharge, the physician may need to review the patient's medical chart prior to agreeing to the discharge. The embodiment may also assist physicians in making follow-up appointments for patients who require continued medical care. For example, patients being discharged after a surgery in which an Implantable Cardioverted-Defibrillator (ICD) device was implanted in their chests will require follow-up appointments for re-evaluation of their condition and to confirm the proper functioning of the ICD device. In such instances, follow-up appointments and custom workflow procedures for the patient may be created by physicians remotely by entering the appropriate information into their handheld device 150, step 445. The data server 131 receives the data from the handheld device 150 via cellular telephone or other wireless data networks, and send the appropriate messages (e.g., in the form of an e-mail with attachments) to the appropriate individuals and functions, including for example the EMR server 113, step 435. Appointment may be automatically generated in the physician's calendar or an electronic reminder may be sent from the physician's mobile device to his office personnel to schedule an appointment.

This embodiment may include software tools operating on the handheld device 150 and/or the data server 131 to facilitate the physician's tasks when the situation requires multiple actions as well as establishing multiple follow-up events or appointments. For example, the discharge of a pre-term birth patient may require a neonatologist referral, a pediatrics appointment, an obstetrics/gynecology office appointment, etc. Software decision tools can aid the physician by presenting electronic fillable forms on the handheld device's screen that remind the physician of all actions, orders and events appropriate for the particular medical activity being addressed. For example, the handheld device may present a form in which the physician first selects from a menu the type of situation being addressed. If the situation involves discharge of a pre-term birth, the electronic fillable form presented on the device may then present fillable blanks for neonatologist referrals, pediatric appointment creation, etc. Such blanks may be filled by the physician using the keyboard entry or by selecting entries from drop down menus, for example.

Figure 5:
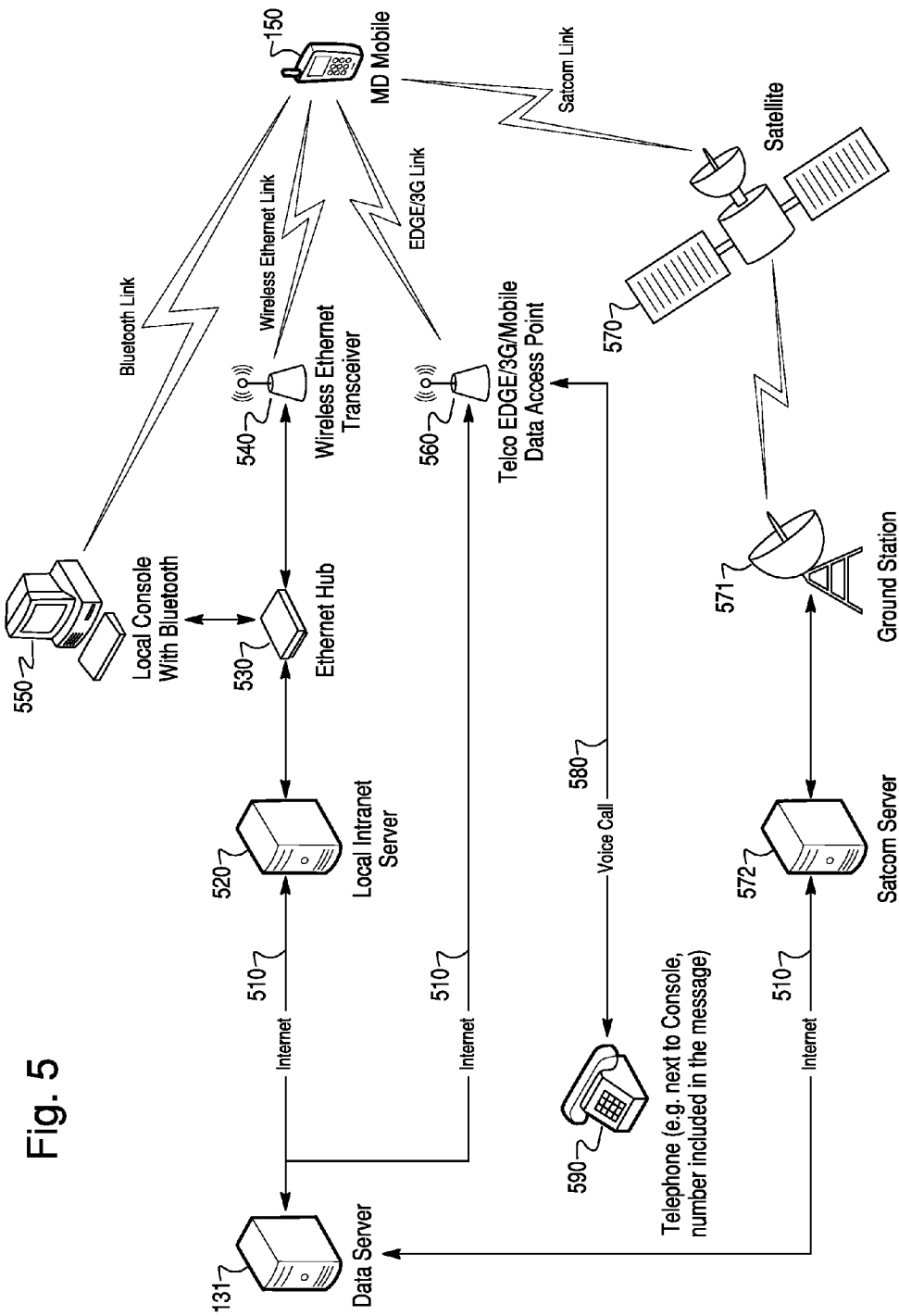
FIG. 5 is an illustration of alternatives modes of communication between databases, servers, and a handheld device according to an embodiment.

In communicating medical information to mobile devices, the mobile device 150 may communicate with the data server 131 in multiple ways, including ways other than using a cellular network. Some modern mobile devices are capable of switching between Bluetooth, WiFi, and different cell phone carriers and networks depending upon signal availability. FIG. 5 illustrates the various communication systems that may be used by the various embodiments in order to communicate medical information to/from mobile devices 150, dependably and reliably, regardless of the physician's location.

The software operating in mobile devices 150 may be configured to analyze the available communication networks based on their signal strength and other factors, including their security, cost, speed, reliability and signal stability, and switch their communication mode for accessing the data server 131, accordingly. The types of wireless data communication systems 560 that may be used include: the cell phone networks operated by cellular telephone service providers, such as EDGE, 3G, CDMA, GPRS, and GSM networks 560; any of a variety of Wireless Ethernet networks 540 that are being implemented within buildings, airports, hospitals, and commercial establishments, such as WiFi, or IEEE 802.11B, G, or N; 540; and Bluetooth links that may be established with a local console 550. Additionally, some physicians may be equipped with a satellite telephone, such as an Iridium handset, so that data may also be communicated via a satellite communication link via a satellite 570. Of course, the physician's mobile device 150 may receive calls from conventional telephones 590, such as a telephone positioned next to or within a hospital console 120.

In the normal case of data communications via cellular telephone networks, the message data will travel wirelessly between the mobile device 150 and the nearest cell tower 560. The cell tower may be connected via wired or wireless networks reaching back to a network center which may transmit the data via conventional telephone lines. The data message may then be transmitted to the data server 131 via the Internet 510 through an Internet server (not separately shown) that is located near or remote from the cell tower, depending upon the service provider's network set up.

In the case of a WiFi type wireless data transmission, the mobile device 150 establishes a wireless communication link with a WiFi transceiver 540. Typically, the wireless transceiver 540 is coupled to a local Internet server 520 which is connected to the Internet 510. In some installations, the WiFi transceiver 540 may be connected to the Internet server 520 by way of an Ethernet via an Ethernet hub 530. To send a message to the mobile device 150, the data server 131 sends the message via the Internet to the local internet server 520 which transmits the message from the WiFi transceiver 540.

A Bluetooth wireless connection may be convenient for physicians working inside an office near a local console but shielded from cellular telephone or WiFi networks. Although a Bluetooth wireless data link may not provide access to the Internet by itself, software on the physician's mobile device 150 may be configured to allow the device to communicate with the data server 131 via the local console 550 provided the console with the Bluetooth 550 linkage is connected either directly or indirectly to the Internet, such as through an Ethernet router 530, a local intranet server 520, and the Internet 510.

A satellite data link may be the only form of communication available when a physician travels to remote locations on the globe. For example, a physician participating in Doctors Without Boarders may be practicing medicine in Sub-Saharan Africa one day and in Indonesia the next. Yet the full benefits of the various embodiments may be provided to such physicians using satellite communication links, allowing them to be available for consultations and use the full resources of the hospital electronic medical system regardless of their location. In such circumstances, data sent from the data server 131 may be sent via the Internet 510 to a SATCOM server 572 within the satellite service provider. The SATCOM server 572 receives the message and reformats it for transmission via satellite. The message is then sent via a ground station antenna 571 up to the communication satellite 570 which relays the data down to the physician's mobile device 150. Communication from the physician to the data server 131 travels in a reverse path.

Figure 6:
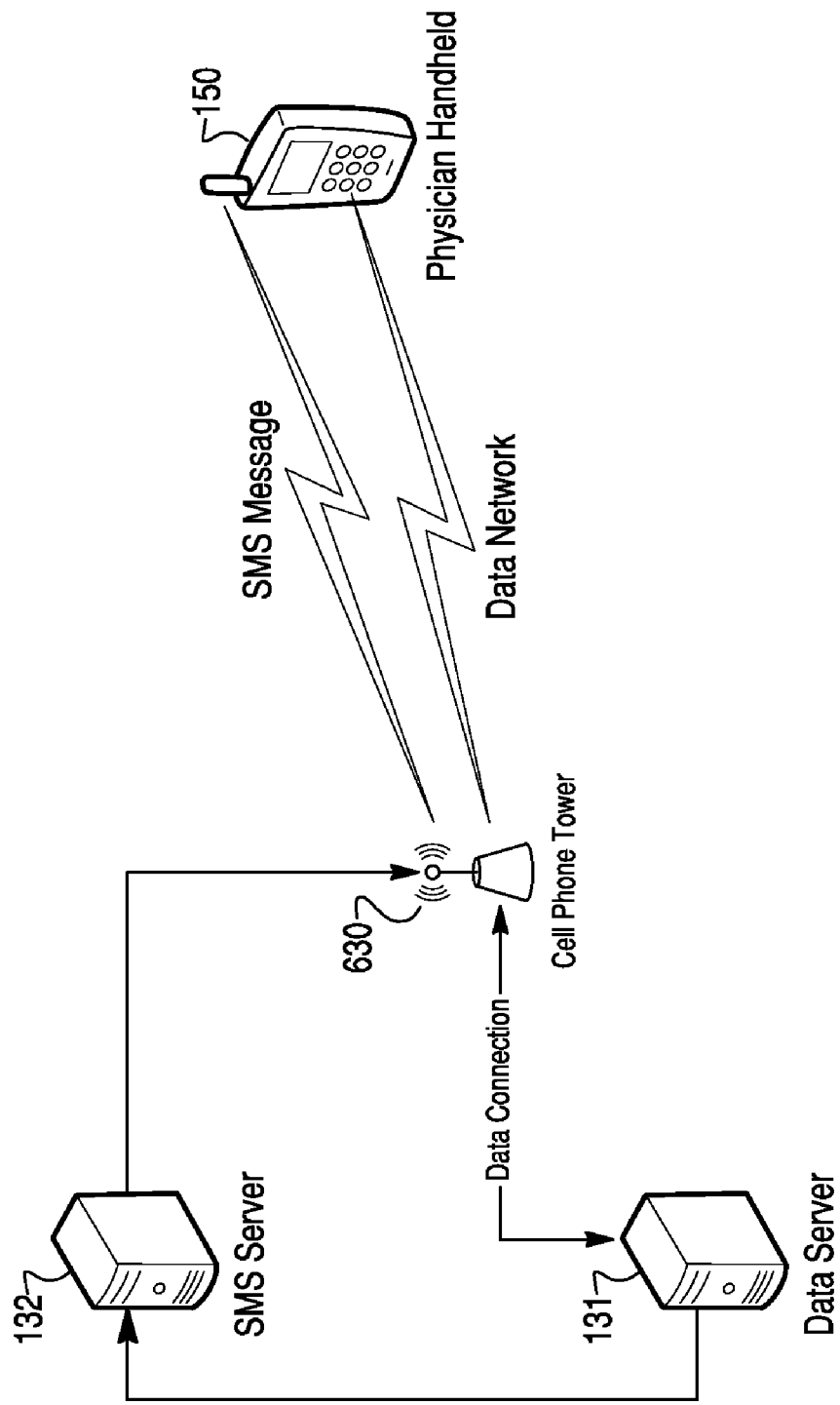
FIG. 6 is an illustration of data communication between servers, and a handheld device

Since in many cases communications with physicians via their handheld devices 150 will involve urgent matters, it is important to maximize the reliability of message communication. In an embodiment illustrated in FIG. 6, message may be sent via two redundant wireless techniques in order to increase the likelihood of successful delivery on the first attempt. In this embodiment, the same or similar message may be sent using the cellular telephone system's SMS messaging system and data network or electronic mail message system. This may be accomplished by sending the same or similar messages using both the data server 131 and the SMS server 132 nearly simultaneously. Software in the handheld device 150 may then be configured to recognize redundant messages when both are received, so the physician is only notified once for each message sent. The handheld device 150 may also be configured with software to send back acknowledgement messages when an SMS or data/e-mail message has been received. Reception of an acknowledgement message by either the SMS server 132 or data server 131 will provide feedback to the system regarding the availability and timeliness of the two networks so that subsequent messages may be sent over the more reliable link. In another embodiment, a preferred methodology for delivery may be employed, such as HTML polling through the data network. If the server then detects that the message is not deliverable to the handheld, it can automatically switch the mode of delivery such as, for example, to SMS messaging. This logic can then be further extended for delivery through e-mail in case an acknowledgement message is not received acknowledging receipt of the sent SMS message.

Figure 7:
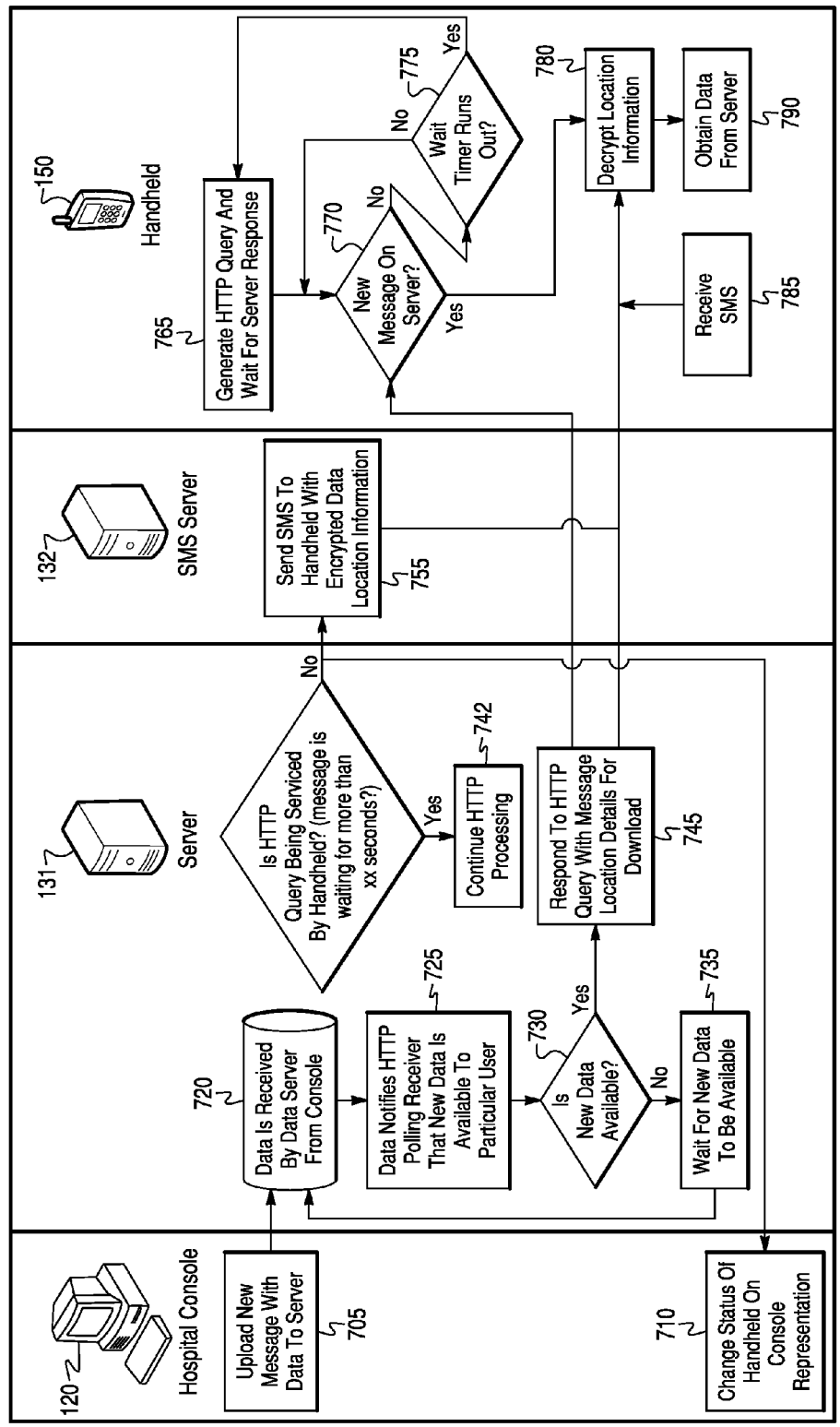
FIG. 7 is a flow diagram of a method for delivering data to a handheld device according to an embodiment.

FIG. 7 illustrates an embodiment of software methods that may be used to deliver messages and medical data from a hospital console 120 to the physician's handheld device 150 via a data server 131 and SMS server 132. As with other embodiments, the user on a console may upload a message for delivery to the physician handheld device, step 705. This data is received by the data server 131, step 720, which notifies an HTML polling receiver that new data is available for transmission to the physician, 725. If new data is available for transmission, 730, the data server 131 sends the data as an HTML message that includes the location for downloading an attachment or additional message details, 745. The data server 131 may then perform a loop waiting for new data for transmission, 735. If the physician's handheld device is not accepting HTML data transmissions, such as may be determined by failure of the handheld device to request an HTML download within a certain amount of time, the data server may send a notification of available data instead by an SMS message, 740. To send the notification via an SMS message, the content of the notification, which can be an encrypted or coded string of alphanumeric text which on decoding allows the handheld device to download specific message data, is transferred to the SMS server 132 which forwards the message via cellular telephone SMS systems, 755.

The console 120 uploads a new message and any data to the server 131, step 705. Data is received by the server 131, step 720. The server then notifies a HTTP polling response section of its software that a new message has been received, step 725. Software operating on the handheld device 150 sends a HTTP query to the server, 770. The server 131 responds to the query if new data is available, steps 730, 745. This or a separate follow up response contains the server memory (or IP address) location of the message and any data to the handheld device. This location information, is decoded if it is in encrypted format or compressed format, and processed on the handheld 150, step 780. Using this location information, the handheld device then requests and receives a download of the new data from the location on the server, step 790.

If no new data is available on the server 131, the HTTP polling response section does not respond to the HTTP polling from the handheld device, but instead just waits for any new data to be uploaded to the server 131 by the console 120, step 735. When no response is received from the HTTP poll by the handheld device in a predetermined time period, step 775, the handheld device closes the current HTTP request and opens a new HTTP request, step 765, immediately thereafter or after a predetermined time delay. This cycle of requesting a HTTP response and starting a new request if no response is received may be continued until new data is available on the server 131.

This continuous HTTP polling process also alerts the server 131 of the availability of the handheld device 150 for sending and receiving data. In instances where a HTTP polling is not received by the server 131 for a predefined time period, step 740, the server can assume that the handheld device is not available or easily reachable through the cell phone data network. The server 131 may then notify the handheld device of any new messages destined for that particular handheld device using an SMS message through the SMS server 132, step 755. The server 131 may also update the status on the console 120 of the corresponding physician as being unavailable, step 710, if either HTTP polling has been absent for a predefined extended period of time, or if the SMS message, step 755, does not result in a data download, step 790, by the handheld device in a predetermined time period. The SMS message sent by the SMS server 132, step 755, may be decoded by the handheld device 150 which may then download the message from the server 131.

Figure 8:
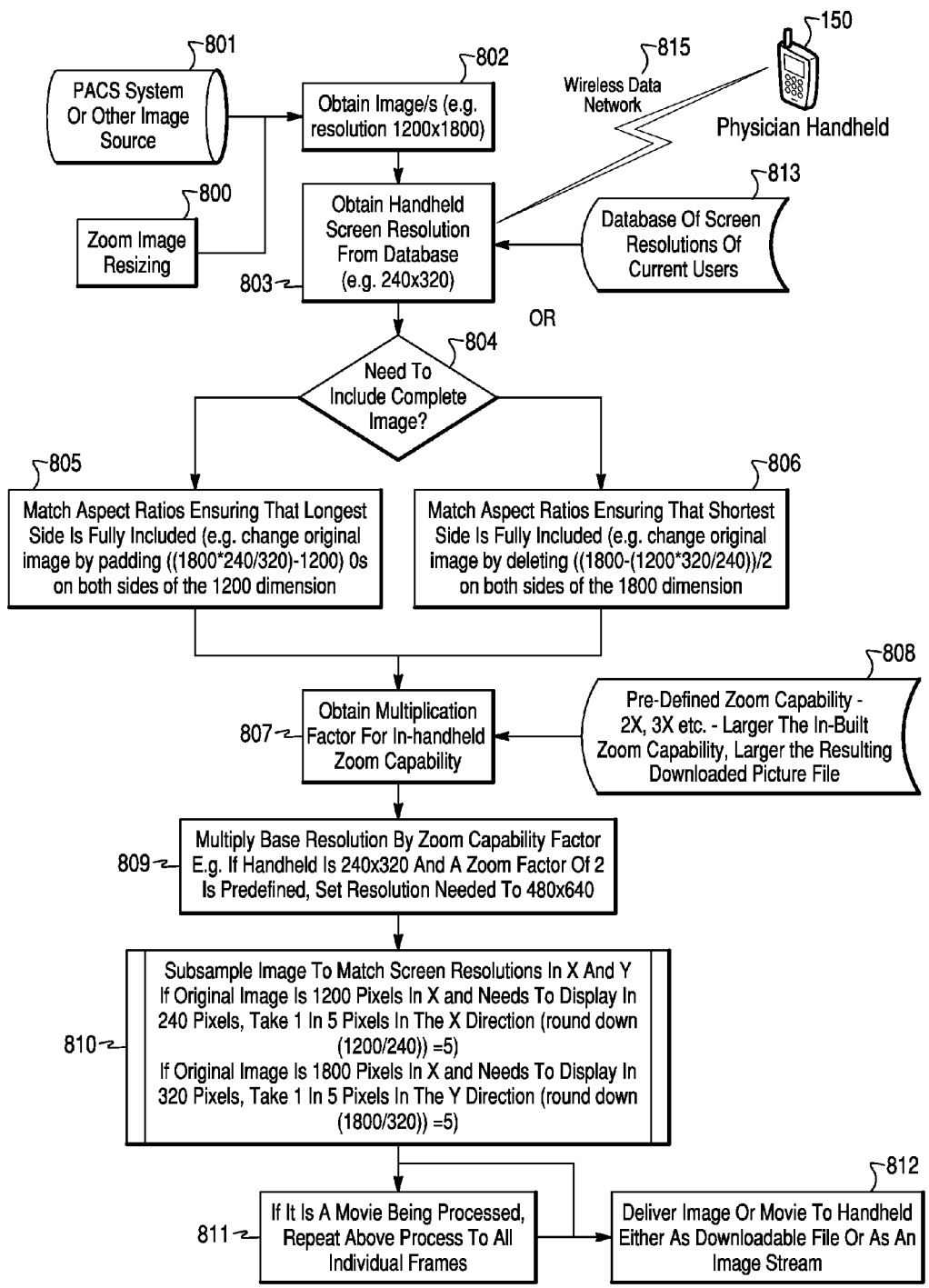
FIG. 8 is a flow diagram of a method for optimizing image format for display on a handheld device according to an embodiment.

FIG. 8 illustrates detail steps of methods for transmitting medical images to a physician's handheld device 150 according to various embodiments. The data server 131 and or the console 120 may perform a number of illustrated processing steps prior to transmitting image data to a physician's handheld device 150. In a typical process, image data may be received from a PACS system or other image source, 801. Additionally, information may be received from the handheld device 150 regarding image sizing or selection, 800. The data server 131 obtains the image from the console 120 and determines its size and resolution, 802. The console 120 may send the images directly from its memory, or may direct the server 131 to directly access the hospital database or other image source 801. Also, the data server 131 obtains the screen resolution and size of the physician's handheld device, 803. This information may be obtained from a database of handheld devices assigned to current users, 813. This could also be achieved by the server 131 querying the software on the physician's handheld device. If the image to be transmitted will be the complete image, 804, then the longest side of the image is matched to the dimensions of the handheld device screen, 805 and the shorter side adjusted based on the aspect ratio of the handheld screen. On the other hand, if the image to be transmitted is a portion of the complete image, 804, then the data server matches the shortest side of the selected portion of the image to the shortest side of the handheld screen, and adjusts the longer side according to the aspect ratio of the handheld screen, 806. With any display of a given resolution and a given image with a defined pixel density, a maximum zoom may be defined beyond which the image is either not recognizable, or the data presented in a clinical environment is not useful. Further, as selected by the handheld user, and also as may be dictated by the quality of the data network connection to the handheld device, a zoom factor may be determined which optimizes the number of extra pixels per pixel of display delivered to the handheld device. For instance, if the handheld display has a resolution of 200 pixels by 200 pixels, the data connection is very good, and the user chooses to have a 2× zoom capability on the handheld, the server may deliver an image of 400 pixels by 400 pixels. The data server then determines or obtains the multiplication factor for the handheld zoom capability, 807. The zoom preference of the user of the handheld device may be stored in a database file that may be accessed, 808. The larger the preferred zoom capability of the handheld device, the larger the image file that should be transmitted to enable that in-device zoom capability. With this information, the data server 131 then multiplies the base resolution by the zoom capability factor, 809 and sub-samples the image to match the screen resolutions in both dimensions, 810. For example, if the original image includes 1200 pixels in the X dimension and needs to be resized to display 240 pixels in the X dimension, the server software will select one out of every five pixels in the X dimension. Similarly, if the original image has 1800 pixels in the Y dimension and needs to be resized to 320 pixels, the server software will select one in every five pixels in the Y dimension. Once the image processing has been completed, the processed image is delivered to the handheld device as either a downloadable file or an image file delivered directly to the handheld device, 812.

While the embodiment method illustrated in FIG. 8 is described above as transpiring on the server 131, the embodiment method may alternatively performed on the console 120 in a substantially similar manner. In a further embodiment, the embodiment method may be performed on a processor connected or integral to the medical imaging system that is the source of the medical images (e.g., CT scanner, ultrasound imaging system, EKG system, etc.). To implement the embodiment method on either the server 131 or directly on the medical imaging system computer software configured to accomplish the method can be loaded onto or integrated into the functional software stored on the server 131 or medical imaging system.

If the image file to be transmitted is a movie (i.e., a series of images to be viewed sequentially), the preceding process may be repeated for all of the individual frames, 811. Once the processing of all the frames has been completed, the movie file is delivered to the handheld device as a downloadable file or as an image stream, 812.

Communicating medical data from the field to a medical facility and receiving physician consultations in the field may also be important. In some cases, a patient may be suffering from a condition that is too critical to wait for transportation to a hospital before treatment begins. Also, because ambulances travel on roads, their arrival at the hospital may be delayed by traffic. In such instances, a critically ill patient may benefit from prompt treatment advice of a specialist physician delivered to a location remote from the hospital. Such advice may be provided quicker using the various embodiments if the physician does not happen to be in the hospital at the time. Using the various embodiments, the physician can review the patient's medical data and records remotely and guide the field emergency personnel on proper treatments for the patient. This capability may also be important when immediate attention to a patient is necessary in an air-ambulance. For example, in the case of a heart disease patient, communicating ECG records directly to a cardiologist can review and provide his findings may save the patient's life.

Figure 9:
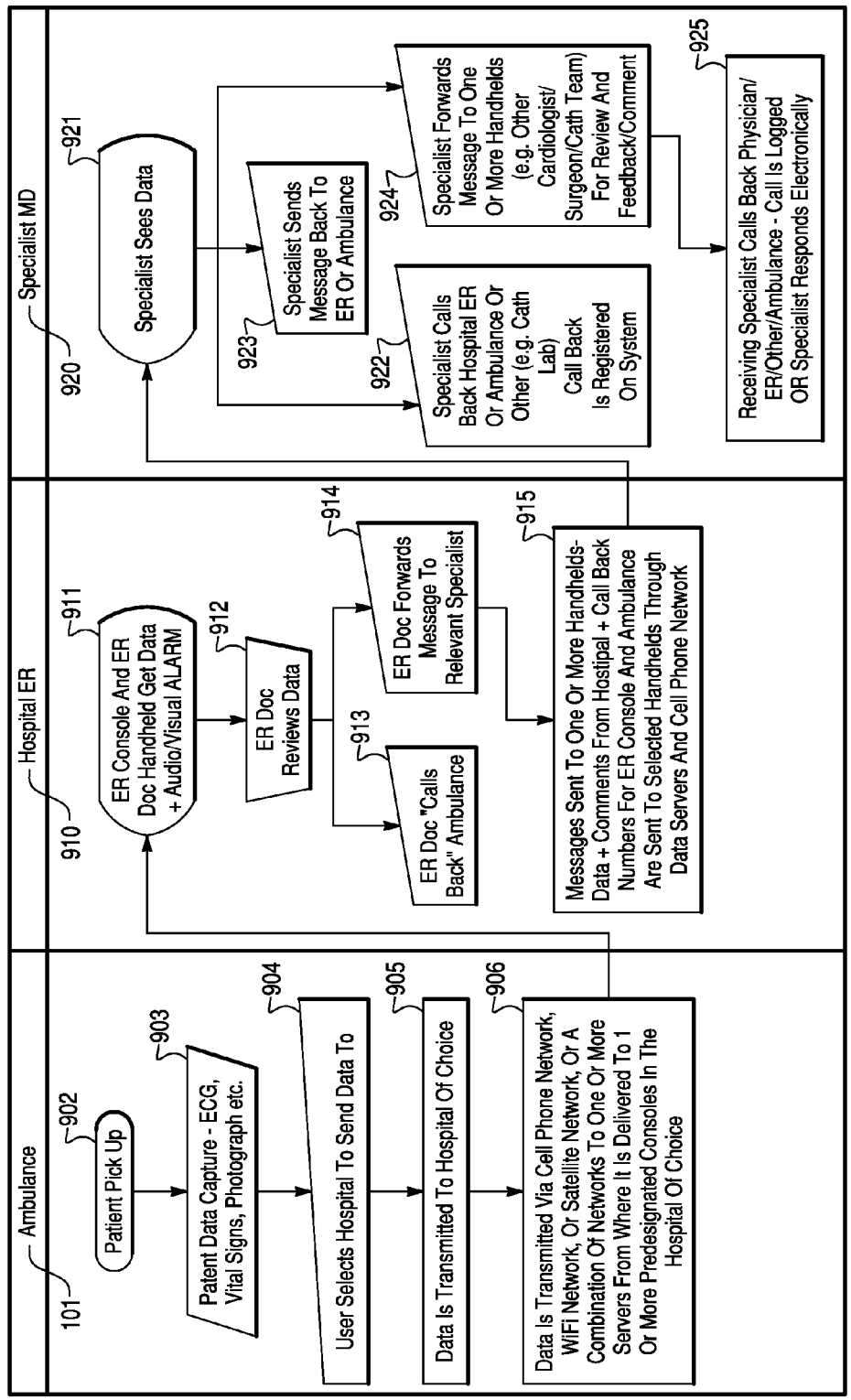
FIG. 9 is a flow diagram of a method for transmitting medical information from an ambulance to a physician's handheld device according to an embodiment.

In an exemplary embodiment illustrated in FIG. 9, medical data collected in the field may be transmitted to a medical facility before the arrival of the field emergency personnel. For example, when emergency personnel arrive at a chest pain patient's location they may first conduct an initial evaluation and then load the patient onto the ambulance for transportation, step 902. Using medical devices in the ambulance 101, such as an ECG machine, the emergency personnel may monitor and record the patient's vital signs, ECG and obtain other medical data, step 903. Once such data is collected, the emergency personnel may transmit the data to the destined medical facility using wireless networks, steps 904 and 905. This data may also be transmitted to the medical facility automatically from individual medical devices in the ambulance using wireless and wired networking technologies built into the equipment or the ambulance. Such medical data may be transmitted to one or more designated data servers and then to one or more designated medical facility consoles, or directly to one or more designated medical facility consoles, using any available wireless and wired network, including, for example, cellular telephone data networks, WiFi networks, satellite communication networks or combinations of such networks, step 906.

When the medical data is received at the hospital, that is in the hospital emergency room (ER) 910 an alarm may be presented on the Emergency Room (ER) console or an ER physician's mobile device, 911. The data may carry with it information regarding the criticality of the medical data being transmitted so the appropriate audio/visual alarm may be generated to inform the hospital staff of the nature and urgency of the medical emergency. The ER physician may review the transmitted medical data on the ER console or the physician's handheld device, 912. The ER physician may then either call the ambulance to convey his assistance, step 913, such as buy using his handheld device, or create and send a message to another specialist physician for additional consult using the ER console or the physician's handheld device, step 914. When an additional consult is requested, the consult request message created by the ER physician is transmitted to one or more physician mobile devices using one or more of the embodiments described herein, step 915.

When a physician consult is requested, the transmitted medical data will then be available to the contacted specialist physician 920 on his/her mobile device, step 921. In response, the specialist physician may then call the ER, the ambulance or other hospital facilities (e.g., the cardiac catheterization lab) using the handheld device, 922. When a call is made in response to a consultation request transmitted do the handheld device, the call back may be registered on the system, such as in the EMR system. Instead of calling, the consulting physician may create a message including his comments, orders for treatment plan, step 923. Alternatively, the physician may contact other specialists, such as by forwarding the original consultation request message to the other specialists, for further consultation and feedback, step 924. The server 131 may also be set up such that in instances where the consulting physician is not available, or if a predesignated on-call specialist or physician exists, then the message is routed to the appropriate physician. Using the capabilities of the various embodiments, the other specialists may then either call the physician, the hospital or the ambulance, or create electronic messages including their own comments, orders for treatment plan, step 925. All communications and calls from the various specialists contacted through this system may be registered for record keeping or billing purposes.

The various connections of medical devices and mobile handheld devices to the Internet may be accomplished by one or more pathways depending upon local network configurations available at the time of communication. Also, data communications may be accomplished using any of a variety of different telecommunications technologies and systems that exist or will be developed in the future. For example, data, instructions, commands, information, signals, bits, symbols, and pixels may be represented by voltages, currents, electromagnetic waves, magnetic fields, optical waves or pulses in order to communicate the information over the wired or wireless network. Data communication may include transforming the data into packets with error correction techniques included for distribution over asynchronous or synchronous communication links as are well known in the art. Furthermore, the various illustrative devices, servers, modules, circuits, methods, and algorithms described herein may be implemented as electronic hardware, computer software, or combinations of both. Software for the methods and systems described herein may be stored on and reside in random access memory (RAM), flash memory, read only memory (ROM), electronically programmable read only memory (EPROM), erasable electronically programmable read only memory (EEPROM), hard disk drives, removable disks, CD-ROM, or any other form of computer readable storage medium known in the art that will be developed.

Typical operations of the above described system and components will now be described illustrating how medical diagnostic and patient information are transmitted to a physician via the physician's handheld device such as a cellular telephone with a liquid crystal or superior display. An operator, or a system processor, selects one or more relevant sections of clinical data on a console to be sent to the physician's cellular telephone. Typically, this will be data that requires the physician's review or data deemed relevant to diagnosing or treating a particular urgent condition. For example, in the case of a heart attack victim, an emergency medical technician in an ambulance may apply electrodes to the patient's chest and initiate an ECG. In this example, the relevant data is the ECG trace and the console is the ECG system within the ambulance.

Once the data is selected on the console, the clinically relevant data is uploaded to a server. In the case of a console (e.g., a diagnostic machine or workstation) this step may simply involve sending the data via an internal network or via the Internet. In the case of a console in an ambulance, the data may be transmitted by wireless data link, radio transmitter, cellular telephone, or any other wireless network available.

The server to which the data is sent is programmed with executable software to interpret the information and facilitate communications with the physician's cell phone. In particular, the server can send a message to the physician's cell phone notifying it of availability of the clinically significant data. This message may be in the form of an SMS text message, electronic mail or voice mail, or any other messaging technique available via the cellular network. Such a message may be sent with or without the contextual information regarding the data. In simplest form, the message may notify the physician that data is available for down loading from the server.

In response to the message from the server, the physician's cell phone contacts the server and requests transmission of the available data. This may be initiated automatically by the cell phone in response to the message, or upon prompting by the physician who may read the message and then initiate the download by pressing a menu button. In an embodiment, the cell phone initiates the data download by activating a hyperlink transmitted in the message from the server. Data downloading from the server to the handheld may be accomplished by any data transmission protocol and system available via the cellular telephone network or other wireless networks accessible by the handheld device.

As described above, the downloaded data may include medical images, photographic or streaming video images, diagnostic data (which may be streaming data such as an ECG trace), clinical data in text or tabular format, or patient record data. Displaying such data on the cell phone allows the physician to review the data anywhere and as soon as the data becomes available.

The physician is provided tools on the cell phone which allow him/her to assess the clinical data, annotate the patient's file, add opinions or notes to the reviewed data, order procedures, further tests, or treatments, and refer to others for consultation. Such tools may be in the form of menu options with button selections, touch screen menus and text entry via a keyboard on the cell phone.

The physician's notes, orders and/or requests (including requests for more data from the server) can then be uploaded to the server using any data transmission protocol and system available via the wireless network. The server then forwards the physician's notes, orders and/or requests to the appropriate network address. This address may be the point of data origination or other points in the hospital infrastructure. If the physician has requested additional data that is available on the server, such as display of another portion of a medical image, the server will prepare a data package in response and send it to the cell phone in a reply message as described above.

Since the display size and processing power of cell phones are limited (especially compared to networked computers and workstations used to view and analyze clinical information within the hospital infrastructure), various components of the system may be configured to only transmit the most relevant sections of patient data to the physician's cell phone. Such relevant sections of data may be automatically selected from data files by system servers, may be inputted manually by an operator (e.g., an ER nurse or an EMT in an ambulance), or acquired directly from a medical device, or from a database.

In an embodiment, the console is configured with software to perform processing on the medical data to reduce the amount of data that needs to be transmitted, increase the speed of data transmission, or reduce the amount of processing required on the handheld for download, preparation, and display of the data.

In an embodiment, the server is configured with software to perform processing on the medical data to reduce the amount of data that needs to be transmitted, increase the speed of data transmission, or reduce the amount of processing required on the handheld for download, preparation, and display of the data. This processing may include, for example, data compression on the received data.

Figure 10:
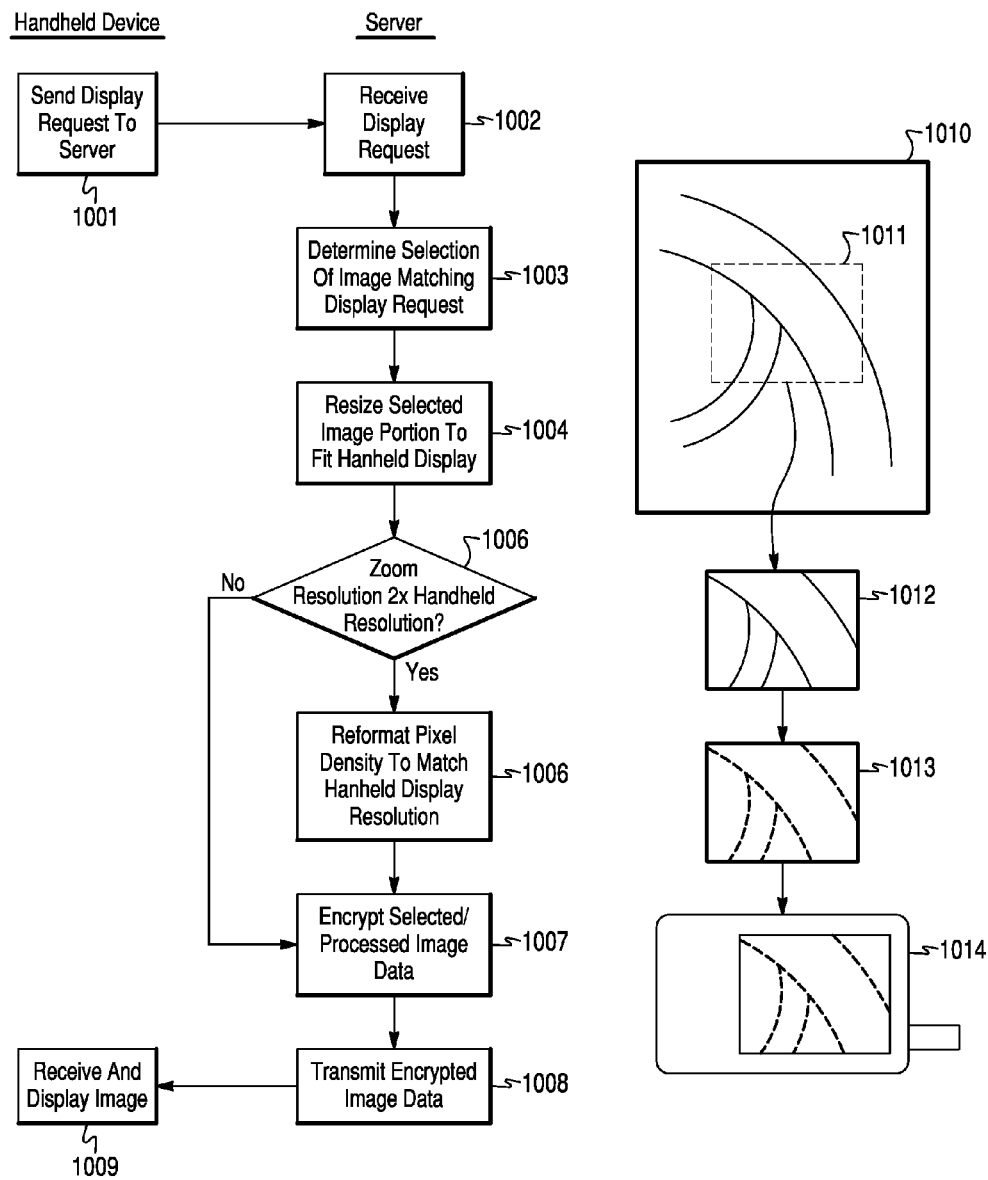
FIG. 10 is a flow diagram of a method for enabling image zoom-in and zoom-out capability on a handheld device according to an embodiment.

In an embodiment, the server performs image processing on the received data by sub-sampling the image to generate images for transmission that appropriately suit the handheld device's screen resolution. An embodiment of this process is illustrated in FIG. 10. This embodiment solves three problems associated with displaying medical images on a handheld device. First, a medical image 1010 can be quite large both in physical size and data content. Yet, only a small portion of the image may be of diagnostic significance to a physician. Second, a handheld device has a small screen and typically that screen has a low resolution compared to displays on workstations and personal computers that may be used to view medical images in the hospital setting. Third, a handheld device has limited processing power given its power, size, and environmental constraints, and therefore cannot manage and display large files effectively.

In overview, the method allows a user to select an image portion 1011 within the medical image 1010. This election may be by a pointer device, such as a mouse or light pen, used by an operator on a console or a stylus moving on a touch sensitive screen, such as implemented in Palm personal digital assistants. The selected image portion is copied into a new image file 1012 which is sized to fit the handheld device display. Next, the new image file 1012 is reformatted to match the pixel density of the handheld devices display resulting in a ready to display image file 1013. Finally, the ready to display image file 1013 is transmitted to the handheld device 1014 where it is displayed without significant additional processing.

In operation, a user may implement an image display request by indicating a portion of a displayed image using keystrokes, menu options, or a stylus dragged on a touch screen of the handheld device. In response, the handheld device will send a display request to the server using an available wireless data network, 1001. This request is received by the server via the wireless data network and supporting networks, 1002. Using the display request and the raw image data, the server then determines the portion of the image data which matches the display request, 1003. This may be accomplished by mapping the dimensions specified in the display request to the dimensions of the image data to determine the requested selection. Additionally, the server may consider the size of the handheld device display when determining the portion of the original image to be selected.

If the selected portion of the image is not the same size as the handheld device display, the server will resize the image to fit the dimensions of the display, 1004. This may be a simple graphic transformation or a more complex image resizing process. The result than is a selected portion of the display with a size that matches that of the handheld device display screen. Since most handheld devices have a lower resolution screen than the resolution of a regional image, the server may check for such a condition, 1005, and reformat the selected image to match the pixel density to the handheld display resolution, 1006. By performing this reformatting operation in the server, the system avoids overwhelming the processor of the handheld device and speeds up the image rendering process since the server processor is much faster than that of the handheld.

At this point the image is ready for transmission to the handheld device. In most applications, the server will encrypt the selected and processed image data prior to transmission, 1007. Finally, the server transmits the encrypted image data to the handheld device, 1008. This transmitted image is received by the handheld device where it is decrypted and displayed, 1009.

Figure 11:
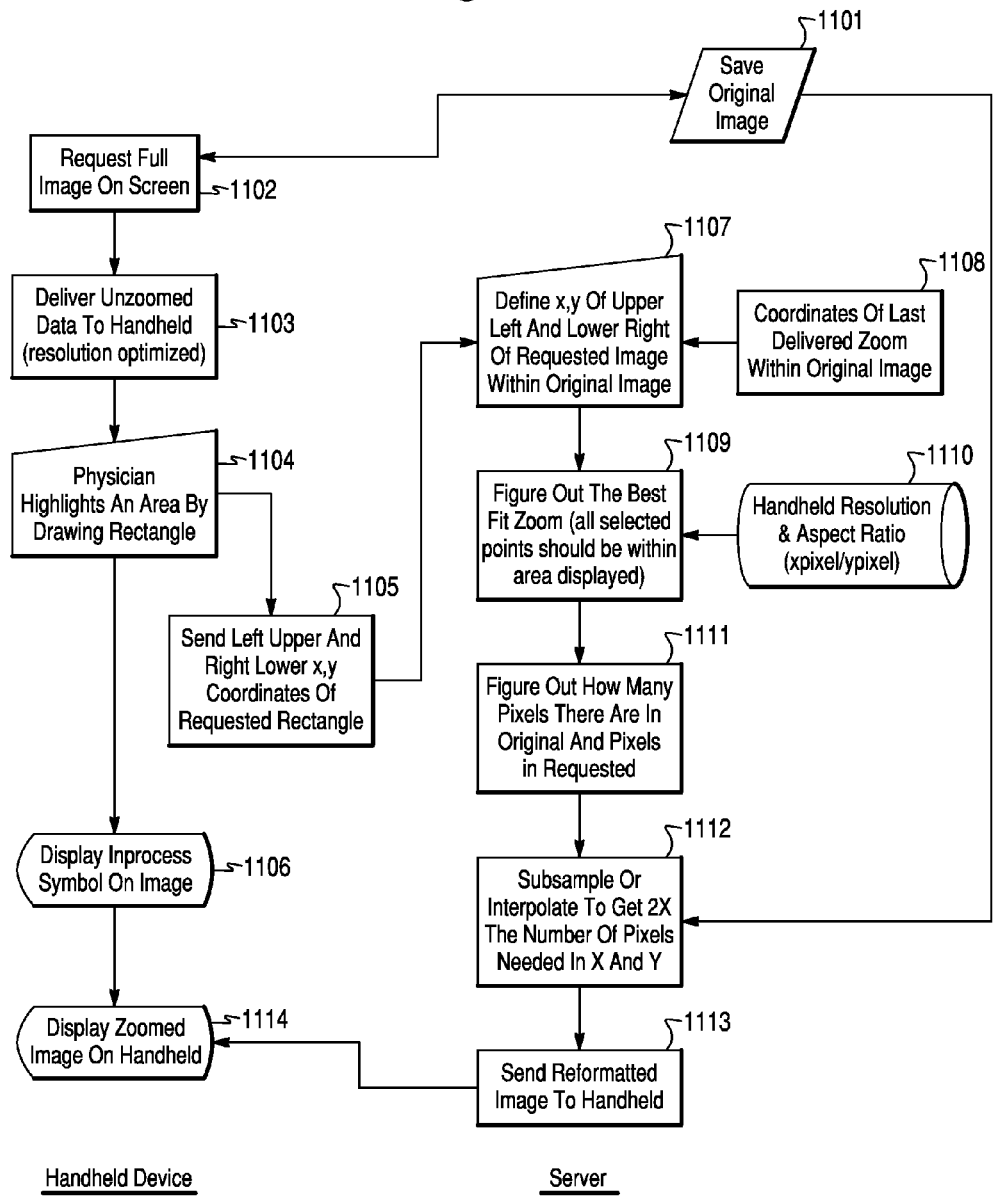
FIG. 11 is a flow diagram of an image processing method for enabling image zoom-in and zoom-out capability on a handheld device according to an embodiment.

Using this basic methodology, the handheld device and server can work together to provide the zoom capability to facilitate the physician's analysis of complex medical images. Referring to FIG. 11, a complex image may be loaded to the server for transmission to the handheld device by an operator at a hospital console, 1100. The loaded image is saved to the server, 1101. The availability of the image is also transmitted to the handheld device as previously explained, which can result in the device requesting download of the image, 1102. In response to this request, the server may deliver the entire image scaled in size and pixel density to match the handheld device resolution, 1103.

The physician may review the entire image on the handheld device and using keys, menu options or a stylus drawing on the device display, highlight an area of the image for closer inspection, 1104. In an example where the handheld device has a touch sensitive display screen, the physician may highlight the area for inspection by drawing a rectangle on the screen with a stylus. In another example, a rectangle or square, corresponding to the shape of the handheld display aspect ratio, may be generated around a region chosen by the handheld user. In response to an image portion selection by the physician, the handheld device may send an image selection request to the server, 1105. In an embodiment, this request may be in the form of coordinates on the image, such as the coordinates of the upper left corner and a lower right corner of the desired display rectangle. While waiting to receive a new image, the handheld device may display an in-process icon, symbol or image to let the physician know that the system is working on generating the requested display.

The server may also receive requests to process and transmit a selected zoomed image from an operator on a console. For example, a nurse at a console may determine that only a portion of a medical image will be of interest to the physician, such as may be the case of an X-ray of a limb where only the region containing a fracture is diagnostically significant. In this example, the nurse can select the portion of the image containing the fracture, such as by using a mouse or light pen, and direct the server to transmit the selected portion to the physician's handheld device. In a similar manner, others with access to the image or the server, such as an administrator or a supervisor with access to the server, may perform the image sub-selection operation.

Upon receiving the image request from the handheld device, the server correlates the parameters in the request to the original image file, 1107. This may be accomplished by mapping the received coordinates to the image dimensions. Such image requests will typically be made in a sequence of zoom-in requests as the physician drills down into the image to review particular details. Therefore, the server may make use of coordinates of previous image requests in order to correlate the new request against the original image, 1108.

Once the server has determined the portion of the original image to be displayed, it calculates the best fit of the selected image portion to the handheld device display, 1109. and doing so, the server may call from memory information regarding the handheld device's display size, aspect ratio and pixel density/resolution, 1110. Using this information, the server determines the number of pixels within the selected portion of the original image and the number of pixels that can be displayed on the handheld device, 1111. In an embodiment the server then sub-samples or interpolates the image data in order to obtain twice the number of pixels as needed to fill the handheld device display, 1112. In another embodiment, the server may sub-sample or interpolate the image data in order to obtain the same number of pixels as needed to fill the handheld device display. Finally, the server sends the reformatted image to the handheld device, 1113, which receives and displays the image, 1114.

This process of calculating a selected portion of the image and generating a display compatible with the handheld device display is used for panning motion as well as zooming. To pan, the user may press an arrow key or tap on a side of the display with a stylus, for example. The handheld device can calculate coordinates that corresponds to the next image frame to the left or right, up or down, depending upon the indicated motion of panning. These coordinates are transmitted to the server in an image request, after which the server processes the request in the above described manner in order to transmit the desired image portion to the handheld device.

In another embodiment, where a quicker response may be desired, the handheld displays the previous unzoomed image, and allows the handheld user to zoom in on another portion of the image, thus providing the same end result as panning, while enhancing the accuracy of this process.

Figure 12:
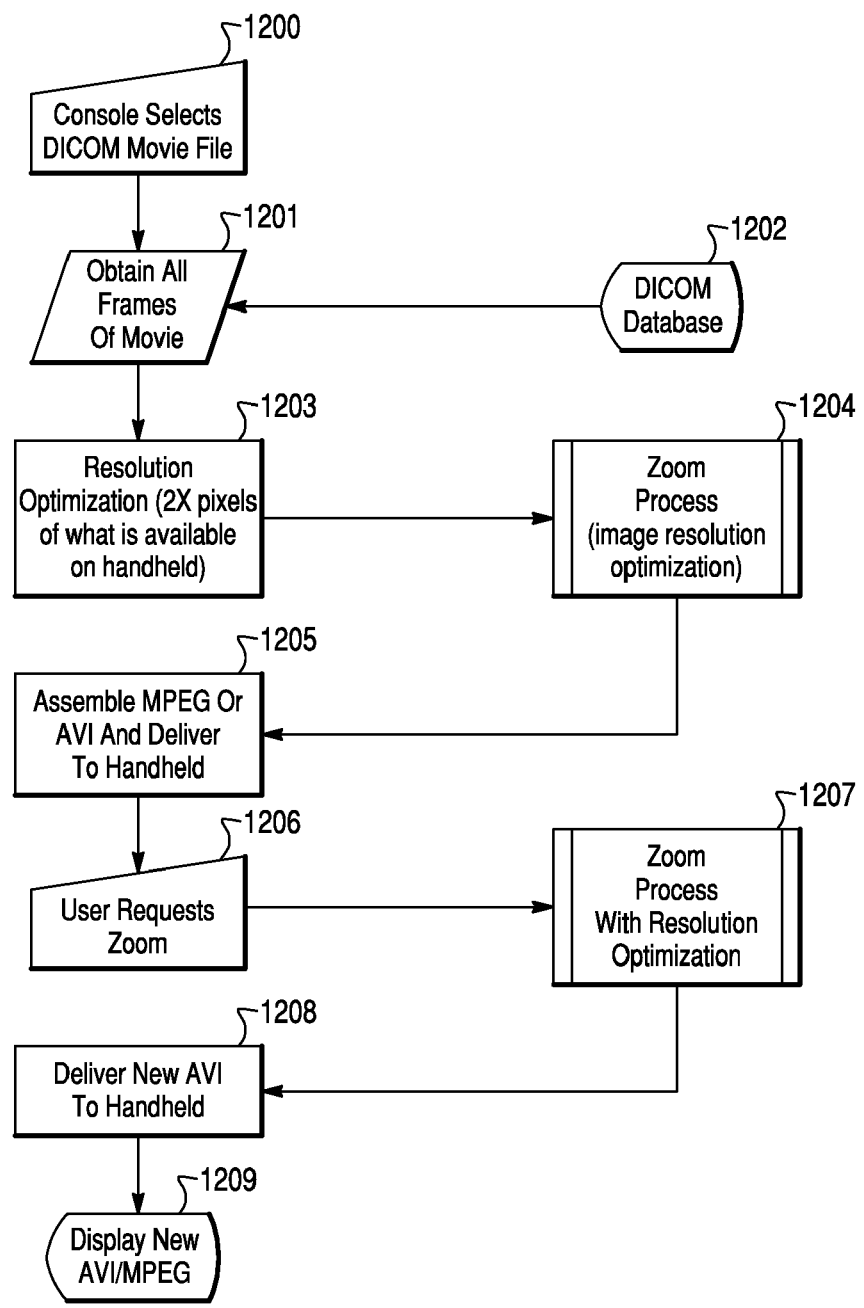
FIG. 12 is a flow diagram of image processing method for presenting moving images on a handheld device according to an embodiment.

Using similar processes, the server can transmit and the handheld device can display moving images as illustrated in FIG. 12. Examples of moving medical images include fluoroscopy, ultrasound images, ECG and EEG traces, and video images (e.g., video images of a victim or an injury). An operator on a hospital console may select a movie file (e.g., a DICOM image file) for transmission to a physician's handheld device, 1200. The console or server may then obtain all frames of the selected movie file from a database, 1201, 1202. Then for each Frame within the movie file, the server processes the image data to optimize it to the resolution of the handheld device display, 1203. For example, the server may sub-select pixels in order to create an image file with two times the number of pixels that will be displayed on the handheld device. If the handheld device has requested a display of a zoomed image (i.e., selected a portion of the movie file for display), the zoom image processing steps illustrated in FIG. 11 maybe performed, 1204. When each frame within the movie file has been reformatted to match the handheld device display, the processed frames are assembled into a single file, such as an MPEG or AVI file, and transmitted to the handheld device, 1205. The user may select a portion of the image for closer inspection, such as by using a stylus as described above, 1206. In that case, the zoom the process scribed above with reference to FIG. 11 is performed, 1207. The revised moving image file is then transmitted to the handheld device, 1208, which then displays the moving image, 1209.

The server may have the dimensions and display characteristics of the physician's handheld device stored in memory, such as recorded during initial installation, or obtain these upon the handheld device logging-in to the server, or at some other time. Alternatively, the server may receive such technical specifications as part of a display request from the handheld device. In another alternative, the server may send a message requesting the handheld device to send its display technical specifications. For example, the server may request the handheld device's display properties in response to receiving a display request. The display characteristics may include the number of pixels that can be displayed, the physical size of the screen, and the number of color bits of information that can be displayed.

In determining the optimal resolution for each image transmitted to the physician's handheld device, the server may use predictive algorithms, such as described herein.

In addition to generating resolution optimized images, the server may also perform three-dimensional renderings of three-dimensional data sets, thereby allowing the physician to view three-dimensional image data on his/her handheld device. Such renderings of three-dimensional image data may be in the form of rotatable two-dimensional slice images, or isometric renderings, or movies where the isometric rendering is rotated by a given angle frame to frame. As with the other image processing methods described above, the server firsts creates a rendering of the selected three-dimensional data and then reformats the rendering to match the size and resolution characteristics of the handheld device display. Using similar methods applied to each three-dimensional data set over a sequence in time, the server can generate a time-based sequence of three-dimensional renderings (which may be referred to as a four-dimensional rendering) for display on the handheld device. Similar techniques as previously described may be applied to allow the server to process and render the three dimensional data, with the control for the 3-D rendering and data management tools available on the handheld.

In an embodiment, the server may receive a real-time stream of clinical data, such as an ECG trace, or image data, such as an ultrasound image of a heart, and using methods similar to those described above with reference to FIGS. 10-12, process and transmit display-optimized images to the handheld device in near real time.

The transmission of moving image data to a handheld device, whether in real-time or from stored movie files, must overcome technical limitations that may vary from time to time and from device to device. For example, the transmission rate may be limited by the connection speed and bandwidth of a particular cellular telephone connection. As noted above, handheld devices may differ in their display size, resolution and refresh rate, as well as the devices processing speed, available memory and communication bandwidth. The connection speed and transmission bandwidth of a cellular telephone connection will depend upon the signal strength and interference which will vary from place to place, as well as the delivery techniques and processes utilized by the cell phone service provider. Also, these transmission characteristics are likely to change as the handheld device moves within and across cellular zones, as will occur if the user is in a moving vehicle. Transmitting images at too high a frame rate for either the handheld device or the available communication link will only generate transmission errors and provide no improvement in display. To accommodate such variability in transmission while providing a useful moving display of moving medical images, the server may implement a frame buffering method like that illustrated in FIG. 13. In this method, both the individual frames and rate at which frames are transmitted (the "frame rate") are optimized to match the handheld device's display characteristics and present connection speed.

Figure 13:
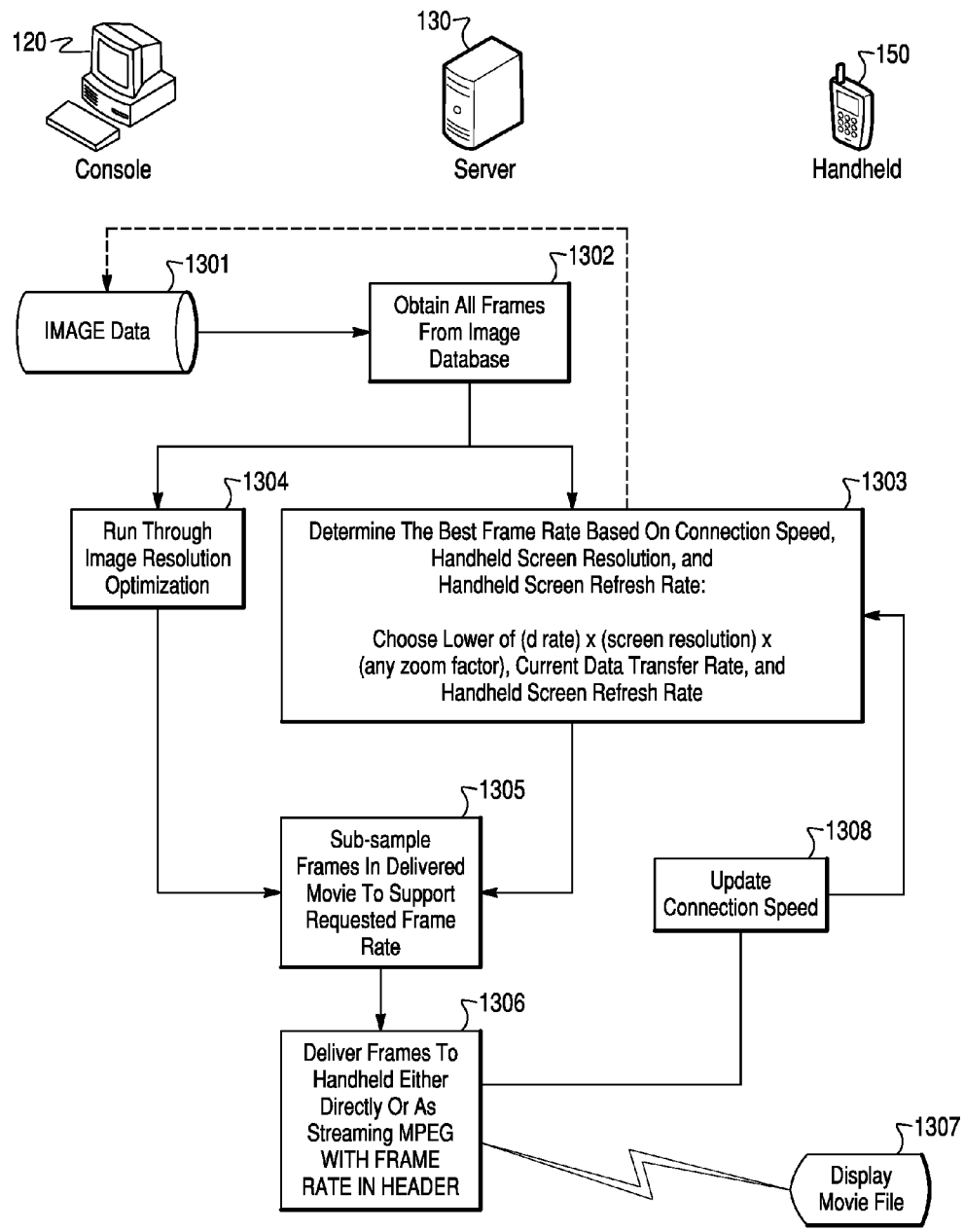
FIG. 13 is a flow diagram of a method for presenting moving images at a proper frame rate for presentation on a handheld device according to an embodiment.

Referring to FIG. 13, image data from a data file or from a real-time source are obtained by the server, 1302. In the case of a movie file in memory, all image frames may be obtained from memory and stored on the server for processing. In the case of a real-time data source, a group of frames may be selected at a time for processing with the rest buffered in memory. The server then performs the image resolution optimization methods described above with reference to FIGS. 10-12 to generate a sequence of optimized image frames, 1304.

Simultaneously, the server determines the best (or an acceptable) frame rate for transmission of images, 1303. This determination is based upon the communication connection speed and bandwidth, the handheld device display resolution, and the handheld device display refresh rate. In an example method, the server may determine the frame rate as the lowest of (a) the display resolution along with any zoom factor the user may have the facility to choose, and the desired display frame rate; i.e. the effective desired data rate, and (b) the actual data transfer rate available through the network to the handheld at that point in time. If MPEG compression of image frames is desired, the MPEG compression factor is considered in the frame rate determination also.

With the best frame rate determined, the server sub-samples the optimized image frames to select those to be delivered to the handheld device at the selected frame rate, 1305. This process may involve selecting a fraction of the frames for transmission, such as every other frame, every third frame, three out of every five frames, etc. Finally, the server delivers the selected frames to the handheld device as a single file or as a streaming file, 1306. In this transmission, the server will also inform the handheld device of the selected frame rate, such as in a message header or as a separate data element, so the handheld device can display the frames at the appropriate rate as a movie file or streaming video, 1307.

Since the data transmission rate of the communication link is likely to vary, the handheld device and the server may exchange information to enable the server to determine the current connection speed for use in determining the best frame rate, 1308. This may be accomplished by the handheld device periodically reporting back the number of lost bits or the error rate detected in received messages. Alternatively, the server may periodically send the handheld device a message containing information that allows the handheld device to determine the connection speed. In a third alternative, the server may send a message string of known length that the handheld device promptly resends back to the server allowing it to measure the transmission rate and the number of errors in the message. Other well known methods for determining data transmission speeds of a communication link may also be used.

In the case of a real-time data source, the process illustrated in FIG. 13 will continue to be performed on blocks of image frames buffered in the server in order to provide a near-real time, near-continuous stream of images at an optimized frame rate with optimized size and resolution. In order to accommodate changes in connection speed that may occur if the handheld device is moving within or between cell zones, the server and handheld device may periodically (such as every 10 seconds) exchange information on the connection speed so the server can update the connection speed and, if necessary or possible, change the best frame rate used to transmit images. For example, if the physician is initially located where there is low signal strength and/or high noise interference (in a "bad cell zone"), the real-time display may appear jumpy as the best frame rate may be lower than the display's refresh rate. Then as the physician moves to a location with better signal quality, the real-time display may appear smooth as the best frame rate increases, reaching a maximum at the display's refresh rate.

In an embodiment (illustrated by the dashed arrow in FIG. 13), the server may shift the sub-sampling function 1305 to the console, or even to the imaging unit providing the real-time data stream. In this embodiment, the server determines the best frame rate, 1303, such as by using the methods described above, and then sends the frame rate information to the console or imaging unit. The console or imaging unit then samples the real-time data stream to select data or image frames at the specified frame rate for transmission to the server. The server then performs image resolution optimization on the receive frames, 1304, and transmits them on to the handheld device, 1306.

In addition to accepting information from an operator, the console may be configured to accept commands from the operator to select, designate or access particular medical data for communication to the physician's cellular telephone. As an example, the console may include tools to allow the operator to view clinical data, dynamic data (e.g., an ECG trace) and image data (e.g., an X-ray or ultrasound image) and select (e.g., by using a light pen, pointing device (i.e., mouse) and/or keyboard) a portion for transmission to the physician. In another embodiment, the console software may be capable of receiving data requests from the server, based on which the console may query appropriate devices or databases and make available such data to the server.

In various embodiments, the console, server and handheld device are configured with software to monitor the delivery of messages, accommodate disruptions and delays in the delivery of messages, and keep an operator on a console updated on the status of messages. This functionality is important in many medical situations in which response time is critical, such as in the case of a patient potentially suffering a heart attack. Cellular telephone networks in certain geographical areas are notoriously unreliable and physicians may be in and out of cell phone contact. To address the criticality of reaching a physician using an unreliable network, the console, server and handheld device may repeat message transmissions periodically until a response is received. Also, if the physician is unavailable or fails to respond, the user on the console can be notified so another physician can be contacted. An example of such methods is illustrated in FIG. 14.

Figure 14:
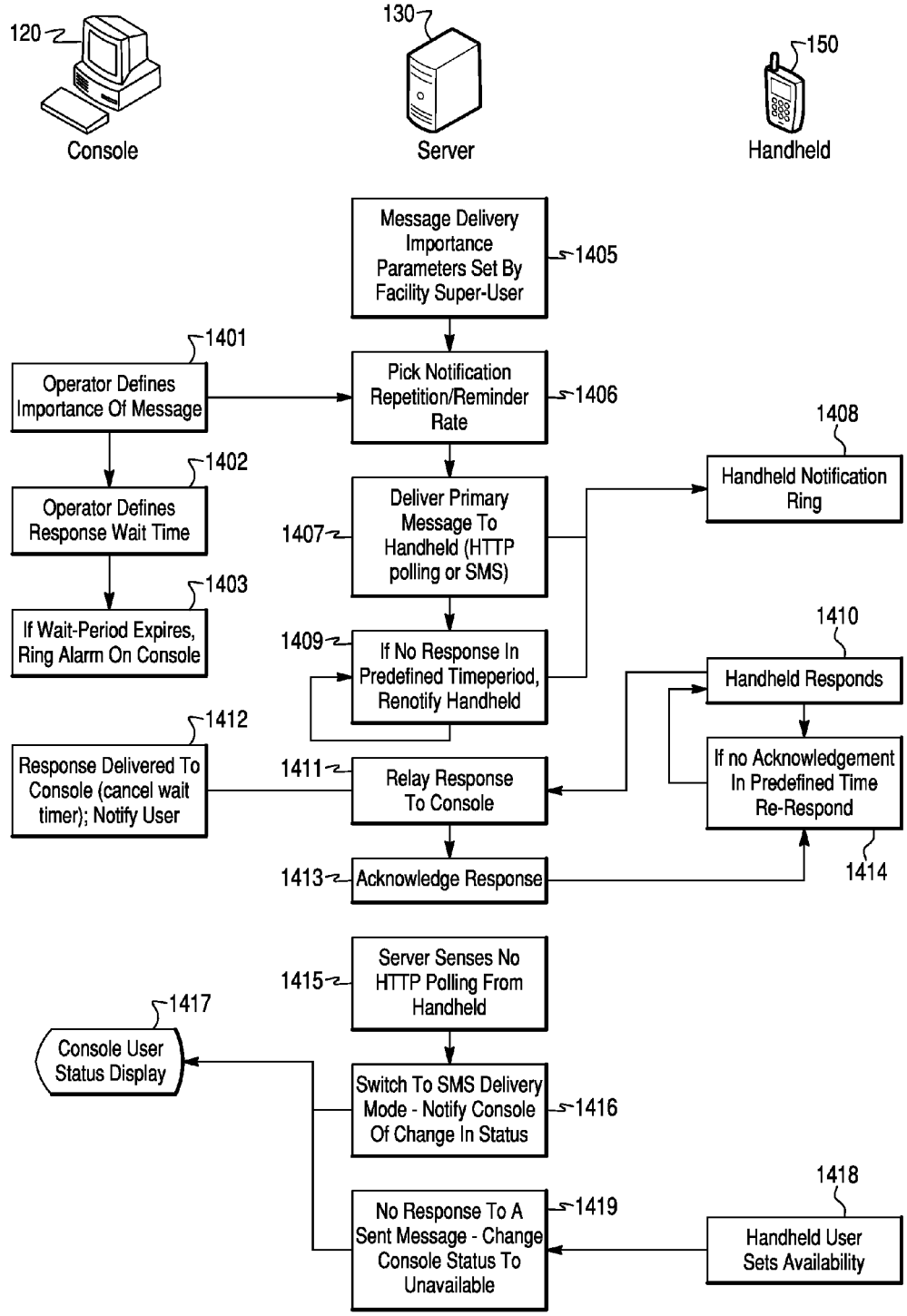
FIG. 14 is a flow diagram of a method for providing message status and notifications according to an embodiment.

Referring to FIG. 14, the user on a console may designate the importance of a particular message, 1401. The importance of a message may determine the number and frequency of delivery attempts and wait times used by the console and the server. It may also determine any internal reminder set ups available on the handheld or console software. For example, routine and non-emergency messages may be designated with low importance, signifying to the console and server software that long wait times can be accommodated and retransmissions of undelivered messages can be made on an infrequent basis (e.g., once per hour), or even done away with. Conversely, if a message is related to a medical emergency situation, such as a heart attack victim being transported in an ambulance, the console operator may designate it as a high priority message, signifying to the console, server, and handheld software that long wait times cannot be accommodated and retransmissions of undelivered messages should be made very frequently (e.g., once per minute) until a response is received.

The importance of the message may set the response wait time according to rules stored in the console, or server, or the operator may manually define the required response wait time, 1402. This is the time that can transpire before the console generates an alarm to notify the console operator that the message may not have been delivered or the physician may not be available or able to respond, 1403.

Message delivery importance parameters may also be set by a system administrator or other super-user according to hospital policies, 1405. Such policies may provide a maximum response time for physicians for one or more importance levels designated to each message or to a class of messages, after which other communication methods will be tried or other physicians contacted. Alternatively, the policies may set importance parameters for each of number of different medical circumstances, so that the importance parameter depends upon the nature of the communication and/or patient treatment situation. These importance parameters may also govern how many reminders are sent to or initiated on the handheld device to remind the physician, and the frequency of such reminder indications.

The server 130 receives the message performance information and determines the appropriate message repetition and reminder rates (i.e., time to wait before repeating a message transmission or sending a reminder) that should be implemented, 1406. The server delivers the primary notification message to the handheld device, such as by posting an HTML polling or sending an SMS message, 1407, and begins a timer. If no response is received from the handheld device, which may be in the form of a request for the relevant data associated with a message, within the appropriate response time period, the server 130 will retransmit the message or send a reminder message to the handheld device, 1409. This process of waiting and retransmitting/reminding may continue a predetermined number of times, with the number of repetitions determined by preset policies or based upon the importance of the message.

When the handheld device receives a message, it may activate a ring, vibrate, activate the display, or otherwise notify the user, 1408. The handheld device may also respond to the incoming message, 1410. Such response may be a receipt acknowledgement response (such as an SMS ResAck message), an automatic response generated by the handheld device, or a message generated by the physician. In an embodiment, the handheld device may request and wait for an acknowledgment of its message, and if no acknowledgement or response is received within a predetermined wait time, retransmit the response message, 1414.

Upon receiving a response from the handheld device, the data server 130 will relay the response to the console or inform the console that the message has been successfully delivered to the physician's handheld device, 1411. In response, the console may report the status of the message delivery to the operator and/or stop the message tracking timer. In an embodiment, the server 130 will also send an acknowledgement back to the handheld device, 1413.

If the server 130 determines that the HTML page holding the data for the physician has not been polled within a predetermine amount of time (determined based on policy or the message importance), step 1415, the server may send an SMS message to the handheld device and notify the console 120 of the changing in message methods, 1416.

If the server receives no response to any messages within a predetermined amount of time and/or a predetermined number of delivery attempts (with the predetermined amount based on policy or the message importance), the server 130 will notify the console and may change the physician's status to unavailable, 1419. In response, the console 120 may notify the operator of the message delivery failure, such as by means of a display, the sounding of an alarm or tone, or both, 1417. Alternatively, the console may determine or suggest to the operator that another physician to be contacted, in which case the process illustrated in FIG. 14 may be repeated. In instances where the handheld does receive the message and the physician fails to respond within the stipulated time period, the handheld software may create a similar alarm to warn the physician that the waiting message requires a follow-up.

In an embodiment, the system is configured with software programming of the server, console or both server and console working together, to review clinical data and automatically recognize clinically significant patterns that should be brought to the attention of a physician. Such patterns may be a single factor, such as a particular test result or a pattern in an ECG trace (e.g., a fibrillation pattern), or a pattern among two or more different data elements. The diagnostically significant pattern may simply be the portion of the data that contains information that may be of interest to a physician. For example, the system may automatically recognize portions of an ECG trace that contain relevant data, and reject portions (e.g., individual electrode traces) that have no relevant data. As another example, the server may be programmed to recognize portions of an X-ray image containing bone and tissue, and ignore portions that contain no image data. The server or console may further be programmed to fetch other relevant data, such as lab results, or previous ECG studies, based on such auto-detection results.

In an embodiment, the automatic recognition capability of the server, console, or server/console combination displays recognized diagnostically significant patterns to an operator on the console. For example, the system may display an ECG on the console and when a diagnostically significant pattern is recognized, shade, box, color or otherwise highlight the pattern on the display for the operator. Using such tools, the operator can select the identified pattern for transmission to the physician's cell phone. Thus, the system tools provides a semi-autonomous selection function where the system guides the operator to data of potential significance, but it is the operator that determines what is sent to the physician's cell phone.

In an embodiment, the data selection process can be fully automated. In this embodiment, upon detecting a diagnostically significant pattern, the server, console, or the server working in concert with the console may automatically select relevant sections of the patient data for transmission to the physician's cellular telephone. This automatic selection may be based upon the same criteria and methods used to recognize diagnostically significant portions. Alternatively, the automatic selection may be based upon other criteria. For example, the server may select portions of an ECG trace before, during and after a recognized diagnostically significant portion so that the physician can view the data before, during and after the recognized event, such as while reviewing a Holter monitor output.

Medical data gathered and considered by the system for transmission to the physician's cell phone may come from a number of different sources within the hospital, within emergency vehicles, within doctor's clinics, and within the patient.

One source of data is the medical database of the hospital where patient records are maintained in electronic patient record databases. Medical databases may also retain large data files associated with prior tests and medical images. Nonlimiting examples of such patient databases include: an electrocardiogram database; the hospital's electronic medical records database; an image database (which may include X-Ray, CT and MRI image data); an ultrasound image database; and a PACS database. Quite frequently such repositories of medical data records are maintained in electronic format in computer readable storage accessible via server connected to the hospital's network system. Such databases may be queried through standard database interfaces defined in such standards as DICOM or HL-7, or custom interfaces may be needed for such communication.

Another source of data will be data entry consoles and workstation, where nurses, doctors and technicians can enter patient data (both biographical and medical data) directly. An example of such sources are computer terminals in the emergency room for entering patient biographical information and recording vital statistics like body temperature, pulse rate, blood pressure, symptoms, etc. Typically such consoles and workstations are connected to a hospital's network. In some situations, the console is integrated with or also functions as a server on the hospital network.

Medical diagnostic devices may also be sources of data. Non-limiting examples of medical devices that may be sources of medical data include: electrocardiogram (ECG) equipment; electroencephalogram (EEG) systems; X-ray and fluoroscopy equipment; ultrasound imagers; computer tomography imaging systems; magnetic resonance imaging systems; positron emission tomography imaging systems; cardiac pacemakers and ICD interrogators; and automatic blood pressure and pulse rate monitors. Such medical diagnostic equipment may be located within the hospital and connected to the hospital's electronic network. The devices may also be remotely located, such as in a doctor's clinic or within emergency response vehicles (e.g., ambulance or helicopter) and transmitting data via wireless, cellular telephone, Intranet or other communication network. Some medical diagnostic equipment include as part of the system a workstation computer that is physically integrated into the equipment and can be connected to the hospital network, such as DICOM based PACS connectivity on ultrasound imagers. Other diagnostic equipment may be connected to a computer or workstation which is connected to the network, with the computer programmed to receive data from the medical device and store and/or transmit data via the hospital network.

Medical data may also come from medical devices implanted in or positioned on a patient. Non-limiting examples of such medical devices include: cardiac pacemakers; Holter monitors; portable blood pressure and pulse rate monitors; core temperature thermometers; and implanted defibrillators. Such devices may require a wired or wireless data connection to transmit their data to a system interface for transmission on to the hospital or the console.

Each data source and the operator console may be connected via networks that are wired (e.g., Ethernet), wireless (e.g., WiFi, Bluetooth), optical (e g., infrared), or combinations of these three well known networking technologies. In the case of consoles and diagnostic equipment located within an ambulance, the data link may be any wired data link available, including WiFi, Bluetooth, cellular telephone network, satellite data link; satellite telephone, and FM radio.

In various embodiments, the consoles are configured via software and/or security devices to limit access to authorized individuals. Any of well known security mechanisms may be used, including for example, recognition of a user's password, fingerprint, face shape, palm print, voice, and/or iris pattern, or a combination of one or more of these techniques. Additionally, the criticality or security level of uploaded data types of data can be manually or automatically defined.

In addition to encrypting data, known methods may be used to transit medical data with error correction and protection methods to minimize errors in transmission. In an embodiment, data is transmitted uses CRC checksums. In another embodiment, the data is transmitted using forms of authentication, including use of certificates of authentication.

In an embodiment, during operation the server sends one or more messages to the physician's handheld device notifying the device of the availability of data. The message may or may not contain contextual information regarding the data. Such contextual information informs the device and/or the physician about the type of information available on the server, such as whether this is a new transmission, a reply to a request from the device, or some other source for the communication. The server may send the notification message to the handheld when data is ready to be downloaded, or at one or more predetermined time-points.

In response to a message from the server that data is available, the handheld device may send a message to the server requesting transmission of the data. In response to this request, the server may transmit the data immediately or at some predetermined time point. Also, the server may send the entire data package to the handheld, or send a partial uploaded data to the handheld. A partial upload of data may be appropriate in circumstances where a wireless data connection is slow and/or unreliable. In such circumstances, the upload to the handheld device may be conducted in bursts, with one image downloaded at a time. Then, while the first image is being viewed by the physician the second image can be uploaded, and so forth until all images have been uploaded.

In an embodiment, the handheld device can transmit a message to the server informing it that the data download was successfully received. The server may also obtain such a message delivery confirmation from the network through which the notification is sent to the handheld. For example, a standard SMS delivery acknowledgement message may be forwarded to the server for this purpose.

In an embodiment, the server may send a reminder to the handheld if related data has not been requested for download within a predetermined time-span. Additionally, the server may send additional data availability messages to the handheld device in an attempt to cause the device to request download of the data. After a predetermined amount of time or a predetermined number of attempts to prompt the handheld device to download data, or a combination thereof, the server may notify the console and/or other predetermined points on the network. Such notification is important when a physician response is required in a timely manner. When the system is unable to upload the time critical data to the physicians handheld device within a set period of time, alternate physicians may be contacted or other contingency procedures implemented. Such Backup contact plans may be programmed into the system, such as the server or the console, for automatic or semiautomatic implementation.

In an embodiment, the server may be configured by software to authenticate the identity of the user of the handheld device prior to sending data to the handheld device. Such authentication may be in addition to authentication accomplished by the handheld device itself. In such an embodiment, if the user of the handheld device will first authenticate himself/herself to the device in order to begin data communications with the server, followed by an authentication exchange with the server in order to begin receiving patient information. Such user authentication methods may include, for example, a password which must be inputted on the handheld within a predefined time span following a prompt prior to the data request being sent to the server. As with other security measures, such user authentication can include other identification parameters such as, for example, the handheld's serial number, the handheld telephone number, or other unique identifying elements commonly found on cell phone handheld devices, a unique username for the user, or a permutation or combination of these identifiers.

In various embodiments, the medical data transmitted to the handheld device may be information enabling either qualitative or quantitative analysis. For example, information suitable for qualitative analysis may include X-ray and ultrasound images, while information suitable for quantitative analysis includes laboratory results, EKG's and vital sign information. To assist the physician, the handheld device may include software tools enabling the user to interact with the handheld device to perform quantitative measurements. Such tools may include simple calculators, distance, time, area, and volume measurement tools, spreadsheet tools, and pattern recognition or other diagnostic rule-based aids. Similarly, the handheld device may include software tools to enable the physician to manipulate qualitative information, such as images, to arrive at qualitative judgments. The software tools may also include algorithms for automated recognition or detection of certain clinical conditions.

The software tools running on the handheld may be written in software that can be run on multiple handheld operating systems. Such operating systems may include Windows Mobile, PocketPC, Symbian, Blackberry, or Palm. This software can also be implemented on any generic or altered Java Virtual Machine (JVM) on any of the above or other operating systems where the handheld software may be developed using any industry standard or other J2ME application development framework.

Alternatively, the software tools for aiding the physician may be hosted on the server with the handheld device programmed with a web browser type interface for requesting analysis by the software tools and displaying the result. This embodiment allows the server to complete measurements, analyze patient data and recognize patterns within the data, with results sent to the handheld device in the form of text or graphical displays. Since the server has much greater processing power and memory, much more sophisticated tools can be implemented with results generated much faster than may be achievable if the processing is performed on the handheld device. A user interface on the handheld device can receive inputs and display results in a manner so the user is unaware of where the actual processing takes place.

The server may further be configured with software so the display of the analysis results is formatted on the server and transmitted to the handheld device as an image. This embodiment enables the generation of complex, mixed format and contextual displays, such as a different display of results depending upon the nature of the analysis or the recognized condition, without overloading the handheld device's memory and processor. The server and handheld device may be configured with software so that resulting displays are automatically downloaded to the handheld device as they are completed by the server, or are downloaded to the handheld device on demand, such as in response to a user action. The server may also transmit displays providing structured data input memories, such as procedure order and prescription forms that the physician can complete with text entry, menu selections or both.

In various embodiments, the software operating on the handheld device includes functionality to record various physician orders, notes diagnosis, plan of therapy, observations, prescriptions, and combinations thereof that are relevant to patient care. Such recorded information may be typed text, handwritten text, or voice recordings, or combinations of these three data types in order to provide the physician with a variety of data entry method alternatives. Such patient care information input into the handheld may be stored on the handheld device and then transmitted to the server through the cellular telephone network. The transmission of such patient relevant information may be in any digital data transmission method, including for example electronic mail, SMS message, MMS message, WiFi electronic data transmission, Bluetooth, and satellite telephone data transmission.

In the various embodiments, the handheld device is configured with software to be capable of displaying new messages and alerting the user of the arrival of new messages. The handheld device may include multiple types of alerts, including but not limited to audio alerts, mechanical (vibration) alerts, and visual or text alert messages displayed on the display screen. Such variety of alerts may be dependent upon the importance of the incoming message.

In the various embodiments, the server and handheld device may be configured to control the conditions under which data is transmitted to the handheld device. The server and handheld may be configured so that certain or all data is automatically downloaded to the handheld without user actions. In an alternative configuration, the server and handheld may be configured so that the data is downloaded from the server to the handheld only upon an explicit action from the user, such as pressing a key or selecting a "receive" menu option. In another alternative configuration, a subset of the data is downloaded from the server for preview by the user, while the complete data set is downloaded only after an explicit action by the user.

The handheld device may be configured with software to display an indication of a data download status, data download progress, data review status, and/or data upload status.

The handheld device may be configured with software so that upon completion of data review and user input, the medical data is stored in the handheld for later review. Such data may be stored in encrypted or unencrypted format.

The handheld device may be configured with software so that upon completion of data review and user input, the user input data is automatically uploaded to the server, or is uploaded to the server after an explicit action by the user, such as pressing a key or selecting a "send" menu option. The handheld device may be further configured so only data that has been added or changed is uploaded to the server. The handheld device may also be configured so that data uploaded to the server is sent encrypted with authentication information and error detection and amelioration features.

The handheld device and server may be configured with software so that the uploaded data is forwarded automatically to the server, or is sent to the server upon demand from the original sending console. The server may also be programmed so data is also distributed to other predetermined points, and archived on the server. Also, the server may send the uploaded data to multiple databases, such as to all databases that relate to the patient (e.g., medical records, billing, prescription, etc.).

In the various embodiments, the server and/or console may be configured with software so that upon reception of data from the handheld device, the console signals the console user of the availability of the physicians input. This software configuration may display certain text portions of the physician's response within predefined areas on the user interface screen. Such an interface screen may be in any user interface, including for example, a graphical user interface, web browser page, a control panel display or a medical order form with dynamic fields. For example, the console display may be in the form of a control panel which presents the user with an organized display of patient data, patient medical information and images, messages and requests transmitted to a physician's handheld device, status of message transmissions, messages and orders received from a physician's handheld device, and the status of subsequent patient treatment or testing procedures.

While the foregoing system provides significant advantages for patients and physicians, its use of public communication systems, including cellular telephone networks and servers, requires special security measures. Patient privacy must be protected under HIPAA and other U.S. laws, yet some of the information being communicated may need to be decrypted by an intermediary server or sent unencrypted in order to enable data processing associated with communicating the entire file to an intended recipient.

Figure 15:
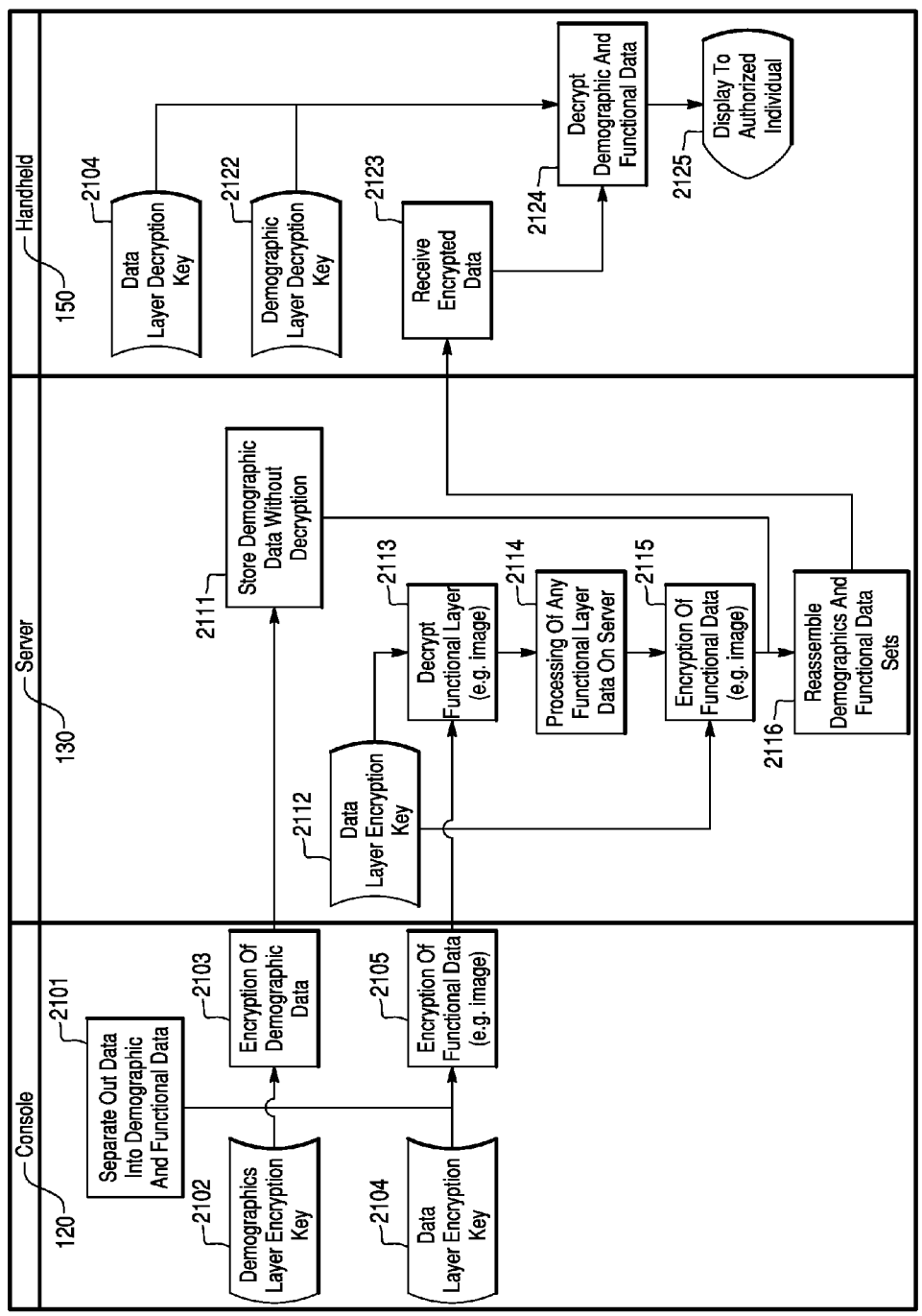
FIG. 15 illustrates the overall operating data flow of an embodiment of the present invention.

FIG. 15 is a general system and process flow diagram of an exemplary embodiment configuration of the system, wherein data is sent from a computer or digital console 120, through an intermediary server 130, to a remote handheld computer 150. Data is generated or accessed by the sending console 120. The data is separated out into at least two separate parts, such as demographics and functional data 2101. As a first example, if the data was a DICOM file with medical images (e.g., X-ray or ultrasound images), the data may be separated into a first part, or header, containing the patient demographics data, including, for example, the patient's name, date of birth, and other personal information, and a second part that contains the raw images. As another example, files containing the results of a requested test or procedure (e.g., an EKG or laboratory test) that include the patient's referral information (e.g., the patient's name, address, social security number, other identifiers, health insurance particulars, etc.) along with the results may be separated into a demographics file containing the patient's name, address and other personal demographic details, etc., while the pure clinical data, such as the EKG, or lab results, are separated into a clinical data file. Separated parts of medical data are also referred to herein as "layers" or "data layers."

Once the personal information has been separated from the clinical or image information, the two (or more) parts of the medical data are encrypted with separate encryption keys. While the demographics layer is encrypted with one encryption key 2102, 2103, the data layer is encrypted with a separate encryption key 2104, 2105. Any encryption method can be used to encrypt the various data layers, including, for example, 128 bit public key encryption. Also, the various data layers may be encrypted using different encryption methods or encrypted with different levels of security. For example, medical image data which may present less privacy concerns when separated from personal demographic information may be encrypted with a less secure, but faster encryption method, such as 32 or 64 bit public key encryption.

The separately encrypted data layers can then be sent to a server 130. This server 130, or any intermediary waypoint, only has the decryption key or keys useful for decrypting the data layer 2112. Thus, the server 130 is unable to decrypt the demographics layer. If processing of the data layer is required, the data layer may be decrypted on the server, 2113, using the data layer key 2112. Data held in the data layer can then be processed in the server in any way necessary for the communication system. A number of data processing operations may be performed on some or all of the data within the decrypted data layer. For example, the data layer may be processed to select and/or compress medical images, filter EKG signals, apply auto-detection to signals, or other processes in order to reduce the volume of data to be communicated to a recipient.

Once the server has completed processing of the data layer, the server can use a data encryption key to re-encrypt a portion or all of the processed data layer such that it is safe to transmit this data layer through any public or private network. In this step, the server uses a data encryption key whose decryption key is known to the destination, such as a physician's handheld device (e.g., a cell phone). This second data encryption key (or encryption/decryption key sets) may be the same as was used to encrypt/decrypt the data layer before it was sent to the server (2112), or it may be a different key or key sets that are shared between the server and the handheld.

In various embodiments, the server processes some or all of the data within the decrypted data layer to facilitate communication of medical diagnostic and image data to a physician's handheld device (e.g., a cell phone). Due to the limited memory and processing power of handheld devices like a typical cellular telephone, as well as the limited bandwidth for transmitting data via cellular telephone networks, the communication system my communicate only those portions of the data layer to be displayed or of interest to the physician. Thus, in a first example embodiment, the server may be programmed to process an image within the data layer to select for transmission to the handheld device only that portion of the image which will be displayed on the device. In this example, the server will decrypt the data layer using the data layer decryption key, process the image to select the portion to be displayed, format an display image comprising the selected portion of the original image, encrypt the display image using a data layer encryption key (either the same key or a different key), and then send the encrypted display image as a data layer to the physician's handheld device. In such an embodiment, the server may receive data requests from the handheld device to process and transmit a new image selection for display, in which case the server may perform the steps of image processing, re-encrypting and transmitting a new data layer to the handheld.

In a second example, the server may process an image within a decrypted data layer in order to compress the file size of the image to facilitate transmission to and display on the handheld device. Handheld devices have limited display resolution and limited processing capability. To overcome such limitations, adjustment of the image resolution such that it is consistent with the handheld device display capabilities and compression of the resulting image data to reduce the amount of information to be communicated via the cellular telephone network is performed on the decrypted data layer by server. The server then encrypts this processed and compressed image data into a new data layer that is transmitted to the handheld device for decryption and display.

In a third example embodiment, the server may decrypt a data layer including an EKG data stream, perform pattern recognition processing on the data stream, such as EKG diagnostic tools, and select portions of the EKG that contain diagnostically significant information. The server may then encrypt the selected portions of the EKG and send the selected portions to the handheld device as a new data layer.

In a fourth example embodiment, a physician may input into the handheld device search criteria or otherwise indicate the type of data to be displayed on the handheld device, which transmits the selection criteria to the server. The server can use the received selection criteria to select from the decrypted data layer a subset or portion of the medical data to be sent to the physician's handheld device. The server then encrypts the selected portion of the data from the data layer and transmits it to the handheld device as a new data layer.

In a fifth example embodiment, the server, working in concert with the console, accesses and indexes historic data files or secondary data pertaining to a particular patient. On demand from the physician, such historic data can also be delivered to the handheld device to allow the physician to do a chronological comparison of data. In this embodiment, the server arranges the accessed data in unique formats that allow for easy delivery, viewing and analysis on a handheld device. This embodiment provides intelligent tools on the server-console combination that can respond to data and circumstances to anticipate the physician's information needs. For example, a server according to this embodiment can be programmed to recognize an elevate ST segment in a patient medical file and, working with the console, automatically ask for the patient's blood cholesterol levels (and other relevant information) from the EMR system and make such information available on the physician's handheld device without the physician having to specifically request the information. Such automatically accessed information may be combined in the same display, cached in the handheld device for rapid display (e.g., in response to a menu selection), or cashed in the server for rapid communication to the handheld device when requested by the physician.

In each of the foregoing example embodiments, the server selects and sends at least a portion of the processed data layer information and encrypted data layer. Thus, these embodiments enable a system server to perform processing on the data layer that would otherwise have to be accomplished by the handheld device without risking disclosure of the demographic data in the event the server is compromised.

Figure 18:
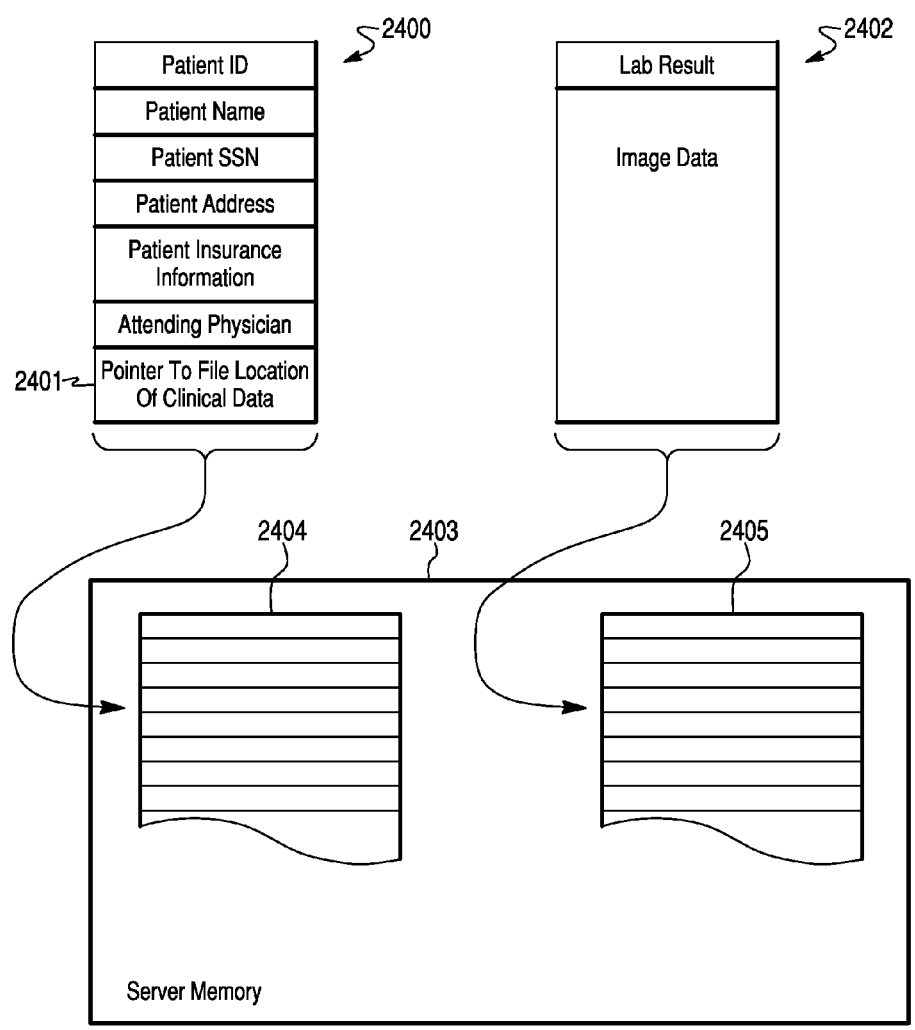
FIG. 18 is an illustration of data structures of a database useable with one or more embodiments.

The two layers of the source file can be maintained (i.e., stored in memory) within the server with a common trace header. Alternatively, as illustrated in FIG. 18, a pointer 2401 to the file location of the second data layer 2402 may be embedded (e.g., a data entry) within the first layer 2401. This configuration allows the receiving handheld to decrypt the first layer 2400 to learn the pointer to the file location of the second layer 2402, and then request the appropriate matching second layer 2402 from the server by transmitting the associated pointer 2401. As illustrated in FIG. 18, the demographic data layer 2400 may be stored in server memory 2403 in a database of demographic files 2404 that is in a different file location or even on a physically separate memory (e.g., on a separate hard drive) from a database of data layers 2405. This alternative file storage and data layer linkage configuration allows for complete blinding of the data layer (e.g., clinical data) from the encrypted patient demographics data. Thus, this alternative adds an additional layer of security for data stored on the server, even from persons authorized to access the server.

Referring back to FIG. 15, both (or all) data layers can then be sent to the physician's handheld. The two or more data layers can be sent in parallel, or serially one after the other. Alternatively, one layer may be sent first after which the handheld identifies and requests the other layer. For example, using the data configuration illustrated in FIG. 18, the demographic data layer 2400 may be sent to the handheld, which decrypts the data it to access the pointer 2401 and then transmits the pointer information to the server requesting that the associated second data layer 2402 be transmitted.

When the handheld receives an encrypted data file, it uses its data layer key 2121 and its demographics layer key 2122 to decrypt both data layers and then displays the information to the authorized individual.

In an embodiment, the demographics layer carries a header file that identifies a streamable data layer, such as a movie file as used in echocardiography, or a real-time EKG signal, either stored on or routed through the server. Upon decrypting the demographics layer, the handheld sends a request to the server to transmit the relevant data file as a data stream. The data file is then sent by the server to the handheld in a streaming format such that the handheld can receive and display the streamed data. The streaming data file may be encrypted as it is transmitted.

The system and encryption methods can be made even more secure by deleting the header file from the server after sending it to the handheld, such that after the request for the second data layer is received and processed by the server, the original demographic data no longer exists on the server. This option eliminates the possibility of a potential hacker monitoring the order of data transferred in order to match a demographics layer to a data layer.

The sending unit of the communication system may be any computing device with capabilities to process such data. The intermediary point may be a specific server, a collection of various servers, or even a partly manual process with human intermediaries. Also, the receiving unit (referred to sometimes as a handheld) may be a cellular telephone, personal digital assistant, laptop computer, desktop computer, another server, or any other device or system with data processing capability.

Figure 16:
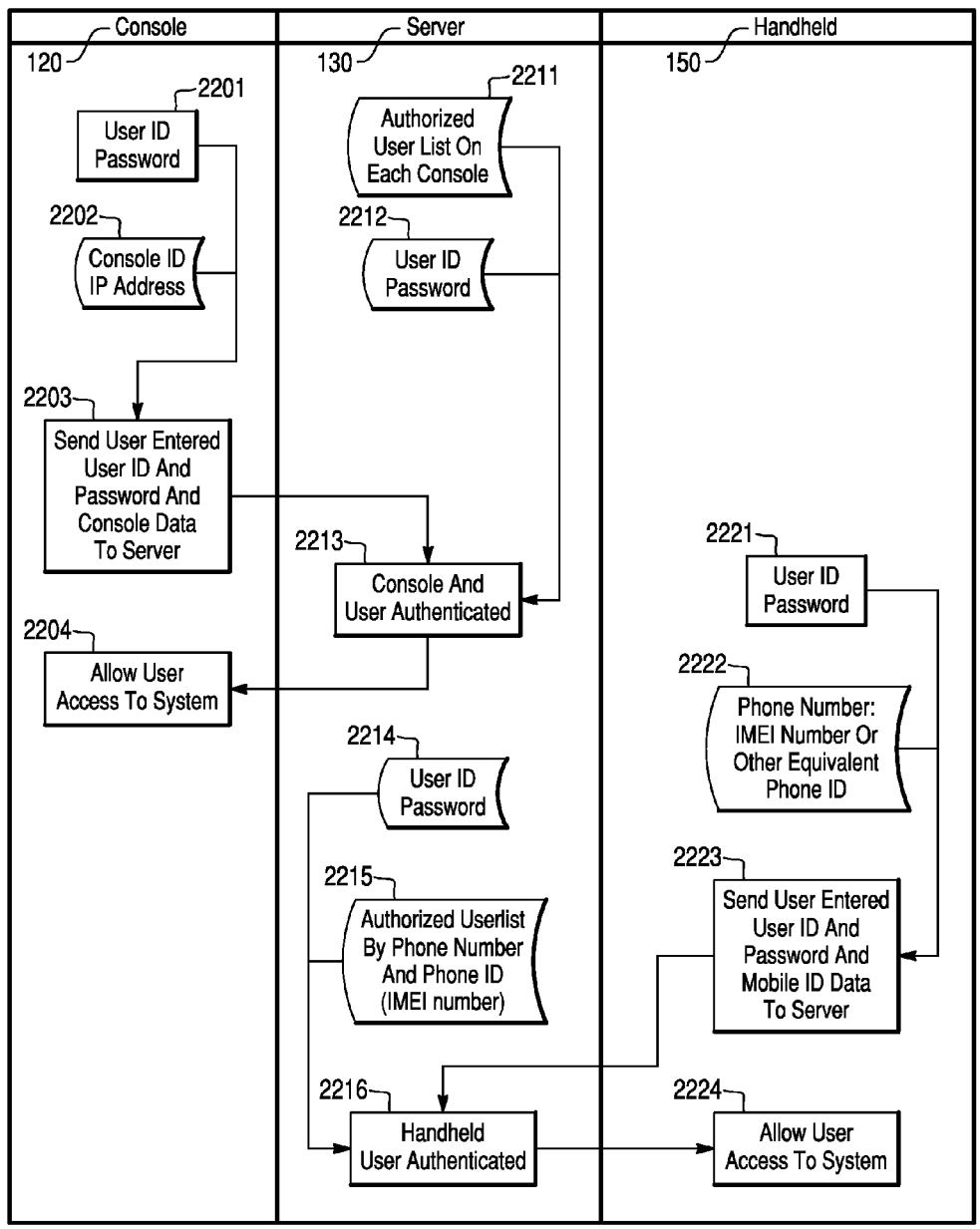
FIG. 16 illustrates an embodiment of a log-in and authentication process useful for granting user access to data.

FIG. 16 illustrates an aspect within such a secure system for authenticating users. Medical data may be transmitted from a workstation, console or medical diagnostic unit that may be located in a relatively public and busy area, such as an intensive care unit. In such public or high-traffic, busy locations, a person with malicious intent might be able to physically access the workstation, console or medical diagnostic unit. Also, the physician's handheld unit can be a cell phone based system, in which case there is the possibility that the cell phone may be stolen. If stolen, the software on such a handheld unit might be copied and installed on another phone in an attempt to mimic the original phone. Therefore, an authentication system may be implemented to defeat such hypothetical attacks. An example embodiment of such a system illustrated in FIG. 16 uses hardware as well as personalized unique identifiers to authenticate and limit access to authorized users.

In an embodiment, the user logs onto the system with a unique user ID and password 2201. While the user ID and password may be conventional alphanumeric strings known to the user, such data may also include other unique high-security identifiers such as fingerprint or iris scan images obtained by a biometric sensor. The user ID data is combined with the unique identification of the particular console being accessed, which could be the name of the console, its IP address, the network identification of the computer, etc. 2202. The combination of the user ID, password and console ID is sent to the server for authentication 2203. The server carries a database of authorized users, passwords, and consoles for the individuals authorized to log on to the system 2211, 2212. The server compares the user ID, password and console ID data to the authorized user database and, if there is a match, signals the console software to allow access to the user 2213, 2204.

Similarly, the handheld 150 user logs onto the handheld using a unique user ID and password 2221. This user authentication information is then combined with an identifier unique to the handheld device 2222 and the combination is sent to the server 2223. Handheld unique identifier may be the telephone number of the phone, a number separately stored on the handheld in an undisclosed location and accessed internally by the software, the IMEI number which is unique to each cell phone handset, or other such unique identifier. The server compares the received combination data to the user ID and password list 2214 and the authorized user list by phone number/device ID 2215 and authorizes the log in to the handheld device if a match is obtained 2216, 2224. If the user is authenticated, the server may send commands to the handheld device instructing it to allow the user to access the functions and data on the device, as well as enable transmission of data to the handheld. If the user is not authenticated, the server may send commands to the handheld device to disable data decryption algorithms, encrypt or delete data stored on the device, disable some or all handheld functions, and/or inhibit transmission of data from the server to the handheld.

Other user authentication embodiments may include multi-level user passwords for accessing or authorizing critical data, biometric scanners on the handheld (e.g., fingerprint or iris scanners), voice print matching algorithms and other biometric signature matching equipment or algorithms that can allow access to one or more layers of data on the system, console and/or handheld device.

Figure 17:
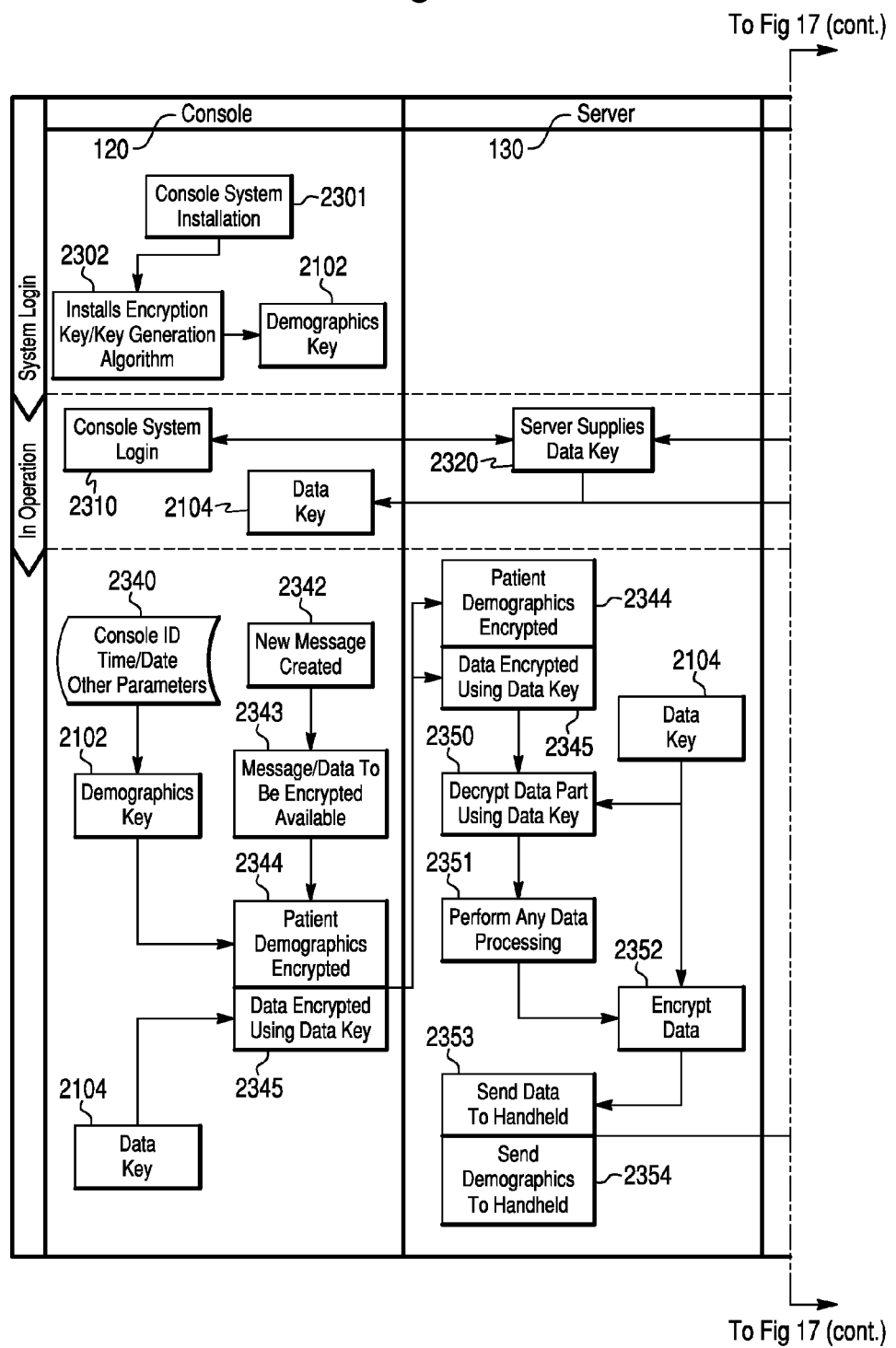
FIG. 17 illustrates a method for generating encryption keys and communicating data which allow access to only parts of medical data stored on a server.
Figure 17:
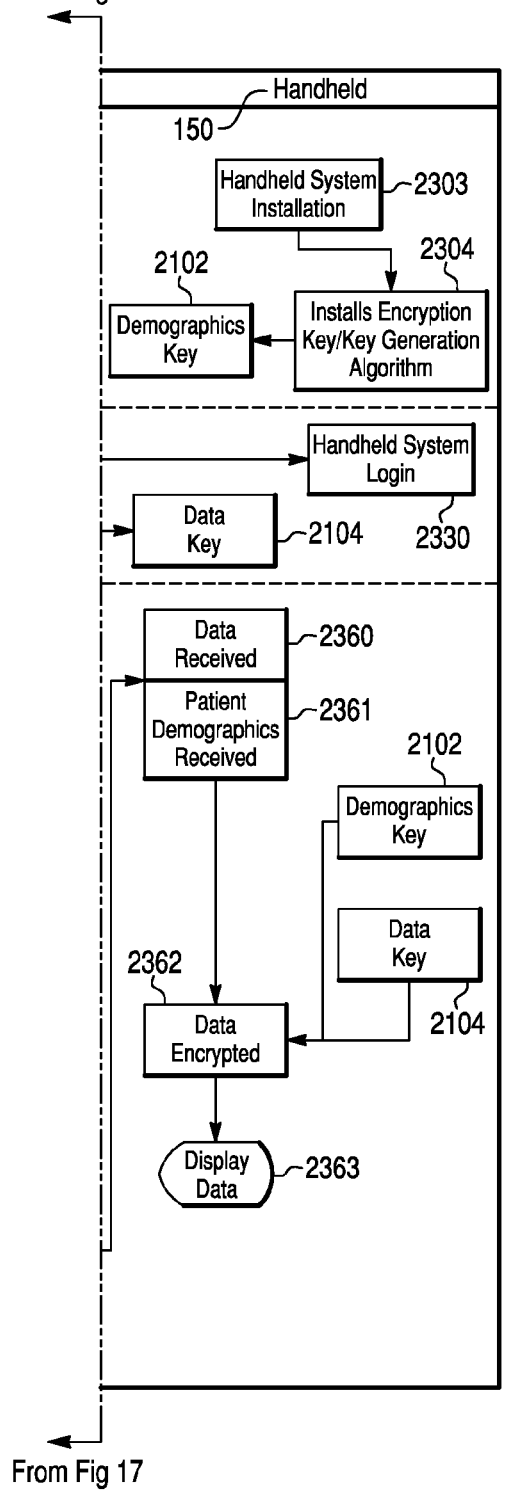

FIG. 17 details an embodiment for the encryption key generation process. In the illustrated process, the data layer key or the demographics layer key generation algorithms 2102, 2122 are shared only between the console and the handheld and are not available to the server, while the data layer keys or key generation algorithms 2104, 2112, 2121 are available to the console, server, and the handheld.

During system install on the console, the installation process 301 installs the encryption key, set of keys, or the key generation algorithms 302 in console memory. This encryption key, set of keys, or algorithm which generates keys provides the encrypting demographics key 2102.

Similarly, during system install on the handheld 2303, the process installs the key necessary for decryption or set of decryption keys, and/or the algorithm for choosing or generating the decryption keys 2304 for the demographics layer and for the data layer. Thus, the server has no knowledge of the encryption and decryption of the demographic layer. As mentioned above, the key used to decrypt data layers may be the same key that is used to encrypt the layer originally (i.e., mirror keys), a different key.

The data layer encryption and decryption key generation/distribution may employ any well known public/private key architecture as are well known to those skilled in the art. Alternatively, the data layer encryption and decryption key generation/distribution may be a process as illustrated in FIG. 17, wherein the server supplies the data key 2320 when the console log-in or boot up process occurs 2310, 2330. Further, although not shown in FIG. 17, the data layer keys used for communications between the console and the server may be different from the data layer keys used for communications between the server and the handheld. Similarly, the encryption algorithms used for encrypting/decrypting the data layer may be different from the encryption algorithms used for encrypting/decrypting the demographic layer.

The various keys used for encryption can be separately provided as a single non-changing key, employ a time based look-up method similar to any one-time use key, or be dynamically generated by any known key generation algorithm. Further the encrypting key can be separate, while a separate mirror of the encrypting key can be used to describe the decryption key or process.

In operation of an embodiment of the system, the console ID is used to generate the demographics key when data is available for encryption. Time-dependent, or time-independent variables, such as console ID, the time and date the message was generated, and other random or semi-random variables can be used to seed an algorithm to generate the demographics key 2102. A similar process can also be used to generate the data key 2104, however, in which case, the methodology to decrypt such a dynamically generated key is known to at least the server.

The separate data layer 2345 and demographics layer 2344 (and potentially more layers) of the message 2342 are encrypted using the respective data and demographics keys and the results sent to the server. As mentioned earlier, the unique header, a memory point, or other identifier for the data layer may also be embedded within the encrypted demographics layer to further blind the server at this stage.

When it receives the transmitted encrypted message, the server uses its internal data key 2104, or a complimentary data decryption key that may be generated by a predefined process, to decrypt the data layer. Data processing is performed on this decrypted data 2351 after which the data may be again encrypted and stored. The encrypted data layer and demographic layers are then sent to the handheld 2353, 2354. As mentioned earlier, this last step can be broken into the server sending the handheld the demographics layer separately, with the handheld then requesting a specific separately stored file comprising the data layer.

The handheld receives the data layer 2360 and the demographics layer 2361. The handheld obtains the demographic layer and data layer decryption keys 2102, 2104, such as by recalling the keys from memory if in a stored format within the handheld or dynamically generating the keys using a predefined process. These decryption keys are then used to decrypt the respective layers enabling the handheld to display the data to the user in an integrated fashion.

In another embodiment, the foregoing methods for encrypting and decrypting data are spread across multiple way-points and the data are separated out into multiple layers, with each layer containing data that is uniquely required to be accessible at one or more way-points, while the rest of the data remains encrypted. In this embodiment, each way-point may have a decryption key unique to the data layer it must access to enable its portion of the message processing and communication process. For example, a message may be separated into a demographics layer and data layer as described above, plus a message routing layer, a physician action layer, and a record-link layer. In this example, the message routing layer may contain private information required for routing the files to the appropriate destination, such as the cell phone number of the physician's handheld which is required by a cell phone network server to accomplish the communication. Further in this example, a physician action layer may include treatment, laboratory or consultation orders, prescriptions, notes or diagnosis. Similarly, a record-link layer may contain file record locators or memory pointers that indicate the storage location(s) of the patient's medical records within the hospital system. Each of these three additional layers contain potentially sensitive information which may need to be accessed by different servers and data systems which do not require access to the entire patient data file being communicated. By selectively encrypting distinct subsets of patient medical data and records, patient files can be efficiently communicated over a semi-secure network without revealing any more information to each way-point server than is needed for the particular processing accomplished at such way-point.

Figure 19:
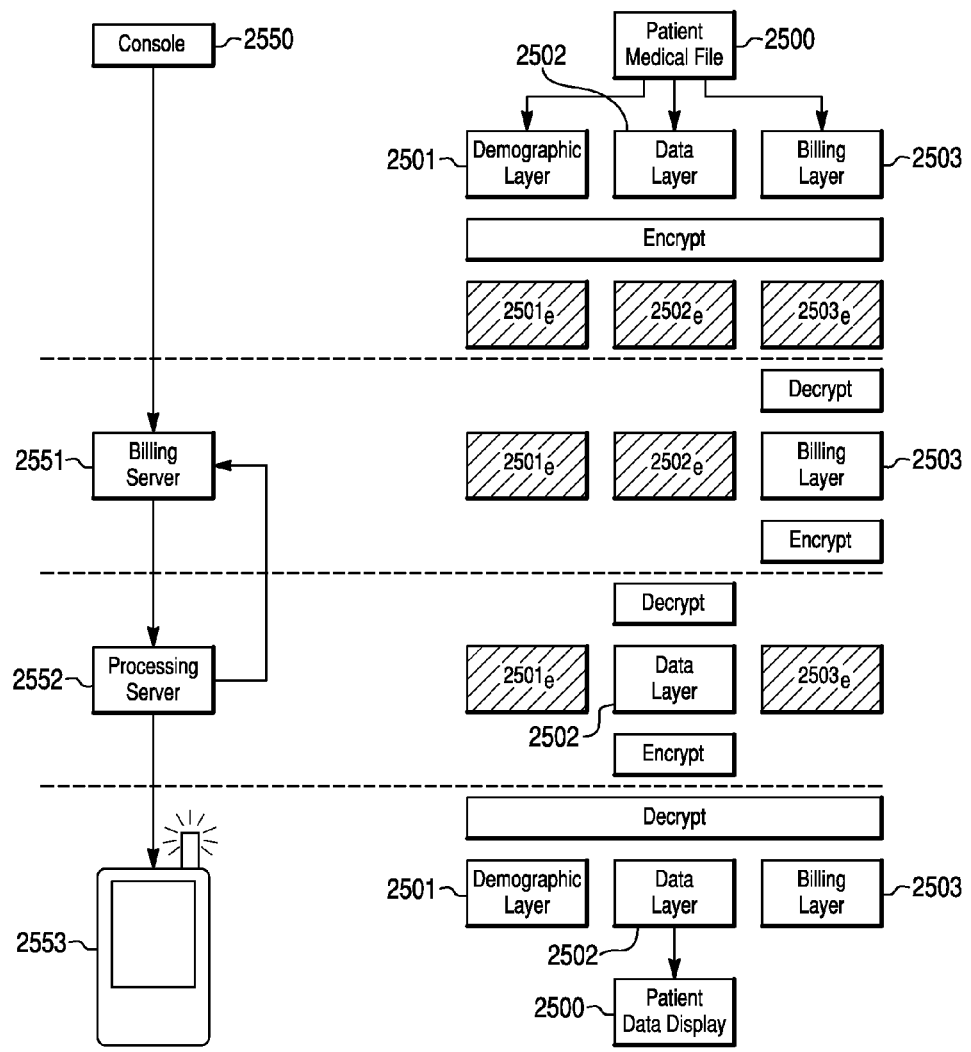
FIG. 19 is a process flow diagram of an embodiment method.

FIG. 19 illustrates an example embodiment in which the patient medical file 2500 is separated into three layers, a demographic layer 2501 including personal information of the patient, a data layer 2502 including clinical, image or diagnostic data that does not inherently reveal the identity of the patient, and a prescription layer 2503 including information related to the patient's current and past medications. After the three layers are created by the console 2550, each layer is encrypted with a different encryption key. The data file then may be routed to a prescription server 2551 which has a decryption key for the prescription layer 2503, but not for the demographic layer 2501 or data layer 2502. The prescription server can then decrypt the prescription layer in order to perform prescription processing operations on the data within that layer (such as update the patient's medications or order medications to be administered). However, the prescription server is unable to access or display the encrypted demographic layer 2501e or data layer 2502e. For example, the prescription layer data may be updated to reflect additional medications being administered or to order delivery of a new prescription. For example, the console may be located in the emergency room where patient intake is occurring, so the prescription server may update the data within the prescription layer to open a new prescription and/or record additional medications that may have been administered in the emergency room. Before the file is sent on from the prescription server, the prescription layer is re-encrypted using a prescription encryption key (either the same or a new key).

Next, the entire medical file may be routed to an image processing server 2552 which can decrypt the data layer 2501, but cannot decrypt, access or display the demographic layer 2501e or prescription layer 2503e. The image processing server 2553 can then select a portion of the image for display on the physician's handheld device 2553, for example, which is then re-encrypted before the file is sent on to the handheld device 2553.

The handheld device 2553 has decryption keys allowing it to decrypt, access and display each of the demographic layer, data layer and prescription layer, thereby reassembling the patient's medical file 2500. Alternatively as a further example, the handheld device 2553 may only have the decryption keys for the demographic layer and the data layer, leaving it unable to access or display the prescription layer.

In a further embodiment, data from a critical lab results database, medical images, physiological variable plotting (such as EKG and respiration), recent prescriptions, and a summary of the patient's previous medical history are assembled into a message by the console, with each of these components forming a separate data layer of the message. The complete assembled file can be forwarded to the physician's handheld device through a server. The server may only have the keys to decrypt the physiological variable data and the images, while the other data layers are sent on to the physician's handheld in the manner previously described without decryption on the server.

The physician's handheld device then decrypts all of the data layers and displays the data to the physician. Using the information, the physician may enter orders, issue prescriptions and/or set up a treatment plan. The handheld device may then reencrypt each of the data layers separately, add a prescription/treatment plan/orders layer to the collection of data layers, and send the assembled message back the hospital through the cellular telephone network server, along with a routing file which defines the routing of each of the data layers.

For example, the data layers, which may have measurements performed by the physician attached, may be routed back to the database that archives such data files. The physician's orders and prescription may be sent back to the originating console for the attending nurse to take appropriate actions. The prescription layer may be sent to the prescription processing system, for electronic processing of the prescription. A copy of the complete file may also be updated on the hospital's Electronic Patient Record system.

The specific message routing may be different in different hospitals, as dictated by standard work flow and local controls. Message routing and server access to specific data layers may be established to a particular hospital's requirements when the system is initially installed.

The various embodiments ensure that even if a server is "hacked" or accessed by an unauthorized operator, such intruders are unable to reassemble the patient demographics information and obtain access to the entire patient file. If intruders do gain access to a server, they can only see images or EKG traces without any knowledge regarding to whom such data pertains. This provides greater patient protections that specified by HIPAA since HIPAA compliance has been based upon employees and hospitals certifying that they will not leak patient data to which they have access. The various embodiments prevent hospital employees or hackers from being able to access and decrypt patient demographic data, so that only unidentified clinical data can be accessed.

The foregoing embodiments may be implemented in software operating on programmable processors, in hardware and in combinations of hardware and software. In particular, encryption and decryption methods and algorithms may be implemented specialized encryption/decryption circuitry according to methods well known in the encryption and telecommunication arts. Further, software for accomplishing the various embodiment methods may be recorded on any computer or processor readable tangible memory.

The foregoing description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments described herein but is to be accorded the widest scope of the following claims consistent with the principles and novel features disclosed herein.

We claim:

1. A system for communicating a medical record of a patient, comprising:
   a medical data system configured to collect medical data;
   a console comprising a processor coupled to a network;
   a mobile device; and
   a server coupled to the network,
   wherein the console further comprises a memory storing instructions that, when executed by the console processor, cause the console processor to perform a method comprising:
      receiving medical data and a diagnostic image from the medical data system;
      accessing the medical record of the patient;
      receiving an operator input selecting a portion of the medical record and the diagnostic image for transmission to the mobile device;
      separating the selected portion of the medical record and the diagnostic image into a plurality of layers including a demographic layer comprising demographic information selected from the medical record and a data layer comprising medical data and the selected first portion of the diagnostic image;
      encrypting the demographic layer using a first encryption key;
      encrypting the data layer using a second encryption key, wherein the second encryption key is different from the first encryption key; and
      sending the encrypted demographic layer and data layer to the server,
   wherein the server is capable of decrypting one of the encrypted demographic layer or the encrypted data layer but not both, and
   wherein the server comprises a processor and a memory storing instructions that, when executed by the server processor, cause the server processor to perform a method comprising:
      decrypting the data layer;
      performing an operation on the data layer comprising selecting a second portion of the diagnostic image;
      re-encrypting the data layer; and
      sending the encrypted demographic layer and re-encrypted data layer to the mobile device via a wireless network.

2. The system of claim 1, wherein the medical data system is a medical diagnostic device.

3. The system of claim 1, wherein the medical data system is an electronic medical records database.

4. The system of claim 2, wherein the medical device comprises one of an electrocardiogram system, an imaging system, and a system designed to measure physiological variables.

5. The system of claim 2, wherein the console is implemented within the medical diagnostic device.

6. The system of claim 1, wherein the server is implemented within the console.

7. The system of claim 1, further comprising a medical imaging system, wherein the server is implemented within the medical imaging system.

8. The system of claim 1, wherein the medical data system is contained within an ambulance.

9. The system of claim 1, wherein the server memory stores instructions that, when executed by the server processor, cause the server processor to perform a method further comprising:
processing images to match display characteristics of the mobile device; and
transmitting the processed images to the mobile device.

10. The system of claim 9, wherein the server memory stores instructions that, when executed by the server processor, cause the server processor to perform a method further comprising:
receiving an image request from the mobile device; and
processing images in accordance with parameters contained in the image request.

11. The system of claim 1, wherein the server memory stores instructions that, when executed by the server processor, cause the server processor to perform a method further comprising:
recognizing a pattern or feature within the medical data; and
automatically taking actions based upon the recognized pattern or feature.

12. The system of claim 11, wherein the automatic actions taken based upon the recognized pattern comprise recalling patient data relevant to the recognized pattern or feature.

13. The system of claim 1, wherein the server memory stores instructions that, when executed by the server processor, cause the server processor to perform a method further comprising:
determining a potential diagnosis by recognizing a pattern or feature within the medical data;
automatically recalling recall patient data relevant to the determined potential diagnosis; and
transmitting to the mobile device the recalled patient data.

14. The system of claim 1, wherein the server memory stores instructions that, when executed by the server processor, cause the server processor to perform a method further comprising:
recognizing a pattern within data being sent to the mobile device; and
automatically obtaining additional data that is relevant to the recognized pattern.

15. The system of claim 1, wherein the server memory stores instructions that, when executed by the server processor, cause the server processor to perform a method further comprising rendering a three-dimensional medical data set so an image can be displayed on the mobile device as an isometric image.

16. The system of claim 1, wherein the server memory stores instructions that, when executed by the server processor, cause the server processor to perform a method further comprising rendering a three-dimensional medical data set so a movie can be displayed on the mobile device as a rotating isometric movie.

17. A system for communicating medical data, comprising:
an emergency medical unit comprising:
an emergency medical vehicle,
at least one medical data recording device configured to collect medical data, and
a transmitter configured to receive medical data from the at least one medical data recording device;
a console comprising a processor coupled to a network; and
a server coupled to the network,
wherein the console further comprises a memory storing instructions that, when executed by the console processor, cause the console processor to perform a method comprising:
receiving medical data and a diagnostic image from the emergency medical unit;
accessing the medical record of the patient;
receiving an operator input selecting a portion of the medical record and the diagnostic image for transmission to a mobile device;
separating the selected portion of the medical record and the diagnostic image into a plurality of layers including a demographic layer comprising demographic information selected from the medical record and a data layer comprising medical data and the selected first portion of the diagnostic image;
encrypting the demographic layer using a first encryption key;
encrypting the data layer using a second encryption key, wherein the second encryption key is different from the first encryption key; and
sending the encrypted demographic layer and data layer to the server,
wherein the server is capable of decrypting one of the encrypted demographic layer or the encrypted data layer but not both;
wherein the server further comprises a processor and a memory storing instructions that, when executed by the server processor, cause the server processor to perform a method comprising:
decrypting the data layer;
performing an operation on the data layer comprising selecting a second portion of the diagnostic image;
re-encrypting the data layer; and
sending the encrypted demographic layer and re-encrypted data layer to the mobile device via a wireless network.

18. The system of claim 17, further comprising the mobile device, wherein the mobile device is a cellular telephone configured to receive and display the medical data.

19. The system of claim 17, wherein the console is a computer in the emergency medical vehicle.

20. The system of claim 19, further comprising a second console located in a hospital.

21. The system of claim 17, wherein the emergency medical vehicle is a ground ambulance.

22. The system of claim 17, wherein the emergency medical vehicle is an air ambulance.

* * * * *